United States Patent
Rottman

(10) Patent No.: US 12,397,028 B2
(45) Date of Patent: Aug. 26, 2025

(54) ADOPTIVE CELLULAR THERAPY

(71) Applicant: Regeneron Pharmaceuticals, Inc., Tarrytown, NY (US)

(72) Inventor: James Brian Rottman, Sudbury, MA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/734,010

(22) Filed: Jun. 5, 2024

(65) Prior Publication Data
US 2025/0009822 A1    Jan. 9, 2025

Related U.S. Application Data

(63) Continuation of application No. 17/046,466, filed as application No. PCT/US2019/027317 on Apr. 12, 2019, now Pat. No. 12,036,256.

(60) Provisional application No. 62/657,388, filed on Apr. 13, 2018.

(51) Int. Cl.
| | |
|---|---|
| A61P 35/00 | (2006.01) |
| A61K 35/763 | (2015.01) |
| A61K 40/10 | (2025.01) |
| A61K 40/31 | (2025.01) |
| A61K 40/42 | (2025.01) |
| A61P 35/04 | (2006.01) |
| C07K 14/725 | (2006.01) |
| C12N 7/00 | (2006.01) |
| C12N 15/113 | (2010.01) |
| C12N 15/63 | (2006.01) |
| A61K 39/00 | (2006.01) |

(52) U.S. Cl.
CPC ............ *A61K 35/763* (2013.01); *A61K 40/10* (2025.01); *A61K 40/31* (2025.01); *A61K 40/4211* (2025.01); *A61K 40/4215* (2025.01); *A61P 35/00* (2018.01); *C07K 14/7051* (2013.01); *C12N 7/00* (2013.01); *A61K 2039/5256* (2013.01); *C07K 2319/02* (2013.01); *C07K 2319/03* (2013.01); *C12N 2710/16621* (2013.01); *C12N 2710/16632* (2013.01)

(58) Field of Classification Search
CPC .......... A61P 35/00; A61P 35/04; A61P 37/04; C12N 7/00; C12N 15/113
See application file for complete search history.

(56) References Cited

U.S. PATENT DOCUMENTS

| | | |
|---|---|---|
| 12,036,256 B2 | 7/2024 | Rottman |
| 2013/0071430 A1 | 3/2013 | Nakamura et al. |
| 2017/0035819 A1 | 2/2017 | Uchida et al. |

FOREIGN PATENT DOCUMENTS

WO    2017/075440 A1    5/2017

OTHER PUBLICATIONS

Cai et al., Human microRNAs are processed from capped, polyadenylated transcripts that can also function as mRNAs. RNA. Dec. 2004; 10(12):1957-66.
Freedman et al., An Oncolytic Virus Expressing a T-cell Engager Simultaneously Targets Cancer and Immunosuppressive Stromal Cells. Cancer Res. Dec. 15, 2018;78(24):6852-6865.
Martinez et al., CAR T Cells for Solid Tumors: New Strategies for Finding, Infiltrating, and Surviving in the Tumor Microenvironment. Front Immunol. Feb. 5, 2019;10:128, 21 pages.
Park et al., Effective combination immunotherapy using oncolytic viruses to deliver CAR targets to solid tumors. Sci Transl Med. Sep. 2, 2020;12(559):eaaz1863, 29 pages.
Porter et al., Oncolytic Adenovirus Armed with BiTE, Cytokine, and Checkpoint Inhibitor Enables CAR T Cells to Control the Growth of Heterogeneous Tumors. Mol Ther. May 6, 2020;28(5):1251-1262.
Shi et al., Combining Oncolytic Viruses With Cancer Immunotherapy: Establishing a New Generation of Cancer Treatment. Front Immunol. Apr. 28, 2020; 11:683, 13 pages.
Wagner et al., CAR T Cell Therapy for Solid Tumors: Bright Future or Dark Reality? Mol Ther. Nov. 4, 2020;28(11):2320-2339.
International Search Report and Written Opinion for Application No. PCT/US2019/027317, dated Aug. 19, 2019, 14 pages.

*Primary Examiner* — Barry A Chestnut
(74) *Attorney, Agent, or Firm* — McCarter & English, LLP; Marcie B. Clarke; Dylan M. Blumenthal

(57) ABSTRACT

The invention provides improved compositions and methods for the treatment of solid cancers.

11 Claims, 1 Drawing Sheet
Specification includes a Sequence Listing.

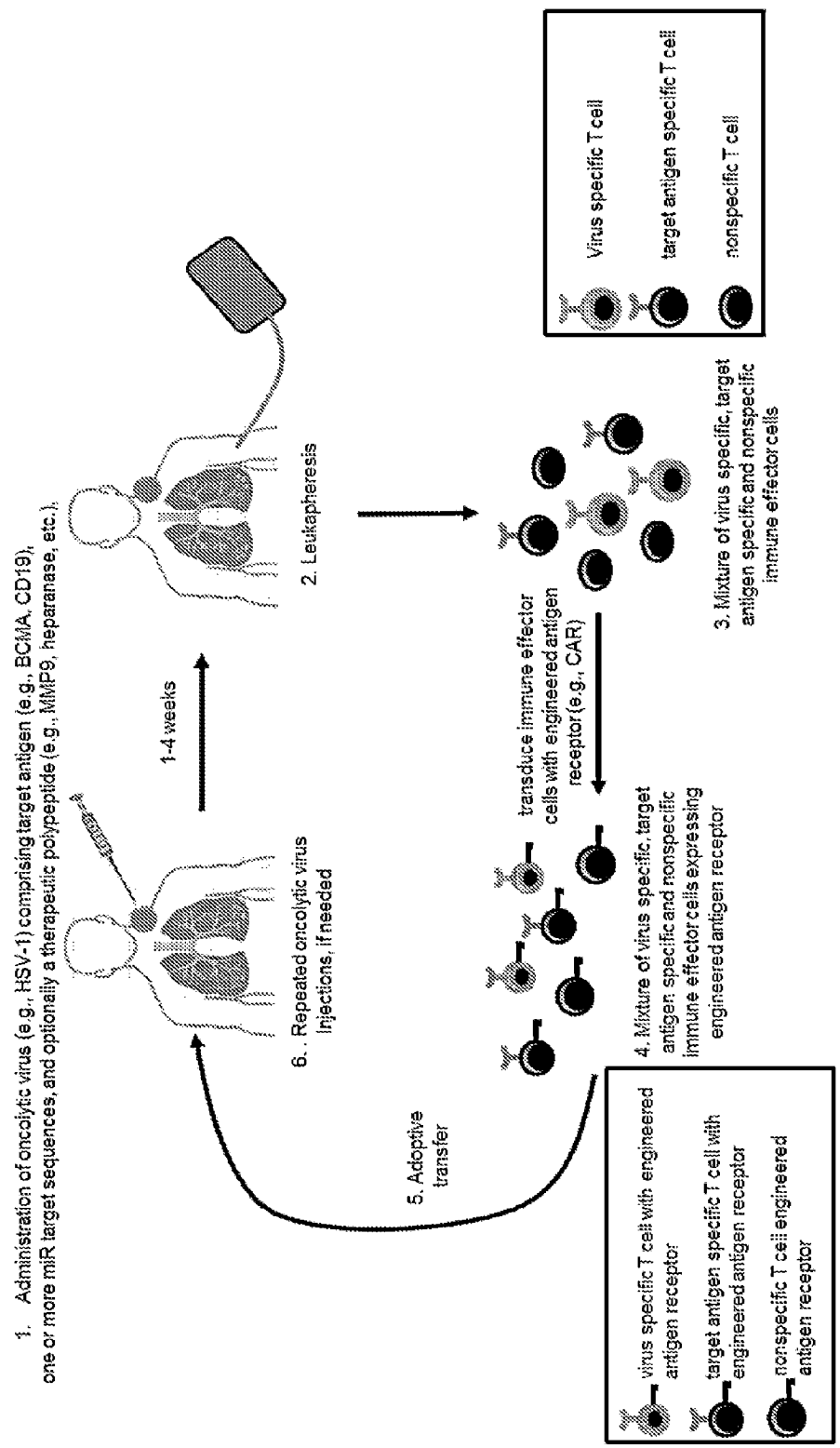

ADOPTIVE CELLULAR THERAPY

RELATED APPLICATIONS

This application is a Continuation Application of U.S. patent application Ser. No. 17/046,466, filed on Oct. 9, 2020, which is a 35 U.S.C. § 371 national stage filing of International Application No. PCT/US2019/027317, filed on Apr. 12, 2019, which claims the benefit of U.S. Provisional Application No. 62/657,388, filed Apr. 13, 2018, each of which are incorporated herein by reference in their entireties.

SEQUENCE LISTING

The application contains a Sequence Listing which has been submitted electronically in .XML format and is hereby incorporated by reference in its entirety. Said .XML copy, created on Jul. 2, 2024, is named "137080-00903.xml" and is 46,687 bytes in size. The sequence listing contained in this .XML file is part of the specification and is hereby incorporated by reference herein in its entirety.

BACKGROUND

Technical Field

The present disclosure relates to improved compositions and methods for using the same to treat cancer.

Description of the Related Art

Cancer is a significant health problem throughout the world. Based on rates from 2008-2010, 40.76% of men and women born today will be diagnosed with some form of cancer at some time during their lifetime. 20.37% of men will develop cancer between their 50th and 70th birthdays compared to 15.30% for women. On Jan. 1, 2010, in the United States there were approximately 13,027,914 men and women alive who had a history of cancer—6,078,974 men and 6,948,940 women. It is estimated that 1,660,290 men and women (854,790 men and 805,500 women) in the United States will be diagnosed with and 580,350 men and women will die of cancer of all sites in 2013. Howlader et al. 2013.

Most recently, adoptive cellular therapy strategies used to redirect immune effector cells to cancer cells have been explored and tested in early stage clinical trials. T cells have often been the effector cells of choice for cancer immunotherapy due to their selective recognition and powerful effector mechanisms. Patients treated with T cells modified to express chimeric antigen receptors (CARs) have experienced durable remissions for the treatment of B cell malignancies, but CAR T treatment of solid cancers has been largely unsuccessful.

One key factor responsible for the poor specificity and poor efficacy of CAR T cells against solid cancer is the lack of specific targetable antigens uniquely expressed by the cancer cells. Furthermore, to exploit their cytotoxic function CAR T cells need to overcome the limitations imposed by the physical and functional barriers of solid tumors and the immunosuppressive tumor microenvironment.

BRIEF SUMMARY

Aspects of the invention generally provide compositions and methods for treating cancer. More particularly, aspects of the invention provide oncolytic viral and adoptive cellular therapy compositions and methods of using the same to treat cancer.

In various embodiments, a recombinant oncolytic virus comprises a polynucleotide encoding a target antigen; and one or more tumor suppressor micro-RNA (miR) target sequences.

In certain embodiments, the oncolytic virus is an adenovirus, a coxsackievirus, a herpes simplex virus (HSV), a maraba virus, a measles virus, an orthomyxovirus, a parvovirus, a polio virus, a vaccinia virus, or a vesicular stomatitis virus.

In particular embodiments, the oncolytic virus is an HSV.

In some embodiments, the oncolytic virus is HSV-1.

In further embodiments, the target antigen is selected from the group consisting of: tumor associated antigens (TAA), tumor specific antigens (TSA), NKG2D ligands, γδ T cell receptor (TCR) ligands, and αβ TCR ligands.

In particular embodiments, the target antigen is selected from the group consisting of: alpha folate receptor (FRα), αvβ6 integrin, B cell maturation antigen (BCMA), B7-H3 (CD276), B7-H6, carbonic anhydrase IX (CAIX), CD16, CD19, CD20, CD22, CD30, CD33, CD37, CD38, CD44, CD44v6, CD44v7/8, CD70, CD79a, CD79b, CD123, CD133, CD138, CD171, carcinoembryonic antigen (CEA), C-type lectin-like molecule-1 (CLL-1), CD2 subset 1 (CS-1), chondroitin sulfate proteoglycan 4 (CSPG4), cutaneous T cell lymphoma-associated antigen 1 (CTAGE1), epidermal growth factor receptor (EGFR), epidermal growth factor receptor variant III (EGFRvIII), epithelial glycoprotein 2 (EGP2), epithelial glycoprotein 40 (EGP40), epithelial cell adhesion molecule (EPCAM), ephrin type-A receptor 2 (EPHA2), fibroblast activation protein (FAP), Fc Receptor Like 5 (FCRL5), fetal acetylcholinesterase receptor (AchR), ganglioside G2 (GD2), ganglioside G3 (GD3), Glypican-3 (GPC3), EGFR family including ErbB2 (HER2), IL-11R□, IL-13R□D2, Kappa, cancer/testis antigen 2 (LAGE-1A), Lambda, Lewis-Y (LeY), L1 cell adhesion molecule (L1-CAM), melanoma antigen gene (MAGE)-A1, MAGE-A3, MAGE-A4, MAGE-A6, MAGEA10, melanoma antigen recognized by T cells 1 (MelanA or MART1), Mesothelin (MSLN), MUC1, MUC16, MHC class I chain related proteins A (MICA), MHC class I chain related proteins B (MICB), neural cell adhesion molecule (NCAM), cancer/testis antigen 1 (NY-ESO-1), polysialic acid; placenta-specific 1 (PLAC1), preferentially expressed antigen in melanoma (PRAME), prostate stem cell antigen (PSCA), prostate-specific membrane antigen (PSMA), receptor tyrosine kinase-like orphan receptor 1 (ROR1), synovial sarcoma, X breakpoint 2 (SSX2), Survivin, tumor associated glycoprotein 72 (TAG72), tumor endothelial marker 1 (TEM1/CD248), tumor endothelial marker 7-related (TEM7R), trophoblast glycoprotein (TPBG), UL16-binding protein (ULBP) 1, ULBP2, ULBP3, ULBP4, ULBP5, ULBP6, vascular endothelial growth factor receptor 2 (VEGFR2), and Wilms tumor 1 (WT-1).

In particular embodiments, the target antigen is BCMA or CD19.

In certain embodiments, the target antigen is recognized by and/or bound by an engineered antigen receptor.

In particular embodiments, the target antigen is recognized by and/or bound by an engineered antigen receptor selected from the group consisting of: a chimeric antigen receptor (CAR), an engineered γδ TCR, and engineered αβ TCR, and an engineered NKG2D.

In various embodiments, the one or more tumor suppressor miR target sequences are inserted into one or more viral genes required for viral replication of the oncolytic virus.

In additional embodiments, the one or more tumor suppressor miR target sequences are not recognized and/or not bound by a miR endogenously expressed in a target cell.

In particular embodiments, the one or more tumor suppressor miR target sequences are recognized and/or bound by one or more miRs expressed in a non-target cell (a tumor suppressor miR).

In some embodiments, replication of the recombinant oncolytic virus is reduced or attenuated in a target cell compared to replication of the recombinant oncolytic virus in a non-target cell.

In certain embodiments, replication of the recombinant oncolytic virus is greater in a target cell compared to a non-target cell.

In particular embodiments, replication of the recombinant oncolytic virus is suppressed in a non-target cell.

In various embodiments, the recombinant oncolytic virus further comprises one or more polynucleotides encoding one or more therapeutic polypeptides.

In additional embodiments, the recombinant oncolytic virus further comprises one or more polynucleotides encoding one or more therapeutic polypeptides selected from the group consisting of: a bispecific T cell engager (BiTE), a checkpoint inhibitor, a cytokine, a protease, and an extracellular matrix remodeling enzyme.

In various embodiments, the recombinant oncolytic virus further comprises a viral capsid pseudotyped with one or more proteins, which bind one or more molecules present on the surface of a target cell.

In certain embodiments, the recombinant oncolytic virus further comprises a viral capsid pseudotyped with one or more non-viral proteins, which bind one or more molecules present on the surface of a target cell.

In particular embodiments, the recombinant oncolytic virus further comprises a modification of one or more non-essential viral genes.

In some embodiments, the recombinant oncolytic virus further comprises a modification of one or more viral genes non-essential for viral replication.

In various embodiments, a recombinant oncolytic herpes simplex virus (HSV) comprises a polynucleotide encoding a target antigen; and one or more tumor suppressor miR target sequences inserted into one or more essential viral genes required for viral replication.

In various embodiments, a recombinant oncolytic HSV comprises a polynucleotide encoding a target antigen not endogenously expressed on a target cell; and one or more tumor suppressor miR target sequences inserted into one or more essential viral genes required for viral replication.

In further embodiments, a recombinant oncolytic HSV comprises a polynucleotide encoding a non-viral target antigen not endogenously expressed on a target cell; and one or more tumor suppressor miR target sequences inserted into one or more essential viral genes required for viral replication.

In some embodiments, the HSV is HSV-1.

In various embodiments, one or more accessory viral genes are modified.

In additional embodiments, a portion of one or more accessory viral genes are modified by deletion.

In particular embodiments, one or more accessory viral genes are modified to be non-functional.

In particular embodiments, a portion of, or all of the joint region is modified and/or deleted.

In certain embodiments, the one or more accessory viral genes are selected from the group consisting of: the joint region, one or both copies of ICP-34.5, one or both copies of ICP0, one or both copies of LAT, UL2, UL3, UL4, UL10, UL11, UL13, UL16, UL20, UL21, UL29, UL34, UL39 (ICP6), UL40, UL41, UL43, UL 44, UL45, UL46, UL47, UL50, UL51, UL55, UL56, US1 (ICP22), US2, US3, US4, US5, US7, US8, US9, US10, US11, and US12 (ICP47, α47).

In various embodiments, the one or more viral genes are selected from the group consisting of: the joint region, one or both copies of ICP-34.5, UL39 (ICP6), and US12 (ICP47, α47).

In particular embodiments, the joint region, both copies of ICP-34.5, UL39 (ICP6), and US12 (ICP47, α47) are modified or deleted.

In further embodiments, the one or more viral genes are selected from the group consisting of: the joint region, one or both copies of ICP-34.5, and US12 (ICP47, α47).

In particular embodiments, the joint region, both copies of ICP-34.5 and US12 (ICP47, α47) are modified or deleted.

In certain embodiments, the oncolytic HSV further comprises a viral entry enhancing mutation or a viral spread enhancing mutation.

In various embodiments, the oncolytic HSV further comprises a gB:NT [D285N/A549T] viral entry enhancing mutation and/or a gH:KV [N753K/A778V] viral spread enhancing mutation.

In some embodiments, the oncolytic HSV further comprises a non-HSV polypeptide inserted into the gD gene or the gC gene.

In certain embodiments, the oncolytic HSV further comprises a non-HSV polypeptide inserted into the gD gene, replacing residues 2 to 24 of the gD gene.

In various embodiments, the oncolytic HSV further comprises a non-HSV polypeptide inserted into the gD gene, replacing residues 2 to 24 of the gD gene and residue 38 of the gD comprises a tyrosine to cysteine mutation.

In particular embodiments, the non-HSV polypeptide is a ligand that specifically or selectively binds a protein on the surface of the target cell.

In particular embodiments, the non-HSV polypeptide is a ligand selected from the group consisting of: an antibody or antigen binding fragment thereof, a hormone, or a growth factor.

In further embodiments, the non-HSV polypeptide is an antibody or antigen binding fragment thereof selected from the group consisting of: a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody).

In various embodiments, the non-HSV polypeptide binds a growth factor receptor expressed on a target cell.

In additional embodiments, the non-HSV polypeptide binds an epidermal growth factor receptor (EGFR) or splice variant thereof, expressed on a target cell.

In particular embodiments, the non-HSV polypeptide binds a checkpoint protein expressed on a target cell.

In certain embodiments, the non-HSV polypeptide binds a checkpoint protein selected from the group consisting of: PD-L1, PD-L2, and In further embodiments, the target antigen is selected from the group consisting of: tumor associated antigens (TAA), tumor specific antigens (TSA), NKG2D ligands, γδ T cell receptor (TCR) ligands, and αβ TCR ligands.

In various embodiments, the target antigen is selected from the group consisting of: alpha folate receptor (FRα), αvβ6 integrin, B cell maturation antigen (BCMA), B7-H3 (CD276), B7-H6, carbonic anhydrase IX (CAIX), CD16, CD19, CD20, CD22, CD30, CD33, CD37, CD38, CD44, CD44v6, CD44v7/8, CD70, CD79a, CD79b, CD123, CD133, CD138, CD171, carcinoembryonic antigen (CEA), C-type lectin-like molecule-1 (CLL-1), CD2 subset 1 (CS-1), chondroitin sulfate proteoglycan 4 (CSPG4), cutaneous T cell lymphoma-associated antigen 1 (CTAGE1), epidermal growth factor receptor (EGFR), epidermal growth factor receptor variant III (EGFRvIII), epithelial glycoprotein 2 (EGP2), epithelial glycoprotein 40 (EGP40), epithelial cell adhesion molecule (EPCAM), ephrin type-A receptor 2 (EPHA2), fibroblast activation protein (FAP), Fc Receptor Like 5 (FCRL5), fetal acetylcholinesterase receptor (AchR), ganglioside G2 (GD2), ganglioside G3 (GD3), Glypican-3 (GPC3), EGFR family including ErbB2 (HER2), IL-11Rα, IL-13Rα2, Kappa, cancer/testis antigen 2 (LAGE-1A), Lambda, Lewis-Y (LeY), L1 cell adhesion molecule (L1-CAM), melanoma antigen gene (MAGE)-A1, MAGE-A3, MAGE-A4, MAGE-A6, MAGEA10, melanoma antigen recognized by T cells 1 (MelanA or MART1), Mesothelin (MSLN), MUC1, MUC16, MHC class I chain related proteins A (MICA), MHC class I chain related proteins B (MICB), neural cell adhesion molecule (NCAM), cancer/testis antigen 1 (NY-ESO-1), polysialic acid; placenta-specific 1 (PLAC1), preferentially expressed antigen in melanoma (PRAME), prostate stem cell antigen (PSCA), prostate-specific membrane antigen (PSMA), receptor tyrosine kinase-like orphan receptor 1 (ROR1), synovial sarcoma, X breakpoint 2 (SSX2), Survivin, tumor associated glycoprotein 72 (TAG72), tumor endothelial marker 1 (TEM1/CD248), tumor endothelial marker 7-related (TEM7R), trophoblast glycoprotein (TPBG), UL16-binding protein (ULBP) 1, ULBP2, ULBP3, ULBP4, ULBP5, ULBP6, vascular endothelial growth factor receptor 2 (VEGFR2), and Wilms tumor 1 (WT-1).

In particular embodiments, the target antigen is BCMA or CD19.

In additional embodiments, the target antigen is recognized by and/or bound by an engineered antigen receptor.

In particular embodiments, the target antigen is recognized by and/or bound by an engineered antigen receptor selected from the group consisting of: a CAR, an engineered γδ TCR, and engineered αβ TCR, and an engineered NKG2D.

In some embodiments, the one or more tumor suppressor miR target sequences are inserted into one or more essential viral genes required for viral replication of the oncolytic HSV.

In certain embodiments, the one or more tumor suppressor miR target sequences are not recognized and/or not bound by a miR endogenously expressed in a target cell.

In various embodiments, the one or more tumor suppressor miR target sequences are recognized and/or bound by one or more miRs expressed in a non-target cell.

In particular embodiments, replication of the recombinant oncolytic HSV is reduced or attenuated in a target cell compared to replication of the recombinant oncolytic HSV in a non-target cell.

In particular embodiments, replication of the recombinant oncolytic HSV is greater in a target cell compared to a non-target cell.

In further embodiments, replication of the recombinant oncolytic HSV is suppressed in a non-target cell.

In certain embodiments, the one or more tumor suppressor miR target sequences are inserted into a 5' UTR, intron, and/or 3' UTR of an essential viral gene.

In various embodiments, the one or more tumor suppressor miR target sequences are inserted into a 5' UTR, intron, and/or 3' UTR of an essential viral gene selected from the group consisting of: UL1, UL5, UL6, UL7, UL8, UL9, UL12, UL14, UL15, UL17, UL18, UL19, UL22, UL23, UL24, UL25, UL2, UL27, UL28, UL29, UL30, UL31, UL32, UL33, UL35, UL36, UL37, UL38, UL42, UL48, UL49, UL52, UL53, UL54 (ICP27), one or both copies of ICP4, and US6.

In particular embodiments, the one or more tumor suppressor miR target sequences are inserted into a 5' UTR, intron, and/or 3' UTR of an essential viral gene selected from the group consisting of: UL19, UL30, UL54 (ICP27), and one or both copies of ICP4.

In particular embodiments, the one or more tumor suppressor miR target sequences are inserted into a 5' UTR, intron, and/or 3' UTR of an essential viral gene selected from the group consisting of: UL54 (ICP27) and one or both copies of ICP4.

In some embodiments, the one or more tumor suppressor miR target sequences are inserted into a 5' UTR, intron, and/or 3' UTR of UL54 (ICP27) and one copy of ICP4.

In various embodiments, the one or more tumor suppressor miR target sequences are inserted into a 5' UTR, intron, and/or 3' UTR of UL54 (ICP27) and both copies of ICP4.

In certain embodiments, the target cell is a cancer cell.

In particular embodiments, the non-cancer cell is in a tissue near to the target cell.

In particular embodiments, the non-cancer cell is in a tissue adjacent to the target cell.

In further embodiments, the one or more tumor suppressor miRs target sequences are recognized by and/or bound by one or more tumor suppressor miRs.

In various embodiments, the one or more tumor suppressor miRs target sequences are recognized by and/or bound by one or more tumor suppressor miRs selected from the group consisting of: hsa-miR-1-3p, hsa-miR-124-3p, hsa-miR-143-3p, hsa-miR-145-5p, hsa-miR-451a, and hsa-miR-559.

In certain embodiments, the one or more tumor suppressor miRs target sequences are recognized by and/or bound by one or more tumor suppressor miRs selected from the group consisting of: hsa-miR-1-3p, hsa-miR-124-3p, hsa-miR-145-5p, hsa-miR-451a, and hsa-miR-559.

In particular embodiments, the one or more tumor suppressor miRs target sequences are recognized by and/or bound by one or more tumor suppressor miRs selected from the group consisting of: hsa-miR-124-3p, hsa-miR-143-3p, hsa-miR-451a, and hsa-miR-559.

In certain embodiments, the one or more tumor suppressor miRs target sequences are recognized and/or bound by one or more tumor suppressor miRs selected from the group consisting of: hsa-miR-124-3p, hsa-miR-145-5p, hsa-miR-451a, and hsa-miR-559.

In certain embodiments, the one or more tumor suppressor miRs target sequences are recognized by and/or bound by one or more tumor suppressor miRs selected from the group consisting of: hsa-miR-124-3p, hsa-miR-145-5p, and hsa-miR-143-3p.

In various embodiments, the one or more tumor suppressor miRs target sequences are recognized by and/or bound by one or more tumor suppressor miRs selected from the group consisting of: hsa-miR-31-5p, hsa-miR-124-3p, hsa-miR-141-5p, and hsa-miR-205.

In some embodiments, the one or more tumor suppressor miRs target sequences are recognized by and/or bound by hsa-miR-1-3p.

In particular embodiments, the one or more tumor suppressor miRs target sequences are recognized by and/or bound by hsa-miR-124-3p.

In additional embodiments, the one or more tumor suppressor miRs target sequences are recognized by and/or bound by hsa-miR-145-5p.

In some embodiments, the one or more tumor suppressor miRs target sequences are recognized by and/or bound by hsa-miR-143-3p.

In additional embodiments, the one or more tumor suppressor miRs target sequences are recognized by and/or bound by hsa-miR-451a.

In various embodiments, the one or more tumor suppressor miRs target sequences are recognized by and/or bound by hsa-miR-559.

In various embodiments, the target cell is a solid cancer cell.

In certain embodiments, the solid cancer is selected from the group consisting of: adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain/CNS cancer, breast cancer, bronchial tumors, cardiac tumors, cervical cancer, cholangiocarcinoma, chondrosarcoma, chordoma, colon cancer, colorectal cancer, craniopharyngioma, ductal carcinoma in situ (DCIS) endometrial cancer, ependymoma, esophageal cancer, esthesioneuroblastoma, Ewing's sarcoma, extracranial germ cell tumor, extragonadal germ cell tumor, eye cancer, fallopian tube cancer, fibrous histiosarcoma, fibrosarcoma, gallbladder cancer, gastric cancer, gastrointestinal carcinoid tumors, gastrointestinal stromal tumor (GIST), germ cell tumors, glioma, glioblastoma, head and neck cancer, hemangioblastoma, hepatocellular cancer, hypopharyngeal cancer, intraocular melanoma, kaposi sarcoma, kidney cancer, laryngeal cancer, leiomyosarcoma, lip cancer, liposarcoma, liver cancer, lung cancer, non-small cell lung cancer, lung carcinoid tumor, malignant mesothelioma, medullary carcinoma, medulloblastoma, menangioma, melanoma, Merkel cell carcinoma, midline tract carcinoma, mouth cancer, myxosarcoma, myelodysplastic syndrome, myeloproliferative neoplasms, nasal cavity and paranasal sinus cancer, nasopharyngeal cancer, neuroblastoma, oligodendroglioma, oral cancer, oral cavity cancer, oropharyngeal cancer, osteosarcoma, ovarian cancer, pancreatic cancer, pancreatic islet cell tumors, papillary carcinoma, paraganglioma, parathyroid cancer, penile cancer, pharyngeal cancer, pheochromocytoma, pinealoma, pituitary tumor, pleuropulmonary blastoma, primary peritoneal cancer, prostate cancer, rectal cancer, retinoblastoma, renal cell carcinoma, renal pelvis and ureter cancer, rhabdomyosarcoma, salivary gland cancer, sebaceous gland carcinoma, skin cancer, soft tissue sarcoma, squamous cell carcinoma, small cell lung cancer, small intestine cancer, stomach cancer, sweat gland carcinoma, synovioma, testicular cancer, throat cancer, thymus cancer, thyroid cancer, urethral cancer, uterine cancer, uterine sarcoma, vaginal cancer, vascular cancer, vulvar cancer, and Wilms Tumor.

In particular embodiments, the solid cancer is selected from the group consisting of: liver cancer, pancreatic cancer, lung cancer, breast cancer, brain cancer, bladder cancer, thyroid cancer, kidney cancer, and skin cancer.

In some embodiments, the solid cancer is selected from the group consisting of: bladder cancer, breast cancer, colon cancer, glioblastoma, head and neck cancer, lung cancer, pancreatic cell, or a schwannoma.

In particular embodiments, the target cell is a liquid cancer cell.

In various embodiments, the recombinant oncolytic HSV further comprises one or more polynucleotides encoding one or more therapeutic polypeptides.

In certain embodiments, the recombinant oncolytic HSV further comprises one or more polynucleotides encoding one or more therapeutic polypeptides selected from the group consisting of: a bispecific T cell engager (BiTE), a checkpoint inhibitor, a cytokine, a protease, and an extracellular matrix remodeling enzyme.

In further embodiments, the bispecific T cell engager (BiTE) is selected from the group consisting of: a CD19/CD3 BiTE, a CD20/CD3 BiTE, a CD22/CD3 BiTE, a CD38/CD3 BiTE, a BCMA/CD3 BiTE, a FAP/CD3 BiTE, a PD-L1/CD3 BiTE, and a PD-L2/CD3 BiTE.

In various embodiments, the BiTE comprises scFvs that bind CD19 and CD3, CD20 and CD3, CD22 and cD3, CD38 and CD3, BCMA and CD3, FAP and CD3, PD-L1 and CD3, or PD-L2 and CD3.

In particular embodiments, the checkpoint inhibitor reduces or decreases signaling of a checkpoint protein selected from the group consisting of: PD-L1, PD-L2, PD-1, LAG-3, TIM-3, CTLA-4, TIGIT, TGFβ, and TGFβR.

In various embodiments, the cytokine is selected from the group consisting of: IL-2, insulin, IFN-7, IL-7, IL-21, IL-10, IL-12, IL-15, and TNF-α.

In some embodiments, the protease is selected from the group consisting of: a cathepsin, a kallikrein, and a serine protease.

In certain embodiments, the extracellular remodeling enzyme is a disintegrin metalloproteinase (ADAM) or is selected from the group consisting of: MMP-1, MMP-2, MMP-3, MMP-7, MMP-8, MMP-9, MMP-10, MMP-11. MMP-12, MMP-13, MMP-14, MMP-15, MMP-16, MMP-17, MMP-18, MMP-19, MMP-20, MMP-21, MMP-23A, MMP-23B, MMP-24, MMP-25, MMP-26, MMP-27, and MMP-28.

In additional embodiments, the extracellular remodeling enzyme is MMP-9.

In particular embodiments, a pseudotyped oncolytic HSV-1 comprises: a polynucleotide encoding a target antigen selected from the group consisting of CD19 and BCMA; a polynucleotide encoding human MMP-9 inserted into a non-essential viral gene and/or deleted joint region; and one or more tumor suppressor miR target sequences recognized and/or bound by a miR selected from the group consisting of hsa-miR-1-3p, hsa-miR-124-3p, hsa-miR-143-3p, hsa-miR-145-5p, hsa-miR-451a, and hsa-miR-559 inserted into one or more essential viral genes required for viral replication selected from the group consisting of ICP4 and ICP27.

In various embodiments, a pseudotyped oncolytic HSV-1 comprises: a polynucleotide encoding a target antigen selected from the group consisting of CD19 and BCMA; a polynucleotide encoding human MMP-9 inserted into a non-essential viral gene and/or deleted joint region; and one or more tumor suppressor miR target sequences recognized and/or bound by a miR selected from the group consisting of hsa-miR-1-3p, hsa-miR-124-3p, hsa-miR-143-3p, hsa-miR-145-5p, hsa-miR-451a, and hsa-miR-559 inserted into one or more essential viral genes required for viral replication selected from the group consisting of ICP4 and ICP27; wherein the HSV-1 further comprises one or more modified non-essential viral genes selected from the group consisting of one or more copies of the ICP34.5 gene, the ICP6 gene, and the ICP47 gene.

In certain embodiments, a pseudotyped oncolytic HSV-1 comprises: a polynucleotide encoding a target antigen selected from the group consisting of CD19 and BCMA; a polynucleotide encoding human MMP-9 inserted into a non-essential viral gene and/or deleted joint region; and one or more tumor suppressor miR target sequences recognized and/or bound by a miR selected from the group consisting of hsa-miR-1-3p, hsa-miR-124-3p, hsa-miR-143-3p, hsa-miR-145-5p, hsa-miR-451a, and hsa-miR-559 inserted into one or more essential viral genes required for viral replication selected from the group consisting of ICP4 and ICP27; wherein the HSV-1 further comprises one or more modified non-essential viral genes selected from the group consisting of one or more copies of the ICP34.5 gene, the ICP6 gene, and the ICP47 gene; and wherein the HSV-1 further comprises a gB:NT mutation, and optionally a gH:KV mutation.

In some embodiments, an engineered antigen receptor comprises: an extracellular antigen binding domain that binds a target antigen ectopically expressed by an oncolytic vector contemplated herein on a target cell; a transmembrane domain; and one or more intracellular signaling domains and/or primary signaling domains.

In various embodiments, a method of treating a subject in need thereof comprises: administering to the subject an oncolytic virus contemplated herein; isolating immune effector cells from the subject; transducing the immune effector cells with vector encoding an engineered antigen receptor contemplated herein; and administering the transduced immune effector cells to the subject; wherein the transduced immune effectors cells bind the target antigen expressed on the target cell and induce cytolysis of the target cell.

In further embodiments, a method of treating a subject in need thereof comprises: administration of an oncolytic virus encoding a target antigen and one or more tumor suppressor miR target sequences to a population of cancer cells in the subject; isolating immune effector cells from the subject; transducing the immune effector cells with vector encoding an engineered antigen receptor; and administering the transduced immune effector cells to the subject; wherein the transduced immune effectors cells bind the target antigen expressed on the one or more target cells and induce cytolysis of the one or more target cells.

In particular embodiments, the subject has been diagnosed with cancer.

In additional embodiments, the subject has a solid cancer.

In various embodiments, the cancer cells are from a cancer selected from the group consisting of: adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain/CNS cancer, breast cancer, bronchial tumors, cardiac tumors, cervical cancer, cholangiocarcinoma, chondrosarcoma, chordoma, colon cancer, colorectal cancer, craniopharyngioma, ductal carcinoma in situ (DCIS) endometrial cancer, ependymoma, esophageal cancer, esthesioneuroblastoma, Ewing's sarcoma, extracranial germ cell tumor, extragonadal germ cell tumor, eye cancer, fallopian tube cancer, fibrous histiosarcoma, fibrosarcoma, gallbladder cancer, gastric cancer, gastrointestinal carcinoid tumors, gastrointestinal stromal tumor (GIST), germ cell tumors, glioma, glioblastoma, head and neck cancer, hemangioblastoma, hepatocellular cancer, hypopharyngeal cancer, intraocular melanoma, kaposi sarcoma, kidney cancer, laryngeal cancer, leiomyosarcoma, lip cancer, liposarcoma, liver cancer, lung cancer, non-small cell lung cancer, lung carcinoid tumor, malignant mesothelioma, medullary carcinoma, medulloblastoma, menangioma, melanoma, Merkel cell carcinoma, midline tract carcinoma, mouth cancer, myxosarcoma, myelodysplastic syndrome, myeloproliferative neoplasms, nasal cavity and paranasal sinus cancer, nasopharyngeal cancer, neuroblastoma, oligodendroglioma, oral cancer, oral cavity cancer, oropharyngeal cancer, osteosarcoma, ovarian cancer, pancreatic cancer, pancreatic islet cell tumors, papillary carcinoma, paraganglioma, parathyroid cancer, penile cancer, pharyngeal cancer, pheochromocytoma, pinealoma, pituitary tumor, pleuropulmonary blastoma, primary peritoneal cancer, prostate cancer, rectal cancer, retinoblastoma, renal cell carcinoma, renal pelvis and ureter cancer, rhabdomyosarcoma, salivary gland cancer, sebaceous gland carcinoma, skin cancer, soft tissue sarcoma, squamous cell carcinoma, small cell lung cancer, small intestine cancer, stomach cancer, sweat gland carcinoma, synovioma, testicular cancer, throat cancer, thymus cancer, thyroid cancer, urethral cancer, uterine cancer, uterine sarcoma, vaginal cancer, vascular cancer, vulvar cancer, and Wilms Tumor.

In some embodiments, the cancer cells are from a solid cancer selected from the group consisting of: liver cancer, pancreatic cancer, lung cancer, breast cancer, bladder cancer, brain cancer, bone cancer, thyroid cancer, kidney cancer, and skin cancer.

In particular embodiments, the cancer cells are from a solid cancer selected from the group consisting of: bladder cancer, breast cancer, colon cancer, glioblastoma, head and neck cancer, lung cancer, pancreatic cell, or a schwannoma.

In various embodiments, the subject has a liquid cancer.

In certain embodiments, the oncolytic virus administration to the subject is intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection or infusion.

In additional embodiments, the oncolytic virus is intravenously administered to the subject.

In various embodiments, the oncolytic virus is intratumorially administered to the subject.

In further embodiments, the target antigen is selected from the group consisting of: tumor associated antigens (TAA), tumor specific antigens (TSA), NKG2D ligands, γδ T cell receptor (TCR) ligands, and αβ TCR ligands.

In particular embodiments, the target antigen is selected from the group consisting of: alpha folate receptor (FRα), αvβ6 integrin, B cell maturation antigen (BCMA), B7-H3 (CD276), B7-H6, carbonic anhydrase IX (CAIX), CD16, CD19, CD20, CD22, CD30, CD33, CD37, CD38, CD44, CD44v6, CD44v7/8, CD70, CD79a, CD79b, CD123, CD133, CD138, CD171, carcinoembryonic antigen (CEA), C-type lectin-like molecule-1 (CLL-1), CD2 subset 1 (CS-1), chondroitin sulfate proteoglycan 4 (CSPG4), cutaneous T cell lymphoma-associated antigen 1 (CTAGE1), epidermal growth factor receptor (EGFR), epidermal growth factor receptor variant III (EGFRvIII), epithelial glycoprotein 2 (EGP2), epithelial glycoprotein 40 (EGP40), epithelial cell adhesion molecule (EPCAM), ephrin type-A receptor 2 (EPHA2), fibroblast activation protein (FAP), Fe Receptor Like 5 (FCRL5), fetal acetylcholinesterase receptor (AchR), ganglioside G2 (GD2), ganglioside G3 (GD3), Glypican-3 (GPC3), EGFR family including ErbB2 (HER2), IL-11R☐, IL-13R☐D2, Kappa, cancer/testis antigen 2 (LAGE-1A), Lambda, Lewis-Y (LeY), L1 cell adhesion molecule (L1-CAM), melanoma antigen gene (MAGE)-A1, MAGE-A3, MAGE-A4, MAGE-A6, MAGEA10, melanoma antigen recognized by T cells 1 (MelanA or MART1), Mesothelin (MSLN), MUC1, MUC16, MHC class I chain related proteins A (MICA), MHC class I chain related proteins B (MICB), neural cell adhesion molecule (NCAM), cancer/testis antigen 1 (NY-ESO-1), polysialic acid; placenta-specific 1 (PLAC1), preferentially expressed antigen in melanoma (PRAME), prostate stem cell antigen (PSCA), prostate-specific membrane antigen (PSMA), receptor tyrosine kinase-like orphan receptor 1 (ROR1), synovial sarcoma, X breakpoint 2 (SSX2), Survivin, tumor associated glycoprotein 72 (TAG72), tumor endothelial marker 1 (TEM1/CD248), tumor endothelial marker 7-related (TEM7R), trophoblast glycoprotein (TPBG), UL16-binding protein (ULBP) 1, ULBP2, ULBP3, ULBP4, ULBP5, ULBP6, vascular endothelial growth factor receptor 2 (VEGFR2), and Wilms tumor 1 (WT-1).

In additional embodiments, the target antigen is BCMA or CD19.

In various embodiments, the one or more tumor suppressor miR target sequences are inserted into one or more essential viral genes required for viral replication of the oncolytic virus.

In particular embodiments, the one or more tumor suppressor miR target sequences are not recognized and/or not bound by a miR endogenously expressed in a target cell.

In certain embodiments, the one or more tumor suppressor miR target sequences are recognized and/or bound by one or more miRs expressed in a non-target cell.

In various embodiments, replication of the recombinant oncolytic virus is reduced or attenuated in a cancer cell compared to replication of the recombinant oncolytic virus in a non-target cell.

In some embodiments, replication of the recombinant oncolytic virus is greater in a cancer cell compared to a non-target cell.

In additional embodiments, replication of the recombinant oncolytic virus is suppressed in a non-target cell.

In particular embodiments, the one or more tumor suppressor miR target sequences are inserted into a 5' UTR, intron, and/or 3' UTR of an essential viral gene.

In certain embodiments, the oncolytic virus is a herpes simplex virus (HSV), an adenovirus, a polio virus, a vaccinia virus, a measles virus, a vesicular stomatitis virus, an orthomyxovirus, a parvovirus, a maraba virus or a coxsackievirus.

In additional embodiments, the oncolytic virus is an HSV.

In various embodiments, the oncolytic virus is HSV-1.

In further embodiments, the one or more tumor suppressor miR target sequences are inserted into a 5' UTR, intron, and/or 3' UTR of an essential viral gene selected from the group consisting of: UL1, UL5, UL6, UL7, UL8, UL9, UL12, UL14, UL15, UL17, UL18, UL19, UL22, UL23, UL24, UL25, UL2, UL27, UL28, UL29, UL30, UL31, UL32, UL33, UL35, UL36, UL37, UL38, UL42, UL48, UL49, UL52, UL53, UL54 (ICP27), one or both copies of ICP4, and US6.

In various embodiments, the one or more tumor suppressor miR target sequences are inserted into a 5' UTR, intron, and/or 3' UTR of an essential viral gene selected from the group consisting of: UL19, UL30, UL54 (ICP27), and one or both copies of ICP4.

In particular embodiments, the one or more tumor suppressor miR target sequences are inserted into a 5' UTR, intron, and/or 3' UTR of an essential viral gene selected from the group consisting of: UL54 (ICP27) and one or both copies of ICP4.

In some embodiments, the one or more tumor suppressor miR target sequences are inserted into a 5' UTR, intron, and/or 3' UTR of UL54 (ICP27) and one copy of ICP4.

In additional embodiments, the one or more tumor suppressor miR target sequences are inserted into a 5' UTR, intron, and/or 3' UTR of UL54 (ICP27) and both copies of ICP4.

In particular embodiments, the one or more tumor suppressor miRs target sequences are recognized by and/or bound by one or more tumor suppressor miRs selected from the group consisting of: hsa-miR-1-3p, hsa-miR-124-3p, hsa-miR-143-3p, hsa-miR-145-5p, hsa-miR-451a, and hsa-miR-559.

In some embodiments, the one or more tumor suppressor miRs target sequences are recognized by and/or bound by one or more tumor suppressor miRs selected from the group consisting of: hsa-miR-1-3p, hsa-miR-124-3p, hsa-miR-145-5p, hsa-miR-451a, and hsa-miR-559.

In particular embodiments, the one or more tumor suppressor miRs target sequences are recognized by and/or bound by one or more tumor suppressor miRs selected from the group consisting of: hsa-miR-124-3p, hsa-miR-143-3p, hsa-miR-451a, and hsa-miR-559.

In particular embodiments, the one or more tumor suppressor miRs target sequences are recognized by and/or bound by one or more tumor suppressor miRs selected from the group consisting of: hsa-miR-124-3p, hsa-miR-143-3p, and hsa-miR-145-5p.

In certain embodiments, the one or more tumor suppressor miRs target sequences are recognized by and/or bound by one or more tumor suppressor miRs selected from the group consisting of: hsa-miR-124-3p, hsa-miR-145-5p, hsa-miR-451a, and hsa-miR-559.

In various embodiments, the one or more tumor suppressor miRs target sequences are recognized by and/or bound by one or more tumor suppressor miRs selected from the group consisting of: hsa-miR-31-5p, hsa-miR-124-3p, hsa-miR-141-5p, and hsa-miR-205.

In various embodiments, the one or more tumor suppressor miRs target sequences are recognized by and/or bound by hsa-miR-1-3p.

In various embodiments, the one or more tumor suppressor miRs target sequences are recognized by and/or bound by hsa-miR-124-3p.

In particular embodiments, the one or more tumor suppressor miRs target sequences are recognized by and/or bound by hsa-miR-145-5p.

In particular embodiments, the one or more tumor suppressor miRs target sequences are recognized by and/or bound by hsa-miR-143-3p.

In additional embodiments, the one or more tumor suppressor miRs target sequences are recognized by and/or bound by hsa-miR-451a.

In particular embodiments, the one or more tumor suppressor miRs target sequences are recognized by and/or bound by hsa-miR-559.

In additional embodiments, the oncolytic virus comprises one or more modified accessory viral genes.

In particular embodiments, a portion of one or more accessory viral genes of the oncolytic virus are modified by deletion.

In various embodiments, a portion of one or more accessory viral genes are modified to be non-functional.

In some embodiments, the oncolytic virus is HSV-1.

In certain embodiments, a portion of, or all of the joint region is modified and/or deleted.

In further embodiments, the one or more accessory viral genes are selected from the group consisting of: the joint region, one or both copies of ICP-34.5, one or both copies of ICP0, one or both copies of LAT, UL2, UL3, UL4, UL10, UL11, UL13, UL16, UL20, UL21, UL29, UL34, UL39 (ICP6), UL40, UL41, UL43, UL 44, UL45, UL46, UL47, UL50, UL51, UL55, UL56, US1 (ICP22), US2, US3, US4, US5, US7, US8, US9, US10, US11, and US12 (ICP47, α47).

In various embodiments, the one or more viral genes are selected from the group consisting of: the joint region, one or both copies of ICP-34.5, UL39 (ICP6), and US12 (ICP47, α47).

In further embodiments, the joint region, both copies of ICP-34.5, UL39 (ICP6), and US12 (ICP47, α47) are modified or deleted.

In particular embodiments, the one or more viral genes are selected from the group consisting of: the joint region, one or both copies of ICP-34.5, and US12 (ICP47, α47).

In various embodiments, the joint region, both copies of ICP-34.5 and US12 (ICP47, α47) are modified or deleted.

In certain embodiments, the oncolytic virus further comprises a viral entry enhancing mutation and/or a viral spread enhancing mutation.

In some embodiments, the oncolytic virus is HSV-1.

In particular embodiments, the oncolytic virus further comprises a gB:NT [D285N/A549T] viral entry enhancing mutation and/or a gH:KV [N753K/A778V] viral spread enhancing mutation.

In additional embodiments, the oncolytic virus further comprises a non-HSV polypeptide inserted into the gD gene or the gC gene.

In certain embodiments, the oncolytic virus further comprises a non-HSV polypeptide inserted into the gD gene, replacing residues 2 to 24 of the gD gene.

In certain embodiments, the oncolytic virus further comprises a non-HSV polypeptide inserted into the gD gene, replacing residues 2 to 24 of the gD gene and residue 38 of the gD comprises a tyrosine to cysteine mutation.

In additional embodiments, the non-HSV polypeptide is a ligand that specifically or selectively binds a protein on the surface of the target cell.

In various embodiments, the non-HSV polypeptide is a ligand selected from the group consisting of: an antibody or antigen binding fragment thereof, a hormone, or a growth factor.

In some embodiments, the non-HSV polypeptide is an antibody or antigen binding fragment thereof selected from the group consisting of: a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody).

In various embodiments, the non-HSV polypeptide binds a growth factor receptor expressed on a target cell.

In some embodiments, the non-HSV polypeptide binds an epidermal growth factor receptor (EGFR) or splice variant thereof, expressed on a target cell.

In various embodiments, the non-HSV polypeptide binds a checkpoint protein expressed on a target cell.

In particular embodiments, the non-HSV polypeptide binds a checkpoint protein selected from the group consisting of: PD-L1, PD-L2, and In additional embodiments, the oncolytic virus further comprises one or more polynucleotides encoding one or more therapeutic polypeptides.

In certain embodiments, the oncolytic virus further comprises one or more polynucleotides encoding one or more therapeutic polypeptides selected from the group consisting of: a bispecific T cell engager (BiTE), a checkpoint inhibitor, a cytokine, and a protease.

In various embodiments, the oncolytic virus further comprises, wherein the bispecific T cell engager (BiTE) is selected from the group consisting of: a CD19/CD3 BiTE, a BCMA/CD3 BiTE, a FAP/CD3 BiTE, a PD-L1/CD3 BiTE, and a PD-L2/CD3 BiTE.

In particular embodiments, the BiTE comprises scFvs that bind CD19 and CD3, CD20 and CD3, CD22 and cD3, CD38 and CD3, BCMA and CD3, FAP and CD3, PD-L1 and CD3, or PD-L2 and CD3.

In various embodiments, the checkpoint inhibitor reduces or decreases signaling of a checkpoint protein selected from the group consisting of: PD-L1, PD-L2, PD-1, LAG-3, TIM-3, CTLA-4, TIGIT, TGFβ, and TGFβR.

In further embodiments, the cytokine is selected from the group consisting of: IL-2, insulin, IFN-γ, IL-7, IL-21, IL-10, IL-12, IL-15, and TNF-α.

In particular embodiments, the protease is selected from the group consisting of: a cathepsin, a kallikrein, a serine protease, a matrix metalloproteinase (MMP), and a disintegrin metalloproteinase (ADAM).

In certain embodiments, the protease is selected from the group consisting of: MMP-1, MMP-2, MMP-3, MMP-7, MMP-8, MMP-9, MMP-10, MMP-11. MMP-12, MMP-13, MMP-14, MMP-15, MMP-16, MMP-17, MMP-18, MMP-19, MMP-20, MMP-21, MMP-23A, MMP-23B, MMP-24, MMP-25, MMP-26, MMP-27, and MMP-28.

In some embodiments, the protease is MMP-9.

In particular embodiments, the immune effector cells are isolated from the subject about 1 week after administration of the oncolytic virus.

In various embodiments, the immune effector cells are isolated from the subject about 2 weeks after administration of the oncolytic virus.

In additional embodiments, the immune effector cells are isolated from the subject about 3 weeks after administration of the oncolytic virus.

In various embodiments, the immune effector cells are isolated from the subject about 4 weeks after administration of the oncolytic virus.

In various embodiments, the immune effector cells are isolated from the subject about 1 week to about 4 weeks after administration of the oncolytic virus.

In some embodiments, the isolated immune effector cells comprise T cells, NK cells, NKT cells.

In particular embodiments, the isolated immune effector cells comprise T cells specific for the oncolytic virus, T cells specific for the target antigen and non-specific T cells.

In additional embodiments, the isolated immune effector cells comprise αβ T cells specific for the oncolytic virus and/or target antigen and/or γδ T cells specific for the oncolytic virus and/or target antigen.

In further embodiments, the isolated immune effector cells are transduced with a vector encoding an engineered antigen receptor that recognizes and/or binds the target antigen.

In various embodiments, the vector is a retroviral vector.

In various embodiments, the vector is a lentiviral vector.

In various embodiments, the engineered antigen receptor is selected from the group consisting of: a CAR, an engineered γδ TCR, and engineered αβ TCR, and an engineered NKG2D.

In certain embodiments, the CAR comprises and extracellular antigen binding domain that binds the target antigen, a transmembrane domain and one or more intracellular signaling domains.

In particular embodiments, the CAR comprises an antibody or antigen binding fragment is selected from the group consisting of: a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody).

In various embodiments, the extracellular binding domain is an scFv that binds BCMA or CD19.

In some embodiments, the CAR comprises a transmembrane domain isolated from a polypeptide selected from the group consisting of: alpha or beta chain of the T-cell receptor, CDδ, CD3ε, CDγ, CD3ζ, CD4, CD5, CD8α, CD9, CD 16, CD22, CD27, CD28, CD33, CD37, CD45, CD64, CD71, CD80, CD86, CD 134, CD137, CD152, CD154, AMN, and PD1.

In particular embodiments, the CAR comprises a transmembrane domain isolated from a polypeptide selected from the group consisting of: CD8α; CD4, CD45, PD1, and CD152.

In additional embodiments, the CAR comprises a CD8α transmembrane domain.

In various embodiments, the CAR comprises one or more intracellular signaling domains selected from the group consisting of: co-stimulatory signaling domains and primary signaling domains.

In further embodiments, the CAR comprises one or more co-stimulatory signaling domains isolated from a co-stimulatory molecule selected from the group consisting of: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70.

In various embodiments, the CAR comprises one or more co-stimulatory signaling domains isolated from a co-stimulatory molecule selected from the group consisting of: CD28, CD134, CD137, and CD278.

In certain embodiments, the CAR comprises a CD137 co-stimulatory signaling domain.

In particular embodiments, the CAR comprises a primary signaling domain isolated from a polypeptide selected from the group consisting of: FcRγ, FcRβ, CD3γ, CD3δ, CD3ε, CD3ζ, CD22, CD79a, CD79b, and CD66d.

In some embodiments, the CAR comprises a CD3ζ primary signaling domain.

In particular embodiments, the CAR comprises an amino acid sequence set forth in SEQ ID NO: 1 or SEQ ID: 2, or an amino acid sequence 95% identical thereto.

In various embodiments, the transduced immune effector cells are intravenously administered to the subject.

In particular embodiments, the treatment paradigms contemplated herein comprise repeating any one or more of the treatment steps one, two, three, four, five, or more times.

In various embodiments, a method of treating a subject that has cancer comprises: intra-tumorially administering to a solid cancer in the subject, an effective amount of a pseudotyped oncolytic HSV-1 comprising: a polynucleotide encoding a target antigen selected from the group consisting of CD19 and BCMA; a polynucleotide encoding human MMP-9 inserted into a non-essential viral gene and/or deleted joint region; and one or more tumor suppressor miR target sequences recognized and/or bound by a miR selected from the group consisting of hsa-miR-1-3p, hsa-miR-124-3p, hsa-miR-143-3p, hsa-miR-145-5p, hsa-miR-451a, and hsa-miR-559 inserted into one or more essential viral genes required for viral replication selected from the group consisting of ICP4 and ICP27; isolating immune effector cells from the subject about 1 week to about 4 weeks after administering the oncolytic HSV-1; transducing the immune effector cells with retroviral or lentiviral vector encoding an anti-CD19 CAR or anti-BCMA CAR; and administering the transduced immune effector cells to the subject; and optionally repeating the viral administration and immune effector cell administration steps.

In various embodiments, a method of treating a subject that has cancer comprises: intra-tumorially administering to a solid cancer in the subject, an effective amount of a pseudotyped oncolytic HSV-1 comprising: a polynucleotide encoding a target antigen selected from the group consisting of CD19 and BCMA; a polynucleotide encoding human MMP-9 inserted into a non-essential viral gene and/or deleted joint region; and one or more tumor suppressor miR target sequences recognized and/or bound by a miR selected from the group consisting of hsa-miR-1-3p, hsa-miR-124-3p, hsa-miR-143-3p, hsa-miR-145-5p, hsa-miR-451a, and hsa-miR-559 inserted into one or more essential viral genes required for viral replication selected from the group consisting of ICP4 and ICP27; wherein the HSV-1 further comprises one or more modified non-essential viral genes selected from the group consisting of one or more copies of the ICP34.5 gene, the ICP6 gene, and the ICP47 gene; isolating immune effector cells from the subject about 1 week to about 4 weeks after administering the oncolytic HSV-1; transducing the immune effector cells with retroviral or lentiviral vector encoding an anti-CD19 CAR or anti-BCMA CAR; and administering the transduced immune effector cells to the subject; and optionally repeating the viral and CAR T cell administration steps.

In various embodiments, a method of treating a subject that has cancer comprises: intra-tumorially administering to a solid cancer in the subject, an effective amount of a pseudotyped oncolytic HSV-1 comprising: a polynucleotide encoding a target antigen selected from the group consisting of CD19 and BCMA; a polynucleotide encoding human MMP-9 inserted into a non-essential viral gene and/or deleted joint region; and one or more tumor suppressor miR target sequences recognized and/or bound by a miR selected from the group consisting of hsa-miR-1-3p, hsa-miR-124-3p, hsa-miR-143-3p, hsa-miR-145-5p, hsa-miR-451a, and hsa-miR-559 inserted into one or more essential viral genes required for viral replication selected from the group consisting of ICP4 and ICP27; wherein the HSV-1 further comprises one or more modified non-essential viral genes selected from the group consisting of one or more copies of the ICP34.5 gene, the ICP6 gene, and the ICP47 gene; and wherein the HSV-1 further comprises a gB:NT mutation, and optionally a gH:KV mutation; isolating immune effector cells from the subject about 1 week to about 4 weeks after administering the oncolytic HSV-1; transducing the immune effector cells with retroviral or lentiviral vector encoding an anti-CD19 CAR or anti-BCMA CAR; and administering the transduced immune effector cells to the subject; and optionally repeating the viral administration and CAR T cell administration steps.

BRIEF DESCRIPTION OF SEVERAL VIEWS OF THE DRAWINGS

The FIGURE shows a cartoon of an exemplary treatment paradigm contemplated herein. A subject is treated with an oncolytic virus, immune effector cells are harvested from the subject, harvested immune effector cells are transduced with an engineered antigen receptor, transduced immune effector cells are cultured and administered to the subject.

BRIEF DESCRIPTION OF THE SEQUENCE IDENTIFIERS

SEQ ID NO: 1 sets forth the polypeptide sequence for an anti-BCMA CAR.

SEQ ID NO: 2 sets forth the polypeptide sequence for an anti-CD19 CAR.

SEQ ID NOs: 3-13 set forth the amino acid sequences of various linkers.

SEQ ID NOs: 14-38 set forth the amino acid sequences of protease cleavage sites and self-cleaving polypeptide cleavage sites.

DETAILED DESCRIPTION

A. Overview

Cancers are often heterogeneous pools of cells expressing different levels of various antigens. Ideally, adoptive cellular therapies (ACT) are initially selected to target an antigen that is expressed on a majority of cancer cells and that substantially lacks expression on normal cells. An effective targeted immunotherapy will kill the majority of cancer cells that express the target antigen, resulting in partial or complete remission. However, the reality is that there is a dearth of available targets antigens specifically expressed on the majority of cells in a cancer but that are not expressed in or on normal cells.

Solid cancers can be especially heterogeneous in nature, with the cells in the core of the cancer expressing very different target antigens than cells at the tumor periphery. For example, peripheral cancer cells in a tumor may uniformly express a target antigen but the remaining cancer cells may not express the antigen or may express such low levels that these cancer cells are spared and give rise to cancer cells that are not effectively targeted or that are resistant to the initial immunotherapy. In addition, the more central cells of a cancerous tumor may not be accessible to an immunotherapy, leading to additional tumor outgrowth and resistance. Moreover, an immunosuppressive tumor microenvironment, which is often associated with solid cancers, leads to T cell exhaustion and further decreases the durability, persistence, and efficacy of adoptive cellular therapy. These obstacles highlight the fact that the promise of using CAR T immunotherapies to treat solid cancers has yet to be realized.

The present invention provides solutions to these and other problems plaguing the art in the treatment of solid tumors.

In various embodiments, a method of treating a subject that has cancer is provided.

In particular embodiments, a subject is administered an oncolytic virus that paints cancer cells, but not normal cells, with a target antigen. Without wishing to be bound by any particular theory, it is contemplated that an oncolytic virus that selective replicates in cancer cells and expresses a target antigen that is not normally expressed or that is expressed at low levels on the cancer cells, and that is not expressed on the majority of normal cells, will allow efficient targeting with an adoptive cellular therapy, including but not limited to immune effector cells expressing an engineered antigen receptor that recognizes and binds the target antigen.

In particular embodiments, a subject is administered an oncolytic virus comprising a target antigen to paint cancer cells, and that selectively or specifically replicates in cancer cells but not normal cells. In particular embodiments, the virus contains one or more microRNA (miR) target sites recognized in normal cells but not cancer cells; the one or more miR target sites are inserted into one or more viral genes essential for viral replication. Without wishing to be bound by any particular theory, it is contemplated that miRs specifically expressed or selectively expressed in normal cells will bind to miR target sites in the mRNAs encoding proteins essential to viral replication, prevent their translation, and thereby prevent viral replication in normal cells infected by the virus. In contrast, cancer cells being targeted for treatment will not express the miRs that recognize the miR target sites inserted into the viral genes essential for viral replication, thereby enabling viral replication, expression of the target antigen, and/or oncolysis in the infected cells.

In certain embodiments, a subject is administered an oncolytic virus that selectively or specifically replicates in cancer cells but not normal cells and that comprises a target antigen to paint cancer cells, and a therapeutic polypeptide. Without wishing to be bound by any particular theory, it is contemplated that cancer cells infected with the virus will express target antigen and therapeutic polypeptide. In some embodiments, the therapeutic polypeptide is an extracellular matrix remodeling enzyme that will increase virus spreading and targeting of adjacent cancer cells and/or an immunostimulatory cytokine and/or a checkpoint inhibitor. Cancer cells that do not undergo viral lysis will express the target antigen and be lysed by immune effector cells redirected to recognize and bind the target antigen. In certain embodiments, expression of immunostimulatory polypeptides that combat the immunosuppressive signals for the tumor microenvironment further enhance the efficacy of the compositions and methods of treatment contemplated herein.

In particular embodiments, a method of treating a subject in need thereof comprises administering an effective amount of an oncolytic virus (e.g., HSV-1) that encodes a target antigen, one or more therapeutic polypeptides, and one or more miR target sequences, recognized and/or bound by one or more miRs specifically expressed or selectively expressed in normal cells but not the cancer cells being targeted, inserted into one or more essential viral genes required for viral replication; isolating immune effector cells from the subject; expressing an engineered antigen receptor that recognizes and/or binds the target antigen in the isolated immune effector cells; and administering the transduced immune effector cells to the subject. The methods contemplated herein may be repeated one, two, three, four, five, or more times, if needed or desired.

Techniques for recombinant (i.e., engineered) DNA, peptide and oligonucleotide synthesis, immunoassays, tissue culture, transformation (e.g., electroporation, lipofection), enzymatic reactions, purification and related techniques and procedures may be generally performed as described in various general and more specific references in microbiology, molecular biology, biochemistry, molecular genetics, cell biology, virology and immunology as cited and discussed throughout the present specification. See, e.g., Sambrook et al., *Molecular Cloning: A Laboratory Manual*, 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid The Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols (Methods in Molecular Biology)* (Park, Ed., 3rd Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); Handbook Of Experimental Immunology, Volumes I-IV (D. M. Weir and C C Blackwell, eds., 1986); Roitt, *Essential Immunology*, 6th Edition, (Blackwell Scientific Publications, Oxford, 1988); *Current Protocols in Immunology* (Q. E. Coligan, A. M. Kruisbeek, D. H. Margulies, E. M. Shevach and W. Strober, eds., 1991); *Annual Review of Immunology*; as well as monographs in journals such as Advances in Immunology.

B. Definitions

Prior to setting forth this disclosure in more detail, it may be helpful to an understanding thereof to provide definitions of certain terms to be used herein.

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below. Additional definitions are set forth throughout this disclosure.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

In one embodiment, a range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

An "antigen (Ag)" refers to a compound, composition, or substance that can stimulate the production of antibodies or a T cell response in an animal, including compositions (such as one that includes a cancer-specific protein) that are injected or absorbed into an animal. Exemplary antigens include but are not limited to lipids, carbohydrates, polysaccharides, glycoproteins, peptides, or nucleic acids. An antigen reacts with the products of specific humoral or cellular immunity, including those induced by heterologous antigens, such as the disclosed antigens.

An "epitope" or "antigenic determinant" refers to the region of an antigen to which a binding domain binds.

As used herein, the terms, "binding domain," "extracellular domain," "antigen binding domain," "extracellular binding domain," "extracellular antigen binding domain," "antigen-specific binding domain," and "extracellular antigen specific binding domain," are used interchangeably and provide a polypeptide including, but not limited to antibodies, antigen binding fragments thereof, and engineered antigen receptors, with the ability to specifically bind or selectively bind to the target antigen. The binding domain may be derived either from a natural, synthetic, semi-synthetic, or recombinant source.

The terms "specific binding affinity" or "specifically binds" or "specifically bound" or "specific binding" or "specifically targets" as used herein, describe binding of binding domain to a target antigen at greater binding affinity than background binding. A binding domain "specifically binds" to a target antigen, if it binds to or associates with the antigen with an affinity or $K_a$ (i.e., an equilibrium association constant of a particular binding interaction with units of 1/M) of, for example, greater than or equal to about $10^5$ $M^{-1}$. In certain embodiments, a binding domain (or a fusion protein comprising the same) binds to a target with a $K_a$ greater than or equal to about $10^6$ $M^{-1}$, $10^7$ $M^{-1}$, $10^8$ $M^{-1}$, $10^9$ $M^{-1}$, $10^{10}$ $M^{-1}$, $10^{11}$ $M^1$, $10^{12}$ $M^{-1}$, or $10^{13}$ $M^{-1}$. "High affinity" binding domains (or single chain fusion proteins thereof) refer to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, at least $10^{13}$ $M^{-1}$, or greater.

Alternatively, affinity may be defined as an equilibrium dissociation constant ($K_d$) of a particular binding interaction with units of M (e.g., $10^{-5}$ M to $10^{-13}$ M, or less). Affinities of binding domain polypeptides can be readily determined using conventional techniques, e.g., by competitive ELISA (enzyme-linked immunosorbent assay), or by binding association, or displacement assays using labeled ligands, or using a surface-plasmon resonance device such as the Biacore T100, which is available from Biacore, Inc., Piscataway, NJ, or optical biosensor technology such as the EPIC system or EnSpire that are available from Corning and Perkin Elmer respectively (see also, e.g., Scatchard et al. (1949) Ann. N.Y. Acad. Sci. 51:660; and U.S. Pat. Nos. 5,283,173; 5,468,614, or the equivalent).

In one embodiment, the affinity of specific binding is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

The terms "selectively binds" or "selectively bound" or "selectively binding" or "selectively targets" and describe preferential binding of one molecule to a target molecule (on-target binding) in the presence of a plurality of off-target molecules. In particular embodiments, a microRNA (miR) selectively binds to an on-target miR target site about 5, 10, 15, 20, 25, 50, 100, or 1000 times more frequently than the miR binds an off-target DNA target binding site.

"On-target" refers to a target site sequence.

"Off-target" refers to a sequence similar to but not identical to a target site sequence.

A "target site" or "target sequence" is a nucleic acid sequence that defines a portion of a nucleic acid to which a binding molecule will bind and/or cleave, provided sufficient conditions for binding and/or cleavage exist. In particular embodiments, a target site is an miR target site. In particular embodiments, a target site is an endonuclease target site. Target sites may be single-stranded or double-stranded. When referring to a polynucleotide sequence or SEQ ID NO. that references only one strand of a double-stranded target site or target sequence, it would be understood that the target site or target sequence comprises the reference sequence and its complement.

An "antibody" refers to a binding domain that is a polypeptide comprising at least a light chain or heavy chain immunoglobulin variable region which specifically recognizes and binds an epitope of an antigen, such as a lipid, carbohydrate, polysaccharide, glycoprotein, peptide, or nucleic acid containing an antigenic determinant, such as those recognized by an immune cell.

Antibodies include antigen binding fragments thereof, such as Camel Ig, Ig NAR, Fab fragments, Fab' fragments, F(ab)'$_2$ fragments, F(ab)'$_3$ fragments, Fv, single chain variable fragments ("scFv"), bis-scFv, (scFv)$_2$, minibodies, diabodies, triabodies, tetrabodies, disulfide stabilized Fv proteins ("dsFv"), and single-domain antibody (sdAb, Nanobody) and portions of full length antibodies responsible for antigen binding. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, IL); Kuby, J., Immunology, 3rd Ed., W. H. Freeman & Co., New York, 1997; Kozbor J. Immunol., 133: 3001 (1984); Brodeur et al., Monoclonal Antibody Production Techniques and Applications, pp. 51-63 (Marcel Dekker, Inc., New York, 1987); Boerner et al., J. Immunol., 147: 86 (1991); Jakobovits et al., PNAS USA, 90: 2551 (1993); Jakobovits et al., Nature, 362: 255 (1993); Bruggermann et al., Year in Immunol., 7: 33 (1993); U.S. Pat. No. 5,585,089; Koch-Nolte, et al, FASEB J., 21: 3490-3498 (2007); Riechmann L. et al, J. Immunol. Methods 231:25-38 (1999); WO94/04678; WO94/25591; U.S. Pat. No. 6,005,079; EP 404,097; WO 1993/01161; Hudson et al., Nat. Med. 9:129-134 (2003); Hollinger et al., PNAS USA 90: 6444-6448 (1993); Holt, L., et al, Trends in Biotechnology, 21(11): 484-490; and Pluckthun, in The Pharmacology of Monoclonal Antibodies, vol. 113, Rosenburg and Moore eds., (Springer-Verlag, New York, 1994), pp. 269-315.

By "enhance" or "promote," or "increase" or "expand" refers generally to the ability of a composition contemplated herein to produce, elicit, or cause a greater physiological response (i.e., downstream effects) compared to the response caused by either vehicle or a control molecule/composition. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. A "decrease" or "reduced" amount is typically a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response (reference response) produced by vehicle or a control composition.

By "maintain," or "preserve," or "maintenance," or "no change," or "no substantial change," or "no substantial decrease" refers generally to the ability of a composition contemplated herein to produce, elicit, or cause a substantially similar or comparable physiological response (i.e., downstream effects), as compared to the response caused by either vehicle or a control molecule/composition. A comparable response is one that is not significantly different or measurable different from the reference response.

The term "ex vivo" refers generally to activities that take place outside an organism, such as experimentation or measurements done in or on living tissue in an artificial environment outside the organism, preferably with minimum alteration of the natural conditions.

The term "in vivo" refers generally to activities that take place inside an organism.

An "exogenous" molecule is a molecule that is not normally present in a cell, but that is introduced into a cell by one or more genetic, biochemical or other methods. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, biopolymer nanoparticle, calcium phosphate co-precipitation, DEAE-dextran-mediated transfer and viral vector-mediated transfer.

An "endogenous" molecule is one that is normally present in a particular cell at a particular stage under particular environmental conditions.

A "gene," refers to a DNA region encoding a gene product, as well as all DNA regions which regulate the production of the gene product, whether or not such regulatory sequences are adjacent to coding and/or transcribed sequences. A gene includes, but is not limited to, promoter sequences, enhancers, exons, introns, silencers, insulators, boundary elements, terminators, polyadenylation sequences, post-transcription response elements, translational regulatory sequences such as ribosome binding sites and internal ribosome entry sites, replication origins, matrix attachment sites, and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA.

As used herein, the term "genetically engineered" or "genetically modified" refers to the addition of extra genetic material in the form of DNA or RNA to the total genetic material of a genome. Genetic modifications may be targeted or non-targeted to a particular site in a genome.

In one embodiment, genetic modification is site specific. In one embodiment, genetic modification is not site specific.

As used herein, the term "genome editing" refers to the substitution, deletion, and/or introduction of genetic material at a target site in a genome, which restores, corrects, disrupts, and/or modifies expression of a gene or gene product.

As used herein, the term "gene therapy" refers to the introduction of extra genetic material into the total genetic material in a genome that restores, corrects, or modifies expression of a gene or gene product, or for the purpose of expressing a therapeutic polypeptide.

An "immune disorder" refers to a disease that evokes a response from the immune system. In particular embodiments, the term "immune disorder" refers to a cancer, graft-versus-host disease, an autoimmune disease, or an immunodeficiency. In one embodiment, immune disorders encompasses infectious disease.

As used herein, the term "cancer" relates generally to a class of diseases or conditions in which abnormal cells divide without control and can invade nearby tissues.

As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood).

As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancers form tumors, but some, e.g., leukemia, do not necessarily form tumors. For those cancers that form tumors, the terms cancer (cell) and tumor (cell) are used interchangeably. The amount of a tumor in an individual is the "tumor burden" which can be measured as the number, volume, or weight of the tumor.

The term "relapse" refers to the diagnosis of return, or signs and symptoms of return, of a cancer after a period of improvement or remission.

"Remission," is also referred to as "clinical remission," and includes both partial and complete remission. In partial remission, some, but not all, signs and symptoms of cancer have disappeared. In complete remission, all signs and symptoms of cancer have disappeared, although cancer still may be in the body.

"Refractory" refers to a cancer that is resistant to, or non-responsive to, therapy with a particular therapeutic agent. A cancer can be refractory from the onset of treatment (i.e., non-responsive to initial exposure to the therapeutic agent), or as a result of developing resistance to the therapeutic agent, either over the course of a first treatment period or during a subsequent treatment period.

"Antigen negative" refers to a cell that does not express antigen or expresses a negligible amount of antigen that is undetectable. In one embodiment, antigen negative cells do not bind receptors directed to the antigen. In one embodiment, antigen negative cells do not substantially bind receptors directed to the antigen. In one embodiment, an antigen negative cell is a target cell. In another embodiment, an antigen negative cell is a non-target cell.

As used herein, the terms "individual" and "subject" are often used interchangeably and refer to any animal that has cancer that can be treated with the compositions and methods contemplated elsewhere herein. Suitable subjects (e.g., patients) include laboratory animals (such as mouse, rat, rabbit, or guinea pig), farm animals, and domestic animals or pets (such as a cat or dog). Non-human primates and, preferably, human subjects, are included. Typical subjects "in need thereof" include human patients that have, have been diagnosed with, or are at risk of having a cancer.

As used herein, the term "patient" refers to a subject that has been diagnosed with a cancer that can be treated with the compositions and methods contemplated elsewhere herein.

As used herein "treat" or "treatment" or "treating," includes any beneficial or desirable effect on the symptoms or pathology of a cancer, and may include even minimal reductions in one or more measurable markers of the cancer. Treatment can optionally involve delaying of the progression of the cancer, e.g., delaying tumor outgrowth. "Treatment" does not necessarily indicate complete eradication or cure of the cancer, or associated symptoms thereof.

As used herein, "prevent," and similar words such as "prevention," "prevented," "preventing" etc., indicate an approach for preventing, inhibiting, or reducing the likelihood of the occurrence or recurrence of, a cancer. It also refers to delaying the onset or recurrence of a cancer or delaying the occurrence or recurrence of the symptoms of a cancer. As used herein, "prevention" and similar words also includes reducing the intensity, effect, symptoms and/or burden of a cancer prior to onset or recurrence of the cancer.

As used herein, the phrase "ameliorating at least one symptom of" refers to decreasing one or more symptoms of a cancer for which the subject is being treated. In particular embodiments, the one or more symptoms ameliorated include, but are not limited to, weakness, fatigue, shortness of breath, easy bruising and bleeding, frequent infections, enlarged lymph nodes, distended or painful abdomen (due to enlarged abdominal organs), bone or joint pain, fractures, unplanned weight loss, poor appetite, night sweats, persistent mild fever, and decreased urination (due to impaired kidney function).

As used herein, the term "amount" refers to "an amount effective" or "an effective amount" of an oncolytic virus, modified immune effector cell, or compositions comprising the same, sufficient to achieve a beneficial or desired prophylactic or therapeutic result, including clinical results.

A "prophylactically effective amount" refers to an amount of an oncolytic virus, modified immune effector cell, or compositions comprising the same, sufficient to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of an oncolytic virus, modified immune effector cell, or compositions comprising the same may vary according to factors such as the disease state, age, sex, and weight of the individual, and the ability to elicit a desired response in the individual. A therapeutically effective amount is also one in which any toxic or detrimental effects are outweighed by the therapeutically beneficial effects. The term "therapeutically effective amount" includes an amount that is effective to "treat" a subject (e.g., a patient). When a therapeutic amount is indicated, the precise amount of the compositions contemplated in particular embodiments, to be administered, can be determined by a physician in view of the specification and with consideration of individual differences in age, weight, tumor size, extent of infection or metastasis, and condition of the patient (subject).

C. Oncolytic Viruses

The present disclosure contemplates, in particular embodiments, a recombinant oncolytic virus that encodes one or more target antigens, one or more microRNA (miR) target sequences, and optionally, one or more therapeutic polypeptides. An "oncolytic virus" refers to a virus that has been modified to, or that naturally, preferentially infects cancer cells. Illustrative examples of an oncolytic virus suitable for use in particular embodiments contemplated herein include, but are not limited to an adenovirus, a coxsackievirus, a herpes simplex virus (HSV), a maraba virus, a measles virus, an orthomyxovirus, a parvovirus, a polio virus, a vaccinia virus, or a vesicular stomatitis virus.

In particular embodiments, a virus is referred to as a "vector" or "viral vector." The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. The terms "oncolytic virus" and "oncolytic vector" are used interchangeably in particular embodiments. In particular embodiments, an oncolytic vector is a Herpes simplex virus (HSV). In particular preferred embodiments, the HSV is HSV-1. In particular embodiments, the oncolytic HSV-1 is capable of tumor-selective or tumor-specific vector replication and lysis.

An oncolytic HSV-1 may be advantageous in particular embodiments, because not only can the oncolytic HSV-1 be engineered to specifically or selectively replicate in cancer cells, but the HSV-1 vector can also be engineered to accommodate one or more expression cassettes encoding one or more target antigens and one or more therapeutic polypeptides.

The mature HSV-1 virion consists of an enveloped icosahedral capsid with a viral genome consisting of a linear double-stranded DNA molecule that is 152 kb and encodes approximately 85 genes. The linear double-stranded genome is composed of a long (UL) and short (US) genomic segment that contain both essential and non-essential viral genes. HSV-1 accessory genes include ICP-34.5 (734.5), ICP0, LAT, UL2, UL3, UL4, UL10, UL11, UL13, UL16, UL20, UL21, UL29, UL34, UL39 (ICP6), UL40, UL41, UL43, UL 44, UL45, UL46, UL47, UL50, UL51, UL55, UL56, US1 (ICP22), US2, US3, US4, US5, US7, US8, US9, US10, US11, and US12 (ICP47, α47). Essential HSV-1 genes include UL1, UL5, UL6, UL7, UL8, UL9, UL12, UL14, UL15, UL17, UL18, UL19, UL22, UL23, UL24, UL25, UL2, UL27, UL28, UL29, UL30, UL31, UL32, UL33, UL35, UL36, UL37, UL38, UL42, UL48, UL49, UL52, UL53, UL54 (ICP27), ICP4, and US6.

Each genomic segment is flanked by inverted repeats creating an internal region referred to as the joint region. Several genes that regulate virus replication are located in repeat regions and are therefore diploid. The joint region includes a single copy of ICP-34.5 (γ34.5), ICP0, LAT, and ICP4. Consequently, the approximately 19 kb joint region can be deleted without substantially compromising virus replication, creating a large space for insertion of one or more expression cassettes.

In general, deletion of one or more accessory genes results in replication competent, but in some cases attenuated, viral vectors. By contrast, deletion of any essential gene completely blocks viral replication and therefore productive viral infection.

In particular embodiments, an oncolytic HSV-1 encodes one or more target antigens, one or more microRNA (miR) target sequences, and optionally, one or more therapeutic polypeptides and further comprises deletion or modification of one or more viral accessory genes.

In particular embodiments an oncolytic virus comprises a modification and/or deletion of one or more accessory genes or gene regions (e.g., the joint region) or portions thereof to attenuate the viral vector in normal cells. Illustrative examples of accessory viral genes or gene regions that can be modified and/or deleted in particular embodiments include, one or more of: the joint region, one or both copies of ICP-34.5, one or both copies of ICP0, one or both copies of LAT, UL2, UL3, UL4, UL10, UL11, UL13, UL16, UL20, UL21, UL29, UL34, UL39 (ICP6), UL40, UL41, UL43, UL 44, UL45, UL46, UL47, UL50, UL51, UL55, UL56, US1 (ICP22), US2, US3, US4, US5, US7, US8, US9, US10, US11, and US12 (ICP47, α47). Any one or more of the modified or deleted loci may be replaced with an expression cassette or polynucleotide encoding a therapeutic polypeptide contemplated herein.

In particular embodiments, an oncolytic virus comprises a modification and/or deletion of the joint region, one or both copies of ICP-34.5, UL39 (ICP6), and/or US12 (ICP47, α47). In particular embodiments, an oncolytic virus comprises a modification and/or deletion of the joint region, both copies of ICP-34.5, UL39 (ICP6), and US12 (ICP47, α47). In particular preferred embodiments, an oncolytic virus comprises a modification and/or deletion of the joint region, one or both copies of ICP-34.5, and US12 (ICP47, α47). In particular preferred embodiments, an oncolytic virus comprises a modification and/or deletion of one or both copies of ICP-34.5, and US12 (ICP47, α47). In particular preferred embodiments, an oncolytic virus comprises a modification and/or deletion of the joint region, both copies of ICP-34.5 and US12 (ICP47, α47). In particular preferred embodiments, an oncolytic virus comprises a modification and/or deletion of both copies of ICP-34.5 and US12 (ICP47, α47). In a particular preferred embodiment, an oncolytic virus comprises a modification and/or deletion of the joint region.

Any one or more of the modified or deleted loci may be replaced with an expression cassette or polynucleotide encoding a therapeutic polypeptide contemplated herein.

In various embodiments, an oncolytic virus contemplated herein does not comprise a deletion of one or more viral accessory genes and comprises one or more expression cassettes or polynucleotides encoding a therapeutic polypeptide inserted between viral accessory genes, between a viral accessory gene and an essential viral gene, or between essential viral genes, such that normal expression of the viral genes is not substantially disrupted, decreased, or increased.

In various embodiments, an oncolytic virus contemplated herein comprises a deletion or modification of the joint region, but does not comprise a deletion of all copies of viral accessory genes and further comprises one or more expression cassettes or polynucleotides encoding a therapeutic polypeptide inserted between viral accessory genes, between a viral accessory gene and an essential viral gene, between essential viral genes, or in the modified or deleted joint region, such that normal expression of all copies of viral genes are not substantially disrupted, decreased, or increased.

Some oncolytic virus genomes are very large and can be modified to accommodate transgenes or expression cassettes. In particular, insertion of one or more therapeutic transgenes or polynucleotides encoding a therapeutic gene can be incorporated into the HSV-1 genome to enhance the efficacy of the compositions and methods contemplated herein.

In particular embodiments, the therapeutic polypeptide is a bispecific T cell engager (BiTE), a checkpoint inhibitor, a cytokine, a protease, or an extracellular matrix remodeling enzyme.

BiTE molecules are bipartite molecules comprising a first binding domain that binds a target antigen, a linker or spacer as contemplated elsewhere herein, and a second binding domain that binds a stimulatory or costimulatory molecule on an immune effector cell. The first and second binding domains may be independently selected from ligands, receptors, antibodies or antigen binding fragments thereof, lectins, and carbohydrates.

In particular embodiments, the first and second binding domains are antigen binding domains.

In particular embodiments, the first and second binding domains are antibodies or antigen binding fragments thereof. In one embodiment, the first and second binding domains are single chain variable fragments (scFv).

Illustrative examples of target antigens that may be recognized and bound by the first binding domain in particular embodiments include, but are not limited to: alpha folate receptor (FRα), $α_vβ_6$ integrin, B cell maturation antigen (BCMA), B7-H3 (CD276), B7-H6, carbonic anhydrase IX (CAIX), CD16, CD19, CD20, CD22, CD30, CD33, CD37, CD38, CD44, CD44v6, CD44v7/8, CD70, CD79a, CD79b, CD123, CD133, CD138, CD171, carcinoembryonic antigen (CEA), C-type lectin-like molecule-1 (CLL-1), CD2 subset 1 (CS-1), chondroitin sulfate proteoglycan 4 (CSPG4), cutaneous T cell lymphoma-associated antigen 1 (CTAGE1), epidermal growth factor receptor (EGFR), epidermal growth factor receptor variant III (EGFRvIII), epithelial glycoprotein 2 (EGP2), epithelial glycoprotein 40 (EGP40), epithelial cell adhesion molecule (EPCAM), ephrin type-A receptor 2 (EPHA2), fibroblast activation protein (FAP), Fc Receptor Like 5 (FCRL5), fetal acetylcholinesterase receptor (AchR), ganglioside G2 (GD2), ganglioside G3 (GD3), Glypican-3 (GPC3), EGFR family including ErbB2 (HER2), IL-11Rα, IL-13Rα2, Kappa, cancer/testis antigen 2 (LAGE-1A), Lambda, Lewis-Y (LeY), L1 cell adhesion molecule (L1-CAM), melanoma antigen gene (MAGE)-A1, MAGE-A3, MAGE-A4, MAGE-A6, MAGEA10, melanoma antigen recognized by T cells 1 (MelanA or MART1), Mesothelin (MSLN), MUC1, MUC16, MHC class I chain related proteins A (MICA), MHC class I chain related proteins B (MICB), neural cell adhesion molecule (NCAM), cancer/testis antigen 1 (NY-ESO-1), polysialic acid; placenta-specific 1 (PLAC1), preferentially expressed antigen in melanoma (PRAME), prostate stem cell antigen (PSCA), prostate-specific membrane antigen (PSMA), receptor tyrosine kinase-like orphan receptor 1 (ROR1), synovial sarcoma, X breakpoint 2 (SSX2), Survivin, tumor associated glycoprotein 72 (TAG72), tumor endothelial marker 1 (TEM1/CD248), tumor endothelial marker 7-related (TEM7R), trophoblast glycoprotein (TPBG), UL16-binding protein (ULBP) 1, ULBP2, ULBP3, ULBP4, ULBP5, ULBP6, vascular endothelial growth factor receptor 2 (VEGFR2), and Wilms tumor 1 (WT-1).

In particular embodiments, a BiTE comprises scFvs that bind CD19 and CD3 (CD19/CD3 BiTE), scFvs that bind CD20 and CD3 (CD20/CD3 BiTE), scFvs that bind CD22 and CD3 (CD22/CD3 BiTE), scFvs that bind CD38 and CD3 (CD38/CD3 BiTE), scFvs that bind BCMA and CD3 (BCMA/CD3 BiTE), scFvs that bind FAP and CD3 (FAP/CD3 BiTE), scFvs that bind PD-L1 and CD3 (PD-L1/CD3 BiTE), or scFvs that bind PD-L2 and CD3 (PD-L2/CD3 BiTE).

In one embodiment, a therapeutic polypeptide is a checkpoint inhibitor. Checkpoint inhibitors can be used to block or squelch the immunosuppressive signals mediated by the tumor microenvironment. In particular embodiments, the checkpoint inhibitor is an antibody or antigen binding domain thereof that binds to and reduces or decreases signaling of a checkpoint protein selected from the group consisting of: PD-L1, PD-L2, PD-1, LAG-3, TIM-3, CTLA-4, TIGIT, TGFβ, and TGFβR.

In one embodiment, a therapeutic polypeptide is an immunostimulatory cytokine. Inflammatory cytokines may be preferred transgenes in particular embodiments because they contribute to anti-tumor immune cell function and target cell cytolysis. In particular embodiments, the immunostimulatory cytokine is selected from the group consisting of: IL-2, insulin, IFN-γ, IL-7, IL-21, IL-10, IL-12, IL-15, and TNF-α.

In one embodiment, a therapeutic polypeptide is a protease or an extracellular matrix remodeling enzyme. In particular embodiments, the protease is selected from the group consisting of: a cathepsin, a kallikrein, and a serine protease.

In a preferred embodiment, a therapeutic polypeptide is an extracellular matrix remodeling enzyme. Many cells within a tumor are generally inaccessible to immune effector cells. Remodeling the tumor microenvironment can create more immune effector cell access to tumor cells. In particular preferred embodiments, the extracellular matrix remodeling enzyme is a matrix metalloproteinase (MMP) or a disintegrin metalloproteinase (ADAM).

In a particular embodiment, the extracellular matrix remodeling enzyme is selected from the group consisting of: MMP-1, MMP-2, MMP-3, MMP-7, MMP-8, MMP-9, MMP-10, MMP-11. MMP-12, MMP-13, MMP-14, MMP-15, MMP-16, MMP-17, MMP-18, MMP-19, MMP-20, MMP-21, MMP-23A, MMP-23B, MMP-24, MMP-25, MMP-26, MMP-27, and MMP-28.

In a particular preferred embodiment, the extracellular matrix remodeling enzyme is MMP-9.

Entry of HSV-1 into susceptible cells involves the coordinated activities of at least five viral envelope glycoproteins gB, gC, gD, gH, and gL. Glycoproteins in the HSV-1 viral capsid may be modified and/or deleted to increase or enhance virus entry into a host cell, virus spreading, and targeting to target cells, e.g., cancer cells. In some instances, it may be advantageous to increase or enhance virus entry into the target cell. In some instances, it may be advantageous to increase virus spreading among target cells to increase the number of cells infected. In some instances, it may be advantageous to pseudotype an oncolytic virus by replacing a portion of gC and/or gD with a polypeptide that binds to a target cell. The terms "pseudotype" or "pseudotyping" as used herein, refer to a virus whose viral envelope proteins have been substituted with those of another virus or another polypeptide possessing preferable target cell binding characteristics.

In particular embodiments, an oncolytic HSV-1 encodes one or more target antigens, one or more miR target sequences, and optionally, one or more therapeutic polypeptides and further comprises deletion or modification of one or more viral accessory genes and modifications of one or more glycoproteins that enhance virus entry into a host cell, virus spreading, and targeting to a target cell.

In a particular embodiment, a gB gene can be modified in an oncolytic HSV-1 to increase viral entry into a cell. In a preferred aspect, the gB gene of an oncolytic HSV-1 is modified to express a gB:NT glycoprotein comprising D285N/A549T mutations that increase viral entry. In a certain embodiment, a gH gene can be modified in an oncolytic HSV-1 to increase the spreading of virus among a population of cells. In a preferred aspect, the gH gene of an oncolytic HSV-1 is modified to express a gH:KV glycoprotein comprising N753K/A778V mutations that increase viral spread. In another particular embodiment, an oncolytic HSV-1 is modified to express both gB:NT and gH:KV glycoproteins.

In various embodiments, a gC and/or gD gene can be modified and/or partially deleted to express a non-HSV polypeptide that binds to a target cell. In one embodiment, a non-HSV polypeptide inserted into the gD gene, replacing residues 2 to 24 of the gD gene. In a particular embodiment, a non-HSV polypeptide inserted into the gD gene, replacing residues 2 to 24 of the gD gene and the gD comprises a Y38C mutation.

In preferred embodiments, the non-HSV polypeptide is a ligand that specifically or selectively binds a protein on the surface of the target cell.

Illustrative examples of ligands that specifically or selectively binds a protein on the surface of the target cell and that are suitable for expressing in an oncolytic HSV-1 contemplated in particular embodiments include, but are not limited to antibodies or antigen binding fragments thereof, hormone, growth factors, or other members of ligand:receptor pairs.

In particular embodiments, the ligand is an antibody or antigen binding fragment thereof selected from the group consisting of: a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody).

In particular embodiments, ligand is a polypeptide that binds a growth factor receptor expressed on a target cell. In particular embodiments, the growth factor receptor is selected from the group consisting of: an epidermal growth factor receptor (EGFR) or splice variant thereof, ERBB2 (HER), ERBB3, ERBB4, insulin growth factor 1 receptor (IGF1R), IGF2R, TGFβ receptor (TGFβR)1, TGFβR2, vascular endothelial growth factor receptor (VEGFR)1, VEGFR2, VEGFR3, platelet derived growth factor receptor (PDGFR)α, PDGFRβ, fibroblast growth factor receptor (FGFR)1, FGFR2, FGFR3, FGFR4, and the like.

In particular embodiments, ligand is an antibody or antigen binding fragment thereof that binds a checkpoint protein expressed on a target cell. In particular embodiments, the checkpoint protein is selected from the group consisting of: programmed death ligand 1 (PD-L1), and programmed death ligand 2 (PD-L2).

In a particular embodiment, a pseudotyped oncolytic HSV-1 is provided comprising: a polynucleotide encoding a target antigen selected from the group consisting of CD19 and BCMA; a polynucleotide encoding human MMP-9 inserted into a non-essential viral gene and/or deleted joint region; and one or more tumor suppressor miR target sequences recognized and/or bound by a miR selected from the group consisting of miR-1-3p, miR-124-3p, miR-143-3p, miR-145-5p, miR-451a, and miR-559 inserted into one or more essential viral genes required for viral replication selected from the group consisting of ICP4 and ICP27.

In a particular embodiment, a pseudotyped oncolytic HSV-1 is provided comprising: a polynucleotide encoding a target antigen selected from the group consisting of CD19 and BCMA; a polynucleotide encoding human MMP-9 inserted into a non-essential viral gene and/or deleted joint region; and one or more tumor suppressor miR target sequences recognized and/or bound by a miR selected from the group consisting of miR-1-3p, miR-124-3p, miR-143-3p, miR-145-5p, miR-451a, and miR-559 inserted into one or more essential viral genes required for viral replication selected from the group consisting of ICP4 and ICP27; wherein the HSV-1 further comprises one or more modified non-essential viral genes selected from the group consisting of one or more copies of the ICP34.5 gene, the ICP6 gene, and the ICP47 gene.

In a particular embodiment, a pseudotyped oncolytic HSV-1 is provided comprising: a polynucleotide encoding a target antigen selected from the group consisting of CD19 and BCMA; a polynucleotide encoding human MMP-9 inserted into a non-essential viral gene and/or deleted joint region; and one or more tumor suppressor miR target sequences recognized and/or bound by a miR selected from the group consisting of miR-1-3p, miR-124-3p, miR-143-3p, miR-145-5p, miR-451a, and miR-559 inserted into one or more essential viral genes required for viral replication selected from the group consisting of ICP4 and ICP27; wherein the HSV-1 further comprises one or more modified non-essential viral genes selected from the group consisting of one or more copies of the ICP34.5 gene, the ICP6 gene, and the ICP47 gene; and wherein the HSV-1 further comprises a gB:NT mutation, and optionally a gH:KV mutation.

In a particular embodiment, a pseudotyped oncolytic HSV-1 is provided comprising: a polynucleotide encoding a target antigen selected from the group consisting of CD19 and BCMA; a polynucleotide encoding human MMP-9 inserted into a non-essential viral gene and/or deleted joint region; and one or more tumor suppressor miR target sequences recognized and/or bound by a miR selected from the group consisting of miR-124-3p, miR-143-3p, and miR-145-5p inserted into one or more essential viral genes required for viral replication selected from the group consisting of ICP4 and ICP27.

In a particular embodiment, a pseudotyped oncolytic HSV-1 is provided comprising: a polynucleotide encoding a target antigen selected from the group consisting of CD19 and BCMA; a polynucleotide encoding human MMP-9 inserted into a non-essential viral gene and/or deleted joint region; and one or more tumor suppressor miR target sequences recognized and/or bound by a miR selected from the group consisting of miR-124-3p, miR-143-3p, and miR-145-5p inserted into one or more essential viral genes required for viral replication selected from the group consisting of ICP4 and ICP27; wherein the HSV-1 further comprises one or more modified non-essential viral genes selected from the group consisting of one or more copies of the ICP34.5 gene, the ICP6 gene, and the ICP47 gene.

In a particular embodiment, a pseudotyped oncolytic HSV-1 is provided comprising: a polynucleotide encoding a target antigen selected from the group consisting of CD19 and BCMA; a polynucleotide encoding human MMP-9 inserted into a non-essential viral gene and/or deleted joint region; and one or more tumor suppressor miR target sequences recognized and/or bound by a miR selected from the group consisting of miR-124-3p, miR-143-3p, and miR-145-5p inserted into one or more essential viral genes required for viral replication selected from the group consisting of ICP4 and ICP27; wherein the HSV-1 further comprises one or more modified non-essential viral genes selected from the group consisting of one or more copies of the ICP34.5 gene, the ICP6 gene, and the ICP47 gene; and wherein the HSV-1 further comprises a gB:NT mutation, and optionally a gH:KV mutation.

D. Target Antigens

The present disclosure contemplates, in particular embodiments, a recombinant oncolytic virus that encodes one or more target antigens that are not expressed on a target cell or non-target cells, one or more microRNA (miR) target sequences (tumor suppressor miR target sequences), and optionally, one or more therapeutic polypeptides. A "target antigen" or "target antigen of interest" is an antigen that a binding domain contemplated herein, is designed to bind. In particular embodiments, a target antigen is ectopically or exogenously expressed in a target cell, e.g., a cancer cell, that does not normally or endogenously express the target antigen, or that may express insufficient amounts of the target antigen for targeting with an immunotherapy. Without wishing to be bound by any particular theory, it is contemplated that use of validated binding domains, (e.g., the antigen binding domain of an engineered antigen receptor) against target antigens can be used to target or redirect immunotherapies to solid cancers that do not normally or endogenously express the target antigen, but that ectopically or exogenously express sufficient amounts of the target antigen upon infection with oncolytic viruses that encode the one or more target antigens. Stated another way, the present invention contemplates, in part, painting target cells, such as cancer cells, with a target antigen that can be recognized by a validated binding domain for the target antigen, and in this way, existing efficacious immunotherapies expressing one or more engineered antigen receptors can be used to target and/or lyse the painted target cell.

Exemplary target antigens, suitable for use in particular embodiments include, but are not limited to, tumor associated antigens (TAA), tumor specific antigens (TSA), NKG2D ligands, γδ T cell receptor (TCR) ligands, and αβ TCR ligands. In one embodiment, a target antigen is an MHC-peptide complex, such as a class I MHC-peptide complex or a class II MHC-peptide complex.

A "tumor associated antigen" or "TAA" is an antigen that is detectably expressed in or on cancer cells, but is also detectably expressed in some normal cell populations.

A "tumor specific antigen" or "TSA" is an antigen that is only detectably expressed in or on cancer cells.

An "NKG2D ligand" refers to a polypeptide that is recognized and/or bound by an activating receptor, natural-killer group 2, member D (NKG2D). Two families of NKG2D ligands have been identified in humans: MHC class I chain related proteins A (MICA) and B (MICB) and HCMV UL16-binding proteins, ULBP1, ULBP2, ULBP3, ULBP4, ULBP5, and ULBP6. MICA and MICB each have an α1, α2, α3, and transmembrane domain; ULBP1, ULBP2, ULBP3, and ULBP6 each have an α1 and α2 domain and are glycosylphosphatidylinositol (GPI)-linked to the cell membrane; and ULBP4 and ULBP 5 each have an α1 and α2 domain and a transmembrane domain. NKG2D ligands are expressed, in various combinations, on many human cancer cells and immunosuppressive cells (T-regs and myeloid derived suppressor cells (MDSCs) within tumor microenvironments). Cancers expressing one or more NKG2D ligands include, but are not limited to, carcinomas (ovarian, bladder, breast, lung, liver, colon, kidney, prostate, melanoma, Ewing's sarcoma, glioma, and neuroblastoma), leukemias (AML, CML, CLL), lymphomas, and multiple myeloma. NKG2D ligands can also be induced at sites of chronic inflammation, transiently after some infections, following local irradiation, and after treatment with particular drugs, e.g., HDAC inhibitors and bortezomib.

In various embodiments, an oncolytic virus contemplated herein, comprises a polynucleotide encoding a target antigen is selected from the group consisting of: FRα, $α_vβ_6$ integrin, BCMA, CD276, B7-H6, CAIX, CD16, CD19, CD20, CD22, CD30, CD33, CD37, CD38, CD44, CD44v6, CD44v7/8, CD70, CD79a, CD79b, CD123, CD133, CD138, CD171, CEA, CLL-1, CS-1, CSPG4, CTAGE1, EGFR, EGFRvIII, EGP2, EGP40, EPCAM, EPHA2, FAP, FCRL5, AchR, GD2, GD3, GPC3, HER2, IL-11Rα, IL-13Rα2, LAGE-1A, Lambda, LeY, L1-CAM, MAGE-A1, MAGE-A3, MAGE-A4, MAGE-A6, MAGEA10, MelanA or MART1, MSLN, MUC1, MUC16, MICA, MICB, NCAM, NY-ESO-1, PLAC1, PRAME, PSCA, PSMA, ROR1, SSX2, Survivin, TAG72, TEM1/CD248, TEM7R, TPBG, ULBP1, ULBP2, ULBP3, ULBP4, ULBP5, ULBP6, VEGFR2, and WT-1.

In particular embodiments, BCMA is ectopically or exogenously expressed in a target cell, e.g., a cancer cell, that does not normally or endogenously express BCMA, or that may express insufficient amounts of BCMA for targeting with an immunotherapy.

In particular embodiments, CD19 is ectopically or exogenously expressed in a target cell, e.g., a cancer cell, that does not normally or endogenously express CD19, or that may express insufficient amounts of CD19 for targeting with an immunotherapy.

In particular embodiments, CD20 is ectopically or exogenously expressed in a target cell, e.g., a cancer cell, that does not normally or endogenously express CD20, or that may express insufficient amounts of CD20 for targeting with an immunotherapy.

In particular embodiments, CD22 is ectopically or exogenously expressed in a target cell, e.g., a cancer cell, that does not normally or endogenously express CD22, or that may express insufficient amounts of CD22 for targeting with an immunotherapy.

In particular embodiments, CD38 is ectopically or exogenously expressed in a target cell, e.g., a cancer cell, that does not normally or endogenously express CD38, or that may express insufficient amounts of CD38 for targeting with an immunotherapy.

In particular embodiments, one or more of NKG2D ligands ULBP1, ULBP2, ULBP3, ULBP4, ULBP5, ULBP6, MICA and MICB, is ectopically or exogenously expressed in a target cell, e.g., a cancer cell, that does not normally or endogenously express the NKG2D ligand(s), or that may express insufficient amounts of NKG2D ligand(s) for targeting with an immunotherapy.

E. Tumor Suppressor MiRNAs (MIR) and Target Sequences

"MiRNA(s)" or "microRNA(s)" or "miR(s)" refer to small non-coding RNAs of 20-22 nucleotides that regulate gene expression by translational repression, mRNA cleavage, and mRNA decay initiated by miRNA-guided rapid deadenylation. miRNAs are transcribed by the RNA polymerase II enzyme to produce a primary-miRNA (primiRNA) of several hundred to a thousand nucleotides; pri-miRNA is usually capped at the 5' end and poly-adenylated at the 3' end, similar to protein-coding mRNAs (Cai et al., 2004). pri-miRNAs form specific hairpin-shaped stem-loop secondary structures and are processed by Drosha and DGCR8/Pasha into 60- to 70-nt pre-miRNA with a 5' phosphate and a 3' 2 nt overhang. The pre-miRNAs are then transported to the cytoplasm by Exportin-5 (Exp5) and further processed to a short double strand miRNA:miRNA* duplex by Dicer. The miRNA:miRNA* duplex is unwound into a mature miRNA (guide strand) and miRNA* (passenger strand) by a helicase and is asymmetrically incorporated into the RNA-induced silencing complex (RISC) where they regulate gene expression by mRNA degradation or translational repression while the miRNA* is quickly degraded. miRNA naming conventions, miR sequences, and miR target sequences are disclosed in the miRbase Release 22 database.

The present disclosure contemplates, in particular embodiments, a recombinant oncolytic virus that encodes one or more target antigens, one or more tumor suppressor microRNA (miR) target sequences inserted into one or more essential viral genes, and optionally, one or more therapeutic polypeptides. In particular embodiments, a "tumor suppressor microRNA" or "tumor suppressor miR" refers to a microRNA that is preferentially expressed in a non-target cell, and whose expression is substantially decreased or absent in a target cell. In particular embodiments, a "tumor suppressor microRNA" or "tumor suppressor miR" refers to a microRNA that is expressed in a non-target cell and not expressed in a target cell. In particular embodiments, a "tumor suppressor microRNA" or "tumor suppressor miR" refers to a microRNA that is detectably expressed, or that is expressed in sufficient amounts to target a tumor suppressor miR target sequence, in a normal non-cancerous cell and not detectably expressed, or that is expressed at insufficient amounts to target a tumor suppressor miR target sequence, in a cancer cell. In particular embodiments, a "tumor suppressor microRNA" or "tumor suppressor miR" refers to a microRNA that is detectably expressed, or that is expressed in sufficient amounts to target a tumor suppressor miR target sequence, in one or more cells and/or tissues near or adjacent to one or more cancer cells that do not detectably express, or that express insufficient amounts to target a tumor suppressor miR target sequence, the microRNA. The term "specifically expressed" means that a molecule is exclusively expressed in a target cell or a non-target cell. In particular embodiments, a miR is specifically expressed in a non-target cell.

The term "selectively expressed" means that a molecule is preferentially expressed in a target cell, but may also be expressed in one or more populations of non-target cells.

A "tumor suppressor microRNA target site" or "tumor suppressor miRNA target site" or "tumor suppressor miR target site" or "tumor suppressor microRNA target sequence" or "tumor suppressor miRNA target sequence" or "tumor suppressor miR target sequence" refers to a polynucleotide sequence complementary to the miRNA or the guide strand.

In particular embodiments, an oncolytic virus contemplated herein encodes at least one target antigen and comprises one or more tumor suppressor miR target sequences in one or more viral genes essential for viral replication. Without wishing to be bound by any particular theory, it is contemplated that viral mRNAs encoding viral proteins essential for viral replication and that comprise one or more tumor suppressor miR target sequences are targeted for degradation and/or translation repression by tumor suppressor miRs expressed in non-target or normal cells, thereby decreasing, reducing, attenuating, or suppressing or preventing viral replication in the non-target or normal cell. In contrast, viral mRNAs encoding viral proteins essential for viral replication and that comprise one or more tumor suppressor miR target sequences would not be targeted for degradation and/or translation repression in target cells, e.g., cancer cells, that do not express or that express insufficient amounts of the cognate tumor suppressor miRs.

"Decreased viral replication" or "reduced viral replication" or "attenuated viral replication" or "suppressed viral replication" refers to a level of viral replication that is absent or lower in one or more non-target or normal cells or cell populations thereof compared to the level of viral replication in one or more target or cancer cells or cell populations thereof. In particular embodiments, the level of viral replication in one or more non-target or normal cells or cell populations thereof is reduced or decreased at least 100%, at least 95%, at least 90%, at least 85%, at least 80%, at least 75%, at least 70% or more compared to the level of viral replication in one or more target or cancer cells or cell populations thereof.

Oncolytic viruses contemplated in particular embodiments, comprise one or more tumor suppressor miR target sequences inserted into one or more essential viral genes required for viral replication. In one embodiment, the one or more tumor suppressor miR target sequences are not recognized and/or not bound by a miR(s) endogenously or natively expressed in a target cell or cancer cell. In one embodiment, the one or more tumor suppressor miR target sequences are recognized and/or bound by one or more miRs expressed in a non-target cell or normal cell. In one embodiment, one or more tumor suppressor miR target sequences inserted into one or more essential viral genes required for viral replication reduces, decreases, or attenuates viral replication in a non-target cell or normal cell compared to viral replication in a target cell or cancer cell. In one embodiment, one or more tumor suppressor miR target sequences inserted into one or more essential viral genes required for viral replication increases viral replication in a target cell or cancer cell compared to viral replication in a non-target cell or normal cell.

In particular embodiments, one or more tumor suppressor miR target sequences is inserted into a 5' UTR, intron, and/or 3' UTR of an essential viral gene.

In particular embodiments, one or more tumor suppressor miR target sequences is inserted into a 5' UTR, intron, and/or 3' UTR of an essential HSV-1 gene including, but not limited to: UL1, UL5, UL6, UL7, UL8, UL9, UL12, UL14, UL15, UL17, UL18, UL19, UL22, UL23, UL24, UL25, UL2, UL27, UL28, UL29, UL30, UL31, UL32, UL33, UL35, UL36, UL37, UL38, UL42, UL48, UL49, UL52, UL53, UL54 (ICP27), one or both copies of ICP4, and US6.

In particular embodiments, an oncolytic HSV-1 comprises one or more tumor suppressor miR target sequences inserted into a 5' UTR, intron, and/or 3' UTR of an essential viral gene selected from the group consisting of: UL19, UL30, UL54 (ICP27), and one or both copies of ICP4.

In some embodiments, an oncolytic HSV-1 comprises one or more tumor suppressor miR target sequences inserted into a 5' UTR, intron, and/or 3' UTR of an essential viral gene selected from the group consisting of: UL54 (ICP27) and one or both copies of ICP4.

In certain embodiments, an oncolytic HSV-1 comprises one or more tumor suppressor miR target sequences inserted into a 5' UTR, intron, and/or 3' UTR of UL54 (ICP27) and one copy of ICP4.

In particular embodiments, an oncolytic HSV-1 comprises one or more tumor suppressor miR target sequences inserted into a 5' UTR, intron, and/or 3' UTR of UL54 (ICP27) and both copies of ICP4.

In preferred embodiments the target cell is a cancer cell. Non-target cells include but are not limited to non-cancer cells in a tissue near the cancer cell and non-cancer cells in a tissue adjacent to the cancer cell.

In a particular preferred embodiment, the target cell is a solid cancer cell.

Illustrative examples of solid cancers that are suitable for targeting with the compositions and methods contemplated in particular embodiments include, but are not limited to adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain/CNS cancer, breast cancer, bronchial tumors, cardiac tumors, cervical cancer, cholangiocarcinoma, chondrosarcoma, chordoma, colon cancer, colorectal cancer, craniopharyngioma, ductal carcinoma in situ (DCIS) endometrial cancer, ependymoma, esophageal cancer, esthesioneuroblastoma, Ewing's sarcoma, extracranial germ cell tumor, extragonadal germ cell tumor, eye cancer, fallopian tube cancer, fibrous histiosarcoma, fibrosarcoma, gallbladder cancer, gastric cancer, gastrointestinal carcinoid tumors, gastrointestinal stromal tumor (GIST), germ cell tumors, glioma, glioblastoma, head and neck cancer, hemangioblastoma, hepatocellular cancer, hypopharyngeal cancer, intraocular melanoma, kaposi sarcoma, kidney cancer, laryngeal cancer, leiomyosarcoma, lip cancer, liposarcoma, liver cancer, lung cancer, non-small cell lung cancer, lung carcinoid tumor, malignant mesothelioma, medullary carcinoma, medulloblastoma, menangioma, melanoma, Merkel cell carcinoma, midline tract carcinoma, mouth cancer, myxosarcoma, myelodysplastic syndrome, myeloproliferative neoplasms, nasal cavity and paranasal sinus cancer, nasopharyngeal cancer, neuroblastoma, oligodendroglioma, oral cancer, oral cavity cancer, oropharyngeal cancer, osteosarcoma, ovarian cancer, pancreatic cancer, pancreatic islet cell tumors, papillary carcinoma, paraganglioma, parathyroid cancer, penile cancer, pharyngeal cancer, pheochromocytoma, pinealoma, pituitary tumor, pleuropulmonary blastoma, primary peritoneal cancer, prostate cancer, rectal cancer, retinoblastoma, renal cell carcinoma, renal pelvis and ureter cancer, rhabdomyosarcoma, salivary gland cancer, sebaceous gland carcinoma, skin cancer, soft tissue sarcoma, squamous cell carcinoma, small cell lung cancer, small intestine cancer, stomach cancer, sweat gland carcinoma, synovioma, testicular cancer, throat cancer, thymus cancer, thyroid cancer, urethral cancer, uterine cancer, uterine sarcoma, vaginal cancer, vascular cancer, vulvar cancer, and Wilms Tumor.

In particular embodiments, the solid cancer is selected from the group consisting of: liver cancer, pancreatic cancer, lung cancer, breast cancer, bladder cancer, brain cancer, bone cancer, thyroid cancer, kidney cancer, and skin cancer.

In particular embodiments, the solid cancer is a bladder cancer, breast cancer, colon cancer, glioblastoma, head and neck cancer, lung cancer, pancreatic cell, or a schwannoma.

In one embodiment, the cancer is a liquid cancer including but not limited to leukemias, lymphomas, and myelomas.

In particular embodiments, a recombinant oncolytic virus for treating bladder cancer encodes a target antigen and comprises one or more copies of one or more tumor suppressive miR target sequences for hsa-miR-136-3p, hsa-miR-432, hsa-miR-1-3p, hsa-miR-127-3p, hsa-miR-379-5p, hsa-miR-493-5p, hsa-miR-223-5p, hsa-miR-223-5p, hsa-miR-136-5p, hsa-miR-451 a, hsa-miR-487b-3p, hsa-miR-370-3p, hsa-miR-410-3p, hsa-miR-431-3p, hsa-miR-4485-3p, hsa-miR-4485-5p, hsa-miR-127-5p, hsa-miR-409-3p, hsa-miR-338-3p, hsa-miR-559, hsa-miR-411-5p, hsa-miR-133a-5p, hsa-miR-143-3p, hsa-miR-376b-3p, hsa-miR-758-3p, hsa-miR-1-3p, hsa-miR-101, hsa-miR-1180, hsa-miR-1236, hsa-miR-124-3p, hsa-miR-125b, hsa-miR-126, hsa-miR-1280, hsa-miR-133a, hsa-miR-133b, hsa-miR-141, hsa-miR-143-3p, hsa-miR-144, hsa-miR-145-5p, hsa-miR-155, hsa-miR-16, hsa-miR-192, hsa-miR-195, hsa-miR-200a, hsa-miR-200b, hsa-miR-200c, hsa-miR-203, hsa-miR-205, hsa-miR-214, hsa-miR-218, hsa-miR-23b, hsa-miR-26a, hsa-miR-29c, hsa-miR-320c, hsa-miR-34a, hsa-miR-370, hsa-miR-409-3p, hsa-miR-429, hsa-miR-451, hsa-miR-490-5p, hsa-miR-493, hsa-miR-576-3p, and/or hsa-miR-99a inserted into the 5' UTR, intron and/or 3' UTR of one or more viral genes essential for viral replication.

In particular embodiments, a recombinant oncolytic virus for treating brain cancers, including, but not limited to astrocytoma, glioblastoma, or glioma, encodes a target antigen and comprises one or more copies of one or more tumor suppressive miR target sequences for hsa-miR-1251-5p, hsa-miR-219a-5p, hsa-miR-219a-2-3p, hsa-miR-124-3p, hsa-miR-448, hsa-miR-138-2-3p, hsa-miR-490-5p, hsa-miR-129-1-3p, hsa-miR-1264, hsa-miR-3943, hsa-miR-490-3p, hsa-miR-383-5p, hsa-miR-133b, hsa-miR-129-2-3p, hsa-miR-128-2-5p, hsa-miR-133a-3p, hsa-miR-129-5p, hsa-miR-1-3p, hsa-miR-885-3p, hsa-miR-124-3p, hsa-miR-759, hsa-miR-7158-3p, hsa-miR-770-5p, hsa-miR-135a-5p, hsa-miR-885-5p, let-7g-5p, hsa-miR-100, hsa-miR-101, hsa-miR-106a, hsa-miR-124a, hsa-miR-125a, hsa-miR-125a-5p, hsa-miR-125b, hsa-miR-127-3p, hsa-miR-128, hsa-miR-129, hsa-miR-136, hsa-miR-137, hsa-miR-139-5p, hsa-miR-142-3p, hsa-miR-143-3p, hsa-miR-145-5p, hsa-miR-146b-5p, hsa-miR-149, hsa-miR-152, hsa-miR-153, hsa-miR-195, hsa-miR-21, hsa-miR-212-3p, hsa-miR-219-5p, hsa-miR-222, hsa-miR-29b, hsa-miR-31, hsa-miR-3189-3p, hsa-miR-320, hsa-miR-320a, hsa-miR-326, hsa-miR-330, hsa-miR-331-3p, hsa-miR-340, hsa-miR-342, hsa-miR-34a, hsa-miR-376a, hsa-miR-449a, hsa-miR-483-5p, hsa-miR-503, hsa-miR-577, hsa-miR-663, hsa-miR-7, hsa-miR-7-5p, hsa-miR-873, let-7a, let-7f, hsa-miR-107, hsa-miR-122, hsa-miR-139, hsa-miR-146a, hsa-miR-146b, hsa-miR-15b, hsa-miR-16, hsa-miR-181a, hsa-miR-181a-1, hsa-miR-181a-2, hsa-miR-181b, hsa-miR-181b-1, hsa-miR-181b-2, hsa-miR-181c, hsa-miR-184, hsa-miR-185, hsa-miR-9a-3p, hsa-miR-200a, hsa-miR-200b, hsa-miR-203, hsa-miR-204, hsa-miR-205, hsa-miR-218, hsa-miR-23b, hsa-miR-26b, hsa-miR-27a, hsa-miR-29c, hsa-miR-328, hsa-miR-34c-3p, hsa-miR-34c-5p, hsa-miR-375, hsa-miR-383, hsa-miR-451, hsa-miR-452, hsa-miR-495, hsa-miR-584, hsa-miR-622, hsa-miR-656, hsa-miR-98, hsa-miR-181b-5p, hsa-miR-200b, and/or hsa-miR-3189-3p inserted into the 5' UTR, intron and/or 3' UTR of one or more viral genes essential for viral replication.

In particular embodiments, a recombinant oncolytic virus for treating breast cancer encodes a target antigen and comprises one or more copies of one or more tumor suppressive miR target sequences for hsa-miR-10b-5p, hsa-miR-126-3p, hsa-miR-145-5p, hsa-miR-451a, hsa-miR-199b-5p, hsa-miR-5683, hsa-miR-3195, hsa-miR-3182, hsa-miR-1271-5p, hsa-miR-204-5p, hsa-miR-409-5p, hsa-miR-136-5p, hsa-miR-514a-5p, hsa-miR-559, hsa-miR-483-3p, hsa-miR-1-3p, hsa-miR-6080, hsa-miR-144-3p, hsa-miR-10b-3p, hsa-miR-6130, hsa-miR-6089, hsa-miR-203b-5p, hsa-miR-4266, hsa-miR-4327, hsa-miR-5694, hsa-miR-193b, let-7a, let-7a-1, let-7a-2, let-7a-3, let-7b, let-7c, let-7d, let-7e, let-7f-1, let-7f-2, let-7g, let-7i, hsa-miR-100, hsa-miR-07, hsa-miR-10a, hsa-miR-10b, hsa-miR-122, hsa-miR-124-3p, hsa-miR-1258, miR-125a-5p, hsa-miR-125b, hsa-miR-126, hsa-miR-127, hsa-miR-129, hsa-miR-130a, hsa-miR-132, hsa-miR-133a, hsa-miR-143-3p, hsa-miR-145-5p, hsa-miR-146a, hsa-miR-146b, hsa-miR-147, hsa-miR-148a, hsa-miR-49, hsa-miR-152, hsa-miR-153, hsa-miR-15a, hsa-miR-16, hsa-miR-17-5p, hsa-miR-181a, hsa-miR-1826, hsa-miR-183, hsa-miR-85, hsa-miR-191, hsa-miR-193a-3p, hsa-miR-195, hsa-miR-199b-5p, hsa-miR-19a-3p, hsa-miR-200a, hsa-miR-200b, hsa-miR-200c, hsa-miR-205, hsa-miR-206, hsa-miR-21, hsa-miR-216b, hsa-miR-218, hsa-miR-22, hsa-miR-26a, hsa-miR-26b, hsa-miR-300, hsa-miR-30a, hsa-miR-31, hsa-miR-335, hsa-miR-339-5p, hsa-miR-33b, hsa-miR-34a, hsa-miR-34b, hsa-miR-34c, hsa-miR-374a, hsa-miR-379, hsa-miR-381, hsa-miR-383, hsa-miR-425, hsa-miR-429, hsa-miR-450b-3p, hsa-miR-494, hsa-miR-495, hsa-miR-497, hsa-miR-502-5p, hsa-miR-517a, hsa-miR-574-3p, hsa-miR-638, hsa-miR-7, hsa-miR-720, hsa-miR-873, hsa-miR-874, hsa-miR-92a, hsa-miR-98, hsa-miR-99a, hsa-miR-290-3p, and/or hsa-miR-290-5p inserted into the 5' UTR, intron and/or 3' UTR of one or more viral genes essential for viral replication.

In particular embodiments, a recombinant oncolytic virus for treating cervical cancer encodes a target antigen and comprises one or more copies of one or more tumor suppressive miR target sequences for hsa-miR-143-3p, hsa-miR-145-5p, hsa-miR-17-5p, hsa-miR-203, hsa-miR-214, hsa-miR-218, hsa-miR-335, hsa-miR-342-3p, hsa-miR-372, hsa-miR-424, hsa-miR-491-5p, hsa-miR-497, hsa-miR-7, hsa-miR-99a, hsa-miR-99b, hsa-miR-100, hsa-miR-101, hsa-miR-15a, hsa-miR-16, hsa-miR-34a, hsa-miR-886-5p, hsa-miR-106a, hsa-miR-124-3p, hsa-miR-148a, hsa-miR-29a, and/or hsa-miR-375 inserted into the 5' UTR, intron and/or 3' UTR of one or more viral genes essential for viral replication.

In particular embodiments, a recombinant oncolytic virus for treating colon or colorectal cancer encodes a target antigen and comprises one or more copies of one or more tumor suppressive miR target sequences for hsa-miR-133a-5p, hsa-miR-490-5p, hsa-miR-124-3p, hsa-miR-137, hsa-miR-655-3p, hsa-miR-376c-3p, hsa-miR-369-5p, hsa-miR-490-3p, hsa-miR-432-5p, hsa-miR-487b-3p, hsa-miR-342-3p, hsa-miR-223-3p, hsa-miR-136-3p, hsa-miR-136-3p, hsa-miR-143-3p, hsa-miR-1-3p, hsa-miR-214-3p, hsa-miR-199a-3p, hsa-miR-199b-3p, hsa-miR-451a, hsa-miR-127-3p, hsa-miR-133a-3p, hsa-miR-145-5p, hsa-miR-199a-5p, let-7a-1, let-7a-2, let-7a-3, let-7b, let-c, let-7d, let-7e, let-7f-1, let-7f-2, let-7g, let-7i, hsa-miR-100, hsa-miR-101, hsa-miR-126, hsa-miR-142-3p, hsa-miR-192, hsa-miR-200c, hsa-miR-21, hsa-miR-214, hsa-miR-215, hsa-miR-22, hsa-miR-25, hsa-miR-302a, hsa-miR-320, hsa-miR-320a, hsa-miR-34a, hsa-miR-34c, hsa-miR-365, hsa-miR-373, hsa-miR-424, hsa-miR-429, hsa-miR-455, hsa-miR-484, hsa-miR-502, hsa-miR-503, hsa-miR-93, hsa-miR-98, hsa-miR-186, hsa-miR-30a-5p, hsa-miR-627, let-7a, hsa-miR-1-3p, hsa-miR-125a, hsa-miR-29, hsa-miR-1295b-3p, hsa-miR-1307, hsa-miR-130b, hsa-miR-132, hsa-miR-133a, hsa-miR-133b, hsa-miR-137, hsa-miR-138, hsa-miR-139, hsa-miR-139-5p, hsa-miR-140-5p, hsa-miR-8a, hsa-miR-148b, hsa-miR-149, hsa-miR-150-5p, hsa-miR-154, hsa-miR-15a, hsa-miR-15b, hsa-miR-18a, hsa-miR-191, hsa-miR-193a-5p, hsa-miR-194, hsa-miR-195, hsa-miR-196a, hsa-miR-198, hsa-miR-199a-5p, hsa-miR-203, hsa-miR-204-5p, hsa-miR-206, hsa-miR-212, hsa-miR-218, hsa-miR-224, hsa-miR-24-3p, hsa-miR-26b, hsa-miR-27a, hsa-miR-28-3p, hsa-miR-28-5p, hsa-miR-29b, hsa-miR-30a-3p, hsa-miR-30b, hsa-miR-328, hsa-miR-338-3p, hsa-miR-342, hsa-miR-34a-5p, hsa-miR-361-5p, hsa-miR-375, hsa-miR-378, hsa-miR-378a-3p, hsa-miR-378a-5p, hsa-miR-409-3p, hsa-miR-422a, hsa-miR-4487, hsa-miR-483, hsa-miR-497, hsa-miR-498, hsa-miR-518a, hsa-miR-551a, hsa-miR-574-5p, hsa-miR-625, hsa-miR-638, hsa-miR-7, hsa-miR-96-5p, hsa-miR-202-3p, hsa-miR-30a, and/or hsa-miR-451 inserted into the 5' UTR, intron and/or 3' UTR of one or more viral genes essential required for viral replication.

In particular embodiments, a recombinant oncolytic virus for treating endometrial cancer encodes a target antigen and comprises one or more copies of one or more tumor suppressive miR target sequences for hsa-miR-101, hsa-miR-130a, hsa-miR-130b, hsa-miR-134, hsa-miR-143-3p, hsa-miR-145-5p, hsa-miR-152, hsa-miR-205, hsa-miR-223, hsa-miR-301a, hsa-miR-301b, hsa-miR-30c, hsa-miR-34a, hsa-miR-34c, hsa-miR-424, hsa-miR-449a, hsa-miR-543, and/or hsa-miR-34b inserted into the 5' UTR, intron and/or 3' UTR of one or more viral genes essential for viral replication.

In particular embodiments, a recombinant oncolytic virus for treating hematologic cancer including, but not limited to leukemia, lymphoma, and myeloma, encodes a target antigen and comprises one or more copies of one or more tumor suppressive miR target sequences for hsa-miR-125b, hsa-miR-38, hsa-miR-15a, hsa-miR-15b, hsa-miR-16, hsa-miR-16-1-3p, hsa-miR-16-2, hsa-miR-181a, hsa-miR-181b, hsa-miR-195, hsa-miR-223, hsa-miR-29b, hsa-miR-34b, hsa-miR-424, hsa-miR-10a, hsa-miR-146a, hsa-miR-150, hsa-miR-151, hsa-miR-155, hsa-miR-2278, hsa-miR-30e, hsa-miR-31, hsa-miR-326, hsa-miR-564, hsa-miR-27a, let-7b, hsa-miR-24a, hsa-miR-142-3p, let-7c, hsa-miR-17, hsa-miR-20a, hsa-miR-29a, hsa-miR-30c, hsa-miR-720, hsa-miR-107, hsa-miR-342, hsa-miR-34a, hsa-miR-202, hsa-miR-142-5p, hsa-miR-29c, hsa-miR-145-5p, hsa-miR-93b. hsa-miR-199a, hsa-miR-214, hsa-miR-22, hsa-miR-137, and/or hsa-miR-197 inserted into the 5' UTR, intron and/or 3' UTR of one or more viral genes essential for viral replication.

In particular embodiments, a recombinant oncolytic virus for treating kidney cancer encodes a target antigen and comprises one or more copies of one or more tumor suppressive miR target sequences for hsa-miR-145-5p, hsa-miR-1826, hsa-miR-199a, hsa-miR-199a-3p, hsa-miR-203, hsa-miR-205, hsa-miR-497, hsa-miR-508-3p, hsa-miR-509-3p, let-7a, let-7d, hsa-miR-106a*, hsa-miR-26. hsa-miR-1285, hsa-miR-129-3p, hsa-miR-1291, hsa-miR-133a, hsa-miR-135a, hsa-miR-138, hsa-miR-141, hsa-miR-143-3p, hsa-miR-182-5p, hsa-miR-200a, hsa-miR-218, hsa-miR-28-5p, hsa-miR-30a, hsa-miR-30c, hsa-miR-30d, hsa-miR-34a, hsa-miR-429, hsa-miR-509-5p, hsa-miR-646, hsa-miR-133b, let-7b, let-7c, hsa-miR-200c, hsa-miR-204, hsa-miR-335, hsa-miR-377, and/or hsa-miR-506 inserted into the 5' UTR, intron and/or 3' UTR of one or more viral genes essential for viral replication.

In particular embodiments, a recombinant oncolytic virus for treating liver cancer including but not limited to hepatocellular carcinoma, encodes a target antigen and comprises one or more copies of one or more tumor suppressive miR target sequences for let-7a-1, let-7a-2, let-7a-3, let-7b, let-7c, let-7d, let-7e, let-7f, let-7f-1, let-7f-2, let-7g, let-7i, hsa-miR-1-3p, hsa-miR-100, hsa-miR-101, hsa-miR-105, hsa-miR-122, hsa-miR-122a, hsa-miR-1236, hsa-miR-124-3p, hsa-miR-125b, hsa-miR-126, hsa-miR-127, hsa-miR-1271, hsa-miR-128-3p, hsa-miR-129-5p, hsa-miR-1 30a, hsa-miR-130b, hsa-miR-133a, hsa-miR-134, hsa-miR-137, hsa-miR-138, hsa-miR-139, hsa-miR-139-5p, miR-140-5p, hsa-miR-141, hsa-miR-142-3p, hsa-miR-143-3p, hsa-miR-144, hsa-miR-145-5p, hsa-miR-146a, hsa-miR-148a, hsa-miR-148b, hsa-miR-150-5p, hsa-miR-15b, hsa-miR-16, hsa-miR-181a-5p, hsa-miR-185, hsa-miR-188-5p, hsa-miR-193b, hsa-miR-195, hsa-miR-195-5p, hsa-miR-197, hsa-miR-198, hsa-miR-199a, hsa-miR-199a-5p, hsa-miR-199b, hsa-miR-199b-5p, hsa-miR-200a, hsa-miR-200b, hsa-miR-200c, hsa-miR-202, hsa-miR-203, hsa-miR-204-3p, hsa-miR-205, hsa-miR-206, hsa-miR-20a, hsa-miR-21, hsa-miR-21-3p, hsa-miR-212, hsa-miR-214, hsa-miR-217, hsa-miR-218, hsa-miR-219-5p, hsa-miR-22, hsa-miR-223, hsa-miR-26a, hsa-miR-26b, hsa-miR-29a, hsa-miR-29b-1, hsa-miR-29b-2, hsa-miR-29c, hsa-miR-302b, hsa-miR-302c, hsa-miR-30a, hsa-miR-30a-3p, hsa-miR-335, hsa-miR-338-3p, hsa-miR-33a, hsa-miR-34a, hsa-miR-34b, hsa-miR-365, hsa-miR-370, hsa-miR-372, hsa-miR-375, hsa-miR-376a, hsa-miR-377, hsa-miR-422a, hsa-miR-424, hsa-miR-424-5p, hsa-miR-433, hsa-miR-4458, hsa-miR-448, hsa-miR-450a, hsa-miR-451, hsa-miR-485-5p, hsa-miR-486-5p, hsa-miR-497, hsa-miR-497, hsa-miR-503, hsa-miR-506, hsa-miR-519D, hsa-miR-520a, hsa-miR-520b, hsa-miR-520c-3p, hsa-miR-582-5p, hsa-miR-590-5p, hsa-miR-610, hsa-miR-612, hsa-miR-625, hsa-miR-637, hsa-miR-675, hsa-miR-7, hsa-miR-877, hsa-miR-940, hsa-miR-941, hsa-miR-98, hsa-miR-99a, hsa-miR-132, and/or hsa-miR-31 inserted into the 5' UTR, intron and/or 3' UTR of one or more viral genes essential for viral replication.

In particular embodiments, a recombinant oncolytic virus for treating lung cancer encodes a target antigen and comprises one or more copies of one or more tumor suppressive miR target sequences for hsa-miR-143-3p, hsa-miR-126-3p, hsa-miR-126-5p, hsa-miR-1266-3p, hsa-miR-6130, hsa-miR-6080, hsa-miR-511-5p, hsa-miR-223-5p, hsa-miR-199b-5p, hsa-miR-199a-3p, hsa-miR-199b-3p, hsa-miR-451a, hsa-miR-142-5p, hsa-miR-144, hsa-miR-150-5p, hsa-miR-142-3p, hsa-miR-214-3p, hsa-miR-214-5p, hsa-miR-199a-5p, hsa-miR-145-3p, hsa-miR-145-5p, hsa-miR-1297, hsa-miR-141, hsa-miR-16, hsa-miR-200a, hsa-miR-200b, hsa-miR-200c, hsa-miR-29b, hsa-miR-381, hsa-miR-409-3p, hsa-miR-429, hsa-miR-451, hsa-miR-99a, let-7a-1, let-7a-2, let-7a-3, let-7b, let-7c, let-7d, let-7e, let-7f, let-7f-2, let-7g, let-7i, hsa-miR-1-3p, hsa-miR-101, hsa-miR-33b. hsa-miR-138, hsa-miR-142-5p, hsa-miR-144, hsa-miR-1469, hsa-miR-146a, hsa-miR-153, hsa-miR-15a, hsa-miR-15b, hsa-miR-16-1, hsa-miR-16-2, hsa-miR-182, hsa-miR-192, hsa-miR-193a-3p, hsa-miR-194, hsa-miR-195, hsa-miR-198, hsa-miR-203, hsa-miR-217, hsa-miR-218, hsa-miR-22, hsa-miR-223, hsa-miR-26a, hsa-miR-26b, hsa-miR-29c, hsa-miR-33a, hsa-miR-34a, hsa-miR-34b, hsa-miR-34c, hsa-miR-365, hsa-miR-449a, hsa-miR-449b, hsa-miR-486-5p, hsa-miR-545, hsa-miR-610, hsa-miR-614, hsa-miR-630, hsa-miR-660, hsa-miR-7515, hsa-miR-9500, hsa-miR-98, hsa-miR-99b, hsa-miR-133a, let-7a, hsa-miR-100, hsa-miR-106a, hsa-miR-107, hsa-miR-124-3p, hsa-miR-125a-3p, hsa-miR-125a-5p, hsa-miR-126, hsa-miR-129, hsa-miR-137, hsa-miR-140, hsa-miR-143, hsa-miR-146b, hsa-miR-148a, hsa-miR-148b, hsa-miR-149, hsa-miR-152, hsa-miR-154, hsa-miR-155, hsa-miR-17-5p, hsa-miR-181a-2, hsa-miR-181b, hsa-miR-181b-1, hsa-miR-181b-2, hsa-miR-181c, hsa-miR-181d, hsa-miR-184, hsa-miR-186, hsa-miR-193b, hsa-miR-199a, hsa-miR-204, hsa-miR-212, hsa-miR-221, hsa-miR-224, hsa-miR-27a, hsa-miR-27b, hsa-miR-29a, hsa-miR-30a, hsa-miR-30b, hsamiR-30c, hsa-miR-30d, hsa-miR-30d-5p, hsa-miR-30e-5p, hsa-miR-32, hsa-miR-335, hsa-miR-338-3p, hsa-miR-340, hsa-miR-342-3p, hsa-miR-361-3p, hsa-miR-373, hsa-miR-375, hsa-miR-4500, hsa-miR-4782-3p, hsa-miR-497, hsa-miR-503, hsa-miR-512-3p, hsa-miR-520a-3p, hsa-miR-526b, and/or hsa-miR-96 inserted into the 5' UTR, intron and or 3' UTR of one or more viral genes essential for viral replication.

In particular embodiments, a recombinant oncolytic virus for treating melanoma encodes a target antigen and comprises one or more copies of one or more tumor suppressive miR target sequences for let-7b, hsa-miR-101, hsa-miR-125b, hsa-miR-1280, hsa-miR-143, hsa-miR-146a, hsa-miR-146b, hsa-miR-155, hsa-miR-184, hsa-miR-185, hsa-miR-18b, hsa-miR-193b, hsa-miR-200c, hsa-miR-203, hsa-miR-204, hsa-miR-205, hsa-miR-206, hsa-miR-20a, hsa-miR-21, hsa-miR-218, hsa-miR-26a, hsa-miR-31, hsa-miR-33a, hsa-miR-34a, hsa-miR-34c, hsa-miR-376a, hsa-miR-376c, hsa-miR-573, hsa-miR-7-5p, hsa-miR-9, and/or hsa-miR-98 inserted into the 5' UTR, intron and/or 3' UTR of one or more viral genes essential for viral replication.

In particular embodiments, a recombinant oncolytic virus for treating oral cancer encodes a target antigen and comprises one or more copies of one or more tumor suppressive miR target sequences for let-7d, hsa-miR-218, hsa-miR-34a, hsa-miR-375, hsa-miR-494, hsa-miR-100, hsa-miR-124-3p, hsa-miR-1250, hsa-miR-125b, hsa-miR-126, hsa-miR-1271, hsa-miR-136, hsa-miR-138, hsa-miR-145-5p, hsa-miR-147, hsa-miR-148a, hsa-miR-181a, hsa-miR-206, hsa-miR-220a, hsa-miR-26b, hsa-miR-29a, hsa-miR-32, hsa-miR-323-5p, hsa-miR-329, hsa-miR-338, hsa-miR-370, hsa-miR-410, hsa-miR-429, hsa-miR-433, hsa-miR-499a-5p, hsa-miR-503, hsa-miR-506, hsa-miR-632, hsa-miR-646, hsa-miR-668, hsa-miR-877, and/or hsa-miR-9 inserted into the 5' UTR, intron and/or 3' UTR of one or more viral genes essential for viral replication.

In particular embodiments, a recombinant oncolytic virus for treating ovarian cancer encodes a target antigen and comprises one or more copies of one or more tumor suppressive miR target sequences for let-7i, hsa-miR-100, hsa-miR-124-3p, hsa-miR-I25b, hsa-miR-129-5p, hsa-miR-130b, hsa-miR-133a, hsa-miR-137, hsa-miR-138, hsa-miR-141, hsa-miR-145-5p, hsa-miR-148a, hsa-miR-152, hsa-miR-153, hsa-miR-155, hsa-miR-199a, hsa-miR-200a, hsa-miR-200b, hsa-miR-200c, hsa-miR-212, hsa-miR-335, hsa-miR-34a, hsa-miR-34b, hsa-miR-34c, hsa-miR-409-3p, hsa-miR-41 1, hsa-miR-429, hsa-miR-432, hsa-miR-449a, hsa-miR-494, hsa-miR-497, hsa-miR-498, miR-519d, hsa-miR-655, hsa-miR-9, hsa-miR-98, hsa-miR-101, hsa-miR-532-5p, hsa-miR-124a, hsa-miR-92, hsa-miR-193a, and/or hsa-miR-7 inserted into the 5' UTR, intron and/or 3' UTR of one or more viral genes essential for viral replication.

In particular embodiments, a recombinant oncolytic virus for treating pancreatic cancer encodes a target antigen and comprises one or more copies of one or more tumor suppressive miR target sequences for hsa-miR-216a-5p, hsa-miR-802, hsa-miR-217, hsa-miR-145-5p, hsa-miR-143-3p, hsa-miR-451a, hsa-miR-375, hsa-miR-214-3p, hsa-miR-216b-3p, hsa-miR-432-5p, hsa-miR-216a-3p, hsa-miR-199b-5p, hsa-miR-199a-5p, hsa-miR-136-3p, hsa-miR-216b-5p, hsa-miR-136-5p, hsa-miR-127-3p, hsa-miR-199a-3p, hsa-miR-199b-3p, hsa-miR-559, hsa-miR-129-2-3p, hsa-miR-4507, hsa-miR-148a-3p, hsa-miR-101, hsa-miR-124-3p, hsa-miR-1247, hsa-miR-133a, hsa-miR-141, hsa-miR-146a, hsa-miR-148a, hsa-miR-148b, hsa-miR-150-5p, hsa-miR-152, hsa-miR-15a, hsa-miR-198, hsa-miR-203, hsa-miR-214, hsa-miR-216a, hsa-miR-29c, hsa-miR-335, hsa-miR-34a, hsa-miR-34b, hsa-miR-34c, hsa-miR-373, hsa-miR-375, hsa-miR-410, hsa-miR-497, hsa-miR-615-5p, hsa-miR-630, hsa-miR-96, hsa-miR-132, let-7a, let-7a-1, let-7a-2, let-7a-3, let-7b, let-7c, let-7d, let-7e, let-7f-i, let-7f-2, let-7g, let-7i, hsa-miR-126, hsa-miR-135a, hsa-miR-144, hsa-miR-150, hsa-miR-16, hsa-miR-200a, hsa-miR-200b, hsa-miR-200c, hsa-miR-217, hsa-miR-218, hsa-miR-337, hsa-miR-494, and/or hsa-miR-98 inserted into the 5' UTR, intron and/or 3' UTR of one or more viral genes essential for viral replication.

In particular embodiments, a recombinant oncolytic virus for treating prostate cancer encodes a target antigen and comprises one or more copies of one or more tumor suppressive miR target sequences for let-7a-3p, let-7c, hsa-miR-100, hsa-miR-101, hsa-miR-105, hsa-miR-24, hsa-miR-128, hsa-miR-1296, hsa-miR-130b, hsa-miR-133a-1, hsa-miR-133a-2, hsa-miR-133b, hsa-miR-135a, hsa-miR-143-3p, hsa-miR-145-5p, hsa-miR-146a, hsa-miR-154, hsa-miR-15a, hsa-miR-187, hsa-miR-188-5p, hsa-miR-199b, hsa-miR-200b, hsa-miR-203, hsa-miR-205, hsa-miR-212, hsa-miR-218, hsa-miR-221, hsa-miR-224, hsa-miR-23a, hsa-miR-23b, hsa-miR-25, hsa-miR-26a, hsa-miR-26b, hsa-miR-29b, hsa-miR-302a, hsa-miR-30a, hsa-miR-30b, hsa-miR-30c-1, hsa-miR-30c-2, hsa-miR-30d, hsa-miR-30e, hsa-miR-31, hsa-miR-330, hsa-miR-331-3p, hsa-miR-34a, hsa-miR-34b, hsa-miR-34c, hsa-miR-374b, hsa-miR-449a, hsa-miR-4723-5p, hsa-miR-497, hsa-miR-628-5p, hsa-miR-642a-5p, hsa-miR-765, and/or hsa-miR-940 inserted into the 5' UTR, intron and/or 3' UTR of one or more viral genes essential for viral replication.

In particular embodiments, a recombinant oncolytic virus for treating retinoblastoma encodes a target antigen and comprises one or more copies of one or more tumor suppressive miR target sequences for hsa-miR-101, hsa-miR-183, hsa-miR-204, hsa-miR-34a, hsa-miR-365b-3p, hsa-miR-486-3p, and/or hsa-miR-532-5p inserted into the 5' UTR, intron and/or 3' UTR of one or more viral genes required for viral replication.

In particular embodiments, a recombinant oncolytic virus for treating glioblastoma encodes a target antigen and comprises one or more copies of one or more tumor suppressive miR target sequences for miR-143-3p, miR-133b, miR-1264, miR-448, miR-1298-5p, miR-490-5p, miR-138-2-3p, miR-144-3p, miR-144-5p, miR-150-5p, miR-129-1-3p, miR-559, miR-1-3-p, miR-143-5p, miR-223-3p, miR-3943, miR-338-3p, miR-124-3p, miR-219a-5p, miR-219a-2-3p, miR-451a, miR-142-5p, miR-133a-3p, miR-145-5p, and/or miR-145-5p inserted into the 5' UTR, intron and/or 3' UTR of one or more viral genes required for viral replication.

In particular embodiments, a recombinant oncolytic virus for treating head and neck cancer encodes a target antigen and comprises one or more copies of one or more tumor suppressive miR target sequences for miR-143-3p, miR-223-3p, miR-6080, miR-208b-3p, miR-206, miR-133a-5p, miR-133b, miR-199a-5p, miR-199b-5p, miR-145-5p, miR-150-5p, miR-142-3p, miR-144-3p, miR-144-5p, miR-338-3p, miR-214-3p, miR-559, miR-133a-3p, miR-1-3p, miR-126-3p, miR-142-5p, miR-451a, miR-199a-3p, and/or miR-199b-3p inserted into the 5' UTR, intron and/or 3' UTR of one or more viral genes required for viral replication.

In particular embodiments, a recombinant oncolytic virus for treating schwannoma encodes a target antigen and comprises one or more copies of one or more tumor suppressive miR target sequences for miR-13 3b, miR-208b-3p, miR-6130, miR-141-5p, miR-31-3p, miR-1293, miR-129-2-3p, miR-129-5p, miR-124-3p, miR-219a-5p, miR-219a-2-3p, miR-490-3p, miR-488-3p, miR-935, miR-122-3p, miR-122-

5p, miR-1-3p, miR-133a-3p, miR-375, miR-141-3p, miR-31-5p, miR-205-5p, miR-200c-3p, and/or miR-203a-3p inserted into the 5' UTR, intron and/or 3' UTR of one or more viral genes required for viral replication.

In particular embodiments, an oncolytic HSV-1 encodes a target antigen and comprises one or more tumor suppressor miR target sites selected from the group consisting of: hsa-miR-1-3p, hsa-miR-124-3p, hsa-miR-143-3p, hsa-miR-145-5p, hsa-miR-451a, and hsa-miR-559. In some embodiments, an oncolytic HSV-1 comprises one or more tumor suppressor miR target sites selected from the group consisting of: hsa-miR-1-3p, hsa-miR-124-3p, hsa-miR-143-3p, hsa-miR-145-5p, hsa-miR-451a, and hsa-miR-559 inserted into one or more viral genes essential for viral replication selected from the group consisting of: a 5' UTR, intron, and/or 3' UTR of an essential viral gene selected from the group consisting of: UL19, UL30, UL54 (ICP27), and one or both copies of ICP4. In some embodiments, an oncolytic HSV-1 comprises one or more tumor suppressor miR target sites selected from the group consisting of: hsa-miR-1-3p, hsa-miR-124-3p, hsa-miR-143-3p, hsa-miR-145-5p, hsa-miR-451a, and hsa-miR-559 inserted into one or more viral genes essential for viral replication selected from the group consisting of: a 5' UTR, intron, and/or 3' UTR of an essential viral gene selected from the group consisting of: UL54 (ICP27), and one or both copies of ICP4. Such oncolytic HSV-1 vectors are suitable for the treatment of solid cancers including but not limited to bladder cancer, breast cancer, brain cancer, colon cancer, glioblastoma, head and neck cancer, liver cancer, lung cancer, melanoma, pancreatic cancer, or a schwannoma.

In particular embodiments, an oncolytic HSV-1 encodes a target antigen and comprises one or more tumor suppressor miR target sites selected from the group consisting of: hsa-miR-1-3p, hsa-miR-124-3p, hsa-miR-145-5p, hsa-miR-451a, and hsa-miR-559. In some embodiments, an oncolytic HSV-1 comprises one or more tumor suppressor miR target sites selected from the group consisting of: hsa-miR-1-3p, hsa-miR-124-3p, hsa-miR-145-5p, hsa-miR-451a, and hsa-miR-559 inserted into one or more viral genes essential for viral replication selected from the group consisting of: a 5' UTR, intron, and/or 3' UTR of an essential viral gene selected from the group consisting of: UL19, UL30, UL54 (ICP27), and one or both copies of ICP4. In some embodiments, an oncolytic HSV-1 comprises one or more tumor suppressor miR target sites selected from the group consisting of: hsa-miR-1-3p, hsa-miR-124-3p, hsa-miR-145-5p, hsa-miR-451a, and hsa-miR-559 inserted into one or more viral genes essential for viral replication selected from the group consisting of: a 5' UTR, intron, and/or 3' UTR of an essential viral gene selected from the group consisting of: UL54 (ICP27), and one or both copies of ICP4. Such oncolytic HSV-1 vectors are suitable for the treatment of solid cancers including but not limited to bladder cancer, breast cancer, brain cancer, colon cancer, glioblastoma, head and neck cancer, liver cancer, lung cancer, melanoma, pancreatic cancer, or a schwannoma.

In particular embodiments, an oncolytic HSV-1 encodes a target antigen and comprises one or more tumor suppressor miR target sites selected from the group consisting of: hsa-miR-124-3p, hsa-miR-143-3p, hsa-miR-451a, and hsa-miR-559. In some embodiments, an oncolytic HSV-1 comprises one or more tumor suppressor miR target sites selected from the group consisting of: hsa-miR-124-3p, hsa-miR-143-3p, hsa-miR-451a, and hsa-miR-559 inserted into one or more viral genes essential for viral replication selected from the group consisting of: a 5' UTR, intron, and/or 3' UTR of an essential viral gene selected from the group consisting of: UL54 (ICP27), and one or both copies of ICP4. Such oncolytic HSV-1 vectors are suitable for the treatment of solid cancers including but not limited to bladder cancer, breast cancer, brain cancer, colon cancer, glioblastoma, head and neck cancer, liver cancer, lung cancer, melanoma, pancreatic cancer, or a schwannoma.

In particular embodiments, an oncolytic HSV-1 encodes a target antigen and comprises one or more tumor suppressor miR target sites selected from the group consisting of: hsa-miR-124-3p, hsa-miR-143-3p, hsa-miR-451a, and hsa-miR-559. In some embodiments, an oncolytic HSV-1 comprises one or more tumor suppressor miR target sites selected from the group consisting of: hsa-miR-124-3p, hsa-miR-143-3p, hsa-miR-451a, and hsa-miR-559 inserted into one or more viral genes essential for viral replication selected from the group consisting of: a 5' UTR, intron, and/or 3' UTR of an essential viral gene selected from the group consisting of: UL19, UL30, UL54 (ICP27), and one or both copies of ICP4. In some embodiments, an oncolytic HSV-1 comprises one or more tumor suppressor miR target sites selected from the group consisting of: hsa-miR-124-3p, hsa-miR-143-3p, hsa-miR-451a, and hsa-miR-559 inserted into one or more viral genes essential for viral replication selected from the group consisting of: a 5' UTR, intron, and/or 3' UTR of an essential viral gene selected from the group consisting of: UL54 (ICP27), and one or both copies of ICP4. Such oncolytic HSV-1 vectors are suitable for the treatment of solid cancers including but not limited to bladder cancer, breast cancer, brain cancer, colon cancer, glioblastoma, head and neck cancer, liver cancer, lung cancer, melanoma, pancreatic cancer, or a schwannoma.

In particular embodiments, an oncolytic HSV-1 encodes a target antigen and comprises one or more tumor suppressor miR target sites selected from the group consisting of: hsa-miR-124-3p, hsa-miR-145-5p, hsa-miR-451a, and hsa-miR-559. In some embodiments, an oncolytic HSV-1 comprises one or more tumor suppressor miR target sites selected from the group consisting of: hsa-miR-124-3p, hsa-miR-145-5p, hsa-miR-451a, and hsa-miR-559 inserted into one or more viral genes essential for viral replication selected from the group consisting of: a 5' UTR, intron, and/or 3' UTR of an essential viral gene selected from the group consisting of: UL19, UL30, UL54 (ICP27), and one or both copies of ICP4. In some embodiments, an oncolytic HSV-1 comprises one or more tumor suppressor miR target sites selected from the group consisting of: hsa-miR-124-3p, hsa-miR-145-5p, hsa-miR-451a, and hsa-miR-559 inserted into one or more viral genes essential for viral replication selected from the group consisting of: a 5' UTR, intron, and/or 3' UTR of an essential viral gene selected from the group consisting of: UL54 (ICP27), and one or both copies of ICP4. Such oncolytic HSV-1 vectors are suitable for the treatment of solid cancers including but not limited to bladder cancer, breast cancer, brain cancer, colon cancer, glioblastoma, head and neck cancer, liver cancer, lung cancer, melanoma, pancreatic cancer, or a schwannoma.

In particular embodiments, an oncolytic HSV-1 encodes a target antigen and comprises one or more tumor suppressor miR target sites selected from the group consisting of: hsa-miR-124-3p, hsa-miR-143-3p, and hsa-miR-145-5p. In some embodiments, an oncolytic HSV-1 comprises one or more tumor suppressor miR target sites selected from the group consisting of: hsa-miR-124-3p, hsa-miR-143-3p, and hsa-miR-145-5p inserted into one or more viral genes essential for viral replication selected from the group consisting of: a 5' UTR, intron, and/or 3' UTR of an essential viral gene selected from the group consisting of: UL19, UL30, UL54 (ICP27), and one or both copies of ICP4. In some embodiments, an oncolytic HSV-1 comprises one or more tumor suppressor miR target sites selected from the group consisting of: hsa-miR-124-3p, hsa-miR-143-3p, and hsa-miR-145-5p inserted into one or more viral genes essential for viral replication selected from the group consisting of: a 5' UTR, intron, and/or 3' UTR of an essential viral gene selected from the group consisting of: UL54 (ICP27), and one or both copies of ICP4. Such oncolytic HSV-1 vectors are suitable for the treatment of solid cancers including but not limited to bladder cancer, breast cancer, brain cancer, colon cancer, glioblastoma, head and neck cancer, liver cancer, lung cancer, melanoma, pancreatic cancer, or a schwannoma.

In particular embodiments, an oncolytic HSV-1 encodes a target antigen and comprises one or more tumor suppressor miR target sites selected from the group consisting of: hsa-miR-31-5p, hsa-miR-124-3p, hsa-miR-141-5p, and hsa-miR-205. In some embodiments, an oncolytic HSV-1 comprises one or more tumor suppressor miR target sites selected from the group consisting of: hsa-miR-31-5p, hsa-miR-124-3p, hsa-miR-141-5p, and hsa-miR-205 inserted into one or more viral genes essential for viral replication selected from the group consisting of: a 5' UTR, intron, and/or 3' UTR of an essential viral gene selected from the group consisting of: UL19, UL30, UL54 (ICP27), and one or both copies of ICP4. In some embodiments, an oncolytic HSV-1 comprises one or more tumor suppressor miR target sites selected from the group consisting of: hsa-miR-31-5p, hsa-miR-124-3p, hsa-miR-141-5p, and hsa-miR-205 inserted into one or more viral genes essential for viral replication selected from the group consisting of: a 5' UTR, intron, and/or 3' UTR of an essential viral gene selected from the group consisting of: UL54 (ICP27), and one or both copies of ICP4. Such oncolytic HSV-1 vectors are suitable for the treatment of solid cancers including but not limited to bladder cancer, breast cancer, brain cancer, colon cancer, glioblastoma, head and neck cancer, liver cancer, lung cancer, melanoma, pancreatic cancer, or a schwannoma.

In particular embodiments, an oncolytic HSV-1 encodes a target antigen and comprises one or more hsa-miR-1-3p tumor suppressor miR target sites. In some embodiments, an oncolytic HSV-1 comprises one or more hsa-miR-1-3p tumor suppressor miR target sites inserted into one or more viral genes essential for viral replication selected from the group consisting of: a 5' UTR, intron, and/or 3' UTR of an essential viral gene selected from the group consisting of: UL19, UL30, UL54 (ICP27), and one or both copies of ICP4. In some embodiments, an oncolytic HSV-1 comprises one or more hsa-miR-1-3p tumor suppressor miR target sites inserted into one or more viral genes essential for viral replication selected from the group consisting of: a 5' UTR, intron, and/or 3' UTR of an essential viral gene selected from the group consisting of: UL54 (ICP27), and one or both copies of ICP4. Such oncolytic HSV-1 vectors are suitable for the treatment of solid cancers including but not limited to bladder cancer, breast cancer, brain cancer, colon cancer, glioblastoma, head and neck cancer, liver cancer, lung cancer, melanoma, pancreatic cancer, or a schwannoma.

In particular embodiments, an oncolytic HSV-1 encodes a target antigen and comprises one or more hsa-miR-241-3p tumor suppressor miR target sites. In some embodiments, an oncolytic HSV-1 comprises one or more hsa-miR-124-3p tumor suppressor miR target sites inserted into one or more viral genes essential for viral replication selected from the group consisting of: a 5' UTR, intron, and/or 3' UTR of an essential viral gene selected from the group consisting of: UL19, UL30, UL54 (ICP27), and one or both copies of ICP4. In some embodiments, an oncolytic HSV-1 comprises one or more hsa-miR-124-3p tumor suppressor miR target sites inserted into one or more viral genes essential for viral replication selected from the group consisting of: a 5' UTR, intron, and/or 3' UTR of an essential viral gene selected from the group consisting of: UL54 (ICP27), and one or both copies of ICP4. Such oncolytic HSV-1 vectors are suitable for the treatment of solid cancers including but not limited to bladder cancer, breast cancer, brain cancer, colon cancer, glioblastoma, head and neck cancer, liver cancer, lung cancer, melanoma, pancreatic cancer, or a schwannoma.

In particular embodiments, an oncolytic HSV-1 encodes a target antigen and comprises one or more hsa-miR-143-3p tumor suppressor miR target sites. In some embodiments, an oncolytic HSV-1 comprises one or more hsa-miR-143-3p tumor suppressor miR target sites inserted into one or more viral genes essential for viral replication selected from the group consisting of: a 5' UTR, intron, and/or 3' UTR of an essential viral gene selected from the group consisting of: UL19, UL30, UL54 (ICP27), and one or both copies of ICP4. In some embodiments, an oncolytic HSV-1 comprises one or more hsa-miR-143-3p tumor suppressor miR target sites inserted into one or more viral genes essential for viral replication selected from the group consisting of: a 5' UTR, intron, and/or 3' UTR of an essential viral gene selected from the group consisting of: UL54 (ICP27), and one or both copies of ICP4. Such oncolytic HSV-1 vectors are suitable for the treatment of solid cancers including but not limited to bladder cancer, breast cancer, brain cancer, colon cancer, glioblastoma, head and neck cancer, liver cancer, lung cancer, melanoma, pancreatic cancer, or a schwannoma.

In particular embodiments, an oncolytic HSV-1 encodes a target antigen and comprises one or more hsa-miR-145-5p tumor suppressor miR target sites. In some embodiments, an oncolytic HSV-1 comprises one or more hsa-miR-145-5p tumor suppressor miR target sites inserted into one or more viral genes essential for viral replication selected from the group consisting of: a 5' UTR, intron, and/or 3' UTR of an essential viral gene selected from the group consisting of: UL19, UL30, UL54 (ICP27), and one or both copies of ICP4. In some embodiments, an oncolytic HSV-1 comprises one or more hsa-miR-145-5p tumor suppressor miR target sites inserted into one or more viral genes essential for viral replication selected from the group consisting of: a 5' UTR, intron, and/or 3' UTR of an essential viral gene selected from the group consisting of: UL54 (ICP27), and one or both copies of ICP4. Such oncolytic HSV-1 vectors are suitable for the treatment of solid cancers including but not limited to bladder cancer, breast cancer, brain cancer, colon cancer, glioblastoma, head and neck cancer, liver cancer, lung cancer, melanoma, pancreatic cancer, or a schwannoma.

In particular embodiments, an oncolytic HSV-1 encodes a target antigen and comprises one or more hsa-miR-451a tumor suppressor miR target sites. In some embodiments, an oncolytic HSV-1 comprises one or more hsa-miR-451a tumor suppressor miR target sites inserted into one or more viral genes essential for viral replication selected from the group consisting of: a 5' UTR, intron, and/or 3' UTR of an essential viral gene selected from the group consisting of: UL19, UL30, UL54 (ICP27), and one or both copies of ICP4. In some embodiments, an oncolytic HSV-1 comprises one or more hsa-miR-451a tumor suppressor miR target sites inserted into one or more viral genes essential for viral replication selected from the group consisting of: a 5' UTR, intron, and/or 3' UTR of an essential viral gene selected from the group consisting of: UL54 (ICP27), and one or both copies of ICP4. Such oncolytic HSV-1 vectors are suitable for the treatment of solid cancers including but not limited to bladder cancer, breast cancer, brain cancer, colon cancer, glioblastoma, head and neck cancer, liver cancer, lung cancer, melanoma, pancreatic cancer, or a schwannoma.

In particular embodiments, an oncolytic HSV-1 encodes a target antigen and comprises one or more hsa-miR-559 tumor suppressor miR target sites. In some embodiments, an oncolytic HSV-1 comprises one or more hsa-miR-559 tumor suppressor miR target sites inserted into one or more viral genes essential for viral replication selected from the group consisting of: a 5' UTR, intron, and/or 3' UTR of an essential viral gene selected from the group consisting of: UL19, UL30, UL54 (ICP27), and one or both copies of ICP4. In some embodiments, an oncolytic HSV-1 comprises one or more hsa-miR-559 tumor suppressor miR target sites inserted into one or more viral genes essential for viral replication selected from the group consisting of: a 5' UTR, intron, and/or 3' UTR of an essential viral gene selected from the group consisting of: UL54 (ICP27), and one or both copies of ICP4. Such oncolytic HSV-1 vectors are suitable for the treatment of solid cancers including but not limited to bladder cancer, breast cancer, brain cancer, colon cancer, glioblastoma, head and neck cancer, liver cancer, lung cancer, melanoma, pancreatic cancer, or a schwannoma.

F. Engineered Antigen Receptors

In particular embodiments, immune effector cells are modified to express an engineered antigen receptor that recognizes or binds a target antigen that is ectopically expressed on a target cell or exogenously expressed on a target cell. In various embodiments, an oncolytic virus is used to ectopically express a target antigen on a target cell or exogenously express a target antigen on a target cell.

In particular embodiments, the engineered antigen receptor is an engineered αβ T cell receptor (αβTCR), an engineered γδ TCR, a chimeric antigen receptor (CAR), an engineered NKG2D, or a Daric receptor or components thereof.

1. Engineered TCRs

Naturally occurring T cell receptors comprise two subunits, an alpha chain and a beta chain subunit (αβTCR), or a gamma chain and a delta chain subunit (γδTCR), each of which is a unique protein produced by recombination event in each T cell's genome. Libraries of TCRs may be screened for their selectivity to particular target antigens. In this manner, natural TCRs, which have a high-avidity and reactivity toward target antigens may be selected, cloned, and subsequently introduced into a population of immune effector cells used for adoptive immunotherapy. In one embodiment, the TCR is an αβTCR. In one embodiment, the TCR is a γδTCR.

In one embodiment, T cells are modified by introducing a TCR subunit that has the ability to form TCRs that confer specificity to T cells for tumor cells expressing a target antigen. In particular embodiments, the subunits have one or more amino acid substitutions, deletions, insertions, or modifications compared to the naturally occurring subunit, so long as the subunits retain the ability to form TCRs and confer upon transfected T cells the ability to home to target cells, and participate in immunologically-relevant cytokine signaling. The engineered TCRs preferably also bind target cells displaying the relevant tumor-associated peptide with high avidity, and optionally mediate efficient killing of target cells presenting the relevant peptide in vivo.

The nucleic acids encoding engineered TCRs are preferably isolated from their natural context in a (naturally-occurring) chromosome of a T cell, and can be incorporated into suitable vectors as described elsewhere herein. Both the nucleic acids and the vectors comprising them can be transferred into a cell, preferably a T cell in particular embodiments. The modified T cells are then able to express one or more chains of a TCR encoded by the transduced nucleic acid or nucleic acids. In preferred embodiments, the engineered TCR is an exogenous TCR because it is introduced into T cells that do not normally express the particular TCR. The essential aspect of the engineered TCRs is that it has high avidity for a tumor antigen presented by a major histocompatibility complex (MHC) or similar immunological component. In contrast to engineered TCRs, CARs are engineered to bind target antigens in an MHC independent manner.

The TCR can be expressed with additional polypeptides attached to the amino-terminal or carboxyl-terminal portion of the alpha chain or beta chain of a TCR, or of the gamma chain or delta chain of a TCR so long as the attached additional polypeptide does not interfere with the ability of the alpha chain or beta chain to form a functional T cell receptor and the MHC dependent antigen recognition.

Target antigens that are recognized by the engineered TCRs contemplated in particular embodiments include, but are not limited to cancer antigens, including antigens on both hematological cancers and solid tumors. Illustrative target antigens that can be targeted by TCRs contemplated herein include, but are not limited to FRα, α$_v$β$_6$ integrin, BCMA, CD276, B7-H6, CAIX, CD16, CD19, CD20, CD22, CD30, CD33, CD37, CD38, CD44, CD44v6, CD44v7/8, CD70, CD79a, CD79b, CD123, CD133, CD138, CD171, CEA, CLL-1, CS-1, CSPG4, CTAGE1, EGFR, EGFRvIII, EGP2, EGP40, EPCAM, EPHA2, FAP, FCRL5, AchR, GD2, GD3, GPC3, HER2, IL-11Rα, IL-13Rα2, LAGE-1A, Lambda, LeY, L1-CAM, MAGE-A1, MAGE-A3, MAGE-A4, MAGE-A6, MAGEA10, MelanA or MART1, MSLN, MUC1, MUC16, MICA, MICB, NCAM, NY-ESO-1, PLAC1, PRAME, PSCA, PSMA, ROR1, SSX2, Survivin, TAG72, TEM1/CD248, TEM7R, TPBG, ULBP1, ULBP2, ULBP3, ULBP4, ULBP5, ULBP6, VEGFR2, and WT-1.

2. Chimeric Antigen Receptors (CARs)

In various embodiments, immune effector cells are modified to express chimeric antigen receptors (CARs) that redirect cytotoxicity toward a target antigen that is ectopically expressed on a target cell or exogenously expressed on a target cell. CARs are molecules that combine antibody-based specificity for a target antigen with a T cell receptor-activating intracellular domain to generate a chimeric protein that exhibits a specific anti-tumor cellular immune activity. As used herein, the term, "chimeric," describes being composed of parts of different proteins or DNAs from different origins. In one embodiment, T cells are engineered by introducing a polynucleotide or vector encoding a CAR.

In various embodiments, a CAR comprises an extracellular antigen binding domain that binds to a specific target antigen, a transmembrane domain and one ore more intracellular signaling domains. The main characteristic of CARs is their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific coreceptors.

In particular embodiments, CARs comprise an extracellular antigen binding domain that specifically binds to a target polypeptide. An antigen binding domain includes any naturally occurring, synthetic, semi-synthetic, or recombinantly produced binding partner for a biological molecule of interest.

In particular embodiments, the extracellular binding domain comprises an antibody or antigen binding fragment thereof.

In one preferred embodiment, the binding domain is an scFv.

In another preferred embodiment, the binding domain is a camelid antibody.

In particular embodiments, the CAR comprises an extracellular domain that binds an antigen selected from the group consisting of: FRα, $α_vβ_6$ integrin, BCMA, CD276, B7-H6, CAIX, CD16, CD19, CD20, CD22, CD30, CD33, CD37, CD38, CD44, CD44v6, CD44v7/8, CD70, CD79a, CD79b, CD123, CD133, CD138, CD171, CEA, CLL-1, CS-1, CSPG4, CTAGE1, EGFR, EGFRvIII, EGP2, EGP40, EPCAM, EPHA2, FAP, FCRL5, AchR, GD2, GD3, GPC3, HER2, IL-11Rα, IL-13Rα2, LAGE-1A, Lambda, LeY, L1-CAM, MAGE-A1, MAGE-A3, MAGE-A4, MAGE-A6, MAGEA10, MelanA or MART1, MSLN, MUC1, MUC16, MICA, MICB, NCAM, NY-ESO-1, PLAC1, PRAME, PSCA, PSMA, ROR1, SSX2, Survivin, TAG72, TEM1/CD248, TEM7R, TPBG, ULBP1, ULBP2, ULBP3, ULBP4, ULBP5, ULBP6, VEGFR2, and WT-1.

In particular embodiments, a CAR comprises a spacer domain. In one embodiment, the spacer domain comprises the CH2 and CH3 of IgG1, IgG4, or IgD.

In particular embodiments, a CAR comprises a hinge region. Illustrative hinge domains suitable for use in the CARs described herein include the hinge region derived from the extracellular regions of type 1 membrane proteins such as CD8α, and CD4, which may be wild-type hinge regions from these molecules or may be altered. In another embodiment, the hinge domain comprises a CD8α hinge region.

The transmembrane (TM) domain of the CAR fuses the extracellular binding portion and intracellular signaling domain and anchors the CAR to the plasma membrane of the immune effector cell. The TM domain may be derived either from a natural, synthetic, semi-synthetic, or recombinant source.

Illustrative TM domains may be derived from (i.e., comprise at least the transmembrane region(s) of the alpha, beta, gamma, or delta chain of the T-cell receptor, CD3δ, CD3δ, CD3γ, CD3ζ, CD4, CD5, CD8α, CD9, CD 16, CD22, CD27, CD28, CD33, CD37, CD45, CD64, CD80, CD86, CD 134, CD137, CD152, CD154, AMN, and PD-1.

In one embodiment, a CAR comprises a TM domain derived from CD8α. In another embodiment, a CAR contemplated herein comprises a TM domain derived from CD8α and a short oligo- or polypeptide linker, preferably between 1, 2, 3, 4, 5, 6, 7, 8, 9, or 10 amino acids in length that links the TM domain and the intracellular signaling domain of the CAR. A glycine-serine linker provides a particularly suitable linker.

In preferred embodiments, a CAR comprises an intracellular signaling domain that comprises one or more "co-stimulatory signaling domains" and a "primary signaling domain."

Primary signaling domains that act in a stimulatory manner may contain signaling motifs which are known as immunoreceptor tyrosine-based activation motifs or ITAMs.

Illustrative examples of ITAM containing primary signaling domains suitable for use in CARs contemplated in particular embodiments include those derived from FcRγ, FcRβ, CD3γ, CD3δ, CD3ε, CD3ζ, CD22, CD79a, CD79b, and CD66d. In particular preferred embodiments, a CAR comprises a CD3ζ primary signaling domain and one or more co-stimulatory signaling domains. The intracellular primary signaling and co-stimulatory signaling domains may be linked in any order in tandem to the carboxyl terminus of the transmembrane domain.

In particular embodiments, a CAR comprises one or more co-stimulatory signaling domains to enhance the efficacy and expansion of T cells expressing CAR receptors.

Illustrative examples of such co-stimulatory molecules suitable for use in CARs contemplated in particular embodiments include TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70. In one embodiment, a CAR comprises one or more co-stimulatory signaling domains selected from the group consisting of CD28, CD137, and CD134, and a CD3ζ primary signaling domain.

In various embodiments, the CAR comprises: an extracellular domain that binds an antigen selected from the group consisting of: BCMA, CD19, CD20, CD22, or CD38; a transmembrane domain isolated from a polypeptide selected from the group consisting of: CD4, CD8α, CD154, and PD-1; one or more intracellular co-stimulatory signaling domains isolated from a polypeptide selected from the group consisting of: CD28, CD134, and CD137; and a signaling domain isolated from a polypeptide selected from the group consisting of: FcRγ, FcRβ, CD3γ, CD3δ, CD3ε, CD3ζ, CD22, CD79a, CD79b, and CD66d.

3. NKG2D

In various embodiments, immune effector cells are modified to express the immune cell activating receptor natural-killer group 2, member D (NKG2D). NKG2D belongs to the family of C-type lectin-like receptors. NKG2D is expressed by all NK cells, most NKT cells, all CD8+ T cells and subsets of γδ' T cells. NKG2D is a type II transmembrane protein and does not contain any known signaling motif within its intracellular domain. For signal transduction, NKG2D associates, like many other activating receptors, with adaptor proteins via charged residues in its transmembrane domain. NKG2D forms a complex with DNAX-activating protein of 10 kDa (DAP10) to activate immune effector cells. In particular embodiments, immune effector cells are modified to express NKG2D. In certain embodiments, immune effector cells are modified to express NKG2D and DAP10. NKG2D ligands are rarely detectable on the surface of healthy cells and tissues, but are frequently expressed on stressed and/or rapidly proliferating cells, which includes tumor- and pathogen-infected cells.

In particular embodiments, an oncolytic virus is used to express an NKG2D ligand in a target cell. Illustrative examples of NKG2D ligands suitable for expressing in target cells include, but are not limited to MICA, MICB, ULBP1, ULBP2, ULBP3, ULBP4, ULBP5, and ULBP6, VEGFR2.

4. Daric Receptors

In particular embodiments, immune effector cells are modified to express one or more DARIC receptor components that recognize or bind a target antigen that is ectopically expressed on a target cell or exogenously expressed on a target cell. As used herein, the term "DARIC receptor" refers to one or more non-naturally occurring polypeptides that transduces an immunostimulatory signal in an immune effector cell upon exposure to a multimerizing agent or bridging factor, e.g., stimulating immune effector cell activity and function, increasing production and/or secretion of proinflammatory cytokines. In preferred embodiments, the DARIC receptor is a multi-chain receptor comprising a DARIC signaling component and a DARIC binding component.

A "DARIC signaling component" or "DARIC signaling polypeptide" refers to a polypeptide comprising one or more multimerization domains, a transmembrane domain, and an intracellular signaling domain. In particular embodiments, the DARIC signaling component comprises a multimerization domain, a transmembrane domain, a co-stimulatory domain and/or a primary signaling domain.

Illustrative examples of multimerization domains suitable for use in particular DARIC signaling components contemplated herein include, but are not limited to, an FK506 binding protein (FKBP) polypeptide or variants thereof, or an FKBP-rapamycin binding (FRB) polypeptide or variants thereof. In particular preferred embodiments, a DARIC signaling component comprises an FRB polypeptide comprising a T2098L mutation, or variant thereof. In certain preferred embodiments, a DARIC signaling component comprises an FKBP12 polypeptide or variant thereof.

Illustrative examples of transmembrane domains suitable for use in particular DARIC signaling components contemplated herein include, but are not limited to, the transmembrane region(s) of the alpha, beta, gamma, or delta chain of a T-cell receptor, CD3ε, CD3ζ, CD4, CD5, CD8α, CD9, CD 16, CD22, CD27, CD28, CD33, CD37, CD45, CD64, CD71, CD80, CD86, CD 134, CD137, CD152, CD 154, AMN, and PD1. In particular preferred embodiments, a DARIC signaling component comprises a CD8α transmembrane domain. In certain preferred embodiments, an DARIC signaling component comprises a CD4 transmembrane domain.

In various preferred embodiments, a short oligo- or polypeptide linker, preferably between 1, 2, 3, 4, 5, 6, 7, 8, 9, or 10 amino acids in length links the transmembrane domain and the intracellular signaling domain. A glycine-serine based linker provides a particularly suitable linker.

DARIC signaling components contemplate herein comprise one or more intracellular signaling domains. In one embodiment, a DARIC signaling component comprises one or more co-stimulatory signaling domains and/or a primary signaling domain. In one embodiment, the intracellular signaling domain comprises an immunoreceptor tyrosine activation motif (ITAM).

Illustrative examples of ITAM containing primary signaling domains that are suitable for use in particular DARIC signaling components contemplated herein include, but are not limited to those derived from FcRγ, FcRβ, CD3γ, CD3δ, CD3ε, CD3ζ, CD22, CD79a, CD79b, and CD66d. In particular preferred embodiments, an NKG2D DARIC signaling component comprises a CD3ζ primary signaling domain and one or more co-stimulatory signaling domains. The primary signaling and co-stimulatory signaling domains may be linked in any order in tandem to the carboxyl terminus of the transmembrane domain.

Illustrative examples of such co-stimulatory molecules suitable for use in particular DARIC signaling components contemplated herein include, but are not limited to, TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70. In particular embodiments, an DARIC signaling component comprises one or more co-stimulatory signaling domains selected from the group consisting of CD28, CD137, and CD134. In particular embodiments, an DARIC signaling component comprises one or more co-stimulatory signaling domains selected from the group consisting of CD28, CD137, and CD134, and a CD3ζ primary signaling domain. In particular preferred embodiments, an DARIC signaling component comprises a CD137 co-stimulatory domain and a CD3ζ primary signaling domain.

In certain preferred embodiments, a DARIC signaling component comprises an FRB T2098L multimerization domain, a CD8α transmembrane domain, a CD137 co-stimulatory domain and a CD3ζ primary signaling domain.

A "DARIC binding component" or "DARIC binding polypeptide" refers to a polypeptide comprising an extracellular antigen binding domain, one or more multimerization domains, a transmembrane domain, and an intracellular signaling domain.

In particular embodiments, the extracellular binding domain of a DARIC binding component is an antibody or antigen binding fragment thereof including, but not limited to a Camel Ig, Ig NAR, Fab fragments, Fab' fragments, F(ab)'2 fragments, F(ab)'3 fragments, Fv, single chain variable fragments ("scFv"), bis-scFv, (scFv)2, minibodies, diabodies, triabodies, tetrabodies, disulfide stabilized Fv proteins ("dsFv"), or a single-domain antibody (sdAb, Nanobody.

In particular embodiments, the DARIC binding component comprises an extracellular domain that binds an antigen selected from the group consisting of: FRα, α$_v$β$_6$ integrin, BCMA, CD276, B7-H6, CAIX, CD16, CD19, CD20, CD22, CD30, CD33, CD37, CD38, CD44, CD44v6, CD44v7/8, CD70, CD79a, CD79b, CD123, CD133, CD138, CD171, CEA, CLL-1, CS-1, CSPG4, CTAGE1, EGFR, EGFRvIII, EGP2, EGP40, EPCAM, EPHA2, FAP, FCRL5, AchR, GD2, GD3, GPC3, HER2, IL-11Rα, IL-13Rα2, LAGE-1A, Lambda, LeY, L1-CAM, MAGE-A1, MAGE-A3, MAGE-A4, MAGE-A6, MAGEA10, MelanA or MART1, MSLN, MUC1, MUC16, MICA, MICB, NCAM, NY-ESO-1, PLAC1, PRAME, PSCA, PSMA, ROR1, SSX2, Survivin, TAG72, TEM1/CD248, TEM7R, TPBG, ULBP1, ULBP2, ULBP3, ULBP4, ULBP5, ULBP6, VEGFR2, and WT-1.

Illustrative examples of multimerization domains suitable for use in particular DARIC binding components contemplated herein include, but are not limited to, an FK506 binding protein (FKBP) polypeptide or variants thereof, or an FKBP-rapamycin binding (FRB) polypeptide or variants thereof. In particular preferred embodiments, a DARIC signaling component comprises an FKBP12 polypeptide or variant thereof. In certain preferred embodiments, a DARIC signaling component comprises an FRB polypeptide comprising a T2098L mutation, or variant thereof.

Illustrative examples of transmembrane domains suitable for use in particular DARIC binding components contemplated herein include, but are not limited to, the transmembrane region(s) of the alpha, beta, gamma, or delta chain of a T-cell receptor, CD3ε, CD3ζ, CD4, CD5, CD8α, CD9, CD 16, CD22, CD27, CD28, CD33, CD37, CD45, CD64, CD71, CD80, CD86, CD 134, CD137, CD152, CD 154, AMN, and PD1. In particular preferred embodiments, a DARIC binding component comprises a CD4 transmembrane domain. In certain preferred embodiments, a DARIC binding component comprises a CD8α transmembrane domain.

In various preferred embodiments, a short oligo- or polypeptide linker, preferably between 1, 2, 3, 4, 5, 6, 7, 8, 9, or 10 amino acids in length links the transmembrane domain and the intracellular signaling domain. A glycine-serine based linker provides a particularly suitable linker.

In particular embodiments, the DARIC binding components contemplated herein comprise a signal peptide, e.g., secretion signal peptide, and do not comprise a transmembrane domain. Illustrative examples of signal peptides suitable for use in particular DARIC binding components include, but are not limited to an IgG1 heavy chain signal polypeptide, an Igκ light chain signal polypeptide, a CD8α signal polypeptide, or a human GM-CSF receptor alpha signal polypeptide. In various preferred embodiments, an DARIC binding component comprises a CD8α signal polypeptide.

In particular preferred embodiments, a DARIC binding component comprises an scFv or single domain antibody that binds a target antigen, an FKBP12 multimerization domain, and a CD4 transmembrane domain.

Bridging factors contemplated herein mediate or promote the association of DARIC signaling components with DARIC binding components through the component multimerization domains. A bridging factor associates with and is disposed between the multimerization domains to promote association of a DARIC signaling component and an DARIC binding component. In the presence of a bridging factor, the binding component and the signaling component associate and initiate immune effector cell activity against a target cell when the DARIC binding polypeptide is bound to a target antigen on the target cell. In the absence of a bridging factor, the DARIC binding component does not associate with the DARIC signaling component.

In particular embodiments, a DARIC signaling component and a DARIC binding component comprise one or more FRB and/or FKBP multimerization domains or variants thereof. In certain embodiments, a DARIC signaling component comprises an FRB multimerization domain or variant thereof and a DARIC binding component comprises an FKBP multimerization domains or variant thereof. In particular preferred embodiments, a DARIC signaling component comprises an FRB T2098L multimerization domain or variant thereof and a DARIC binding component comprises an FKBP12 or FKBP12 F36V multimerization domains or variant thereof.

Illustrative examples of bridging factors suitable for use in particular embodiments contemplated herein include, but are not limited to, AP1903, AP20187, AP21967 (also known as C-16-(S)-7-methylindolerapamycin), everolimus, novolimus, pimecrolimus, ridaforolimus, tacrolimus, temsirolimus, umirolimus, and zotarolimus. In particular preferred embodiments, the bridging factor is AP21967. In certain preferred embodiments, the bridging factor is sirolimus (rapamycin).

G. Immune Effector Cells

In various embodiments, a subject is administered immune effector cells modified with an engineered antigen receptor that binds a target antigen ectopically or exogenously expressed on one or more target cells. As used herein, the term "genetically engineered" or "genetically modified" refers to the addition of extra genetic material in the form of DNA or RNA into the total genetic material in a cell. The terms, "genetically modified cells," "modified cells," and "redirected cells," are used interchangeably in particular embodiments.

An "isolated cell" refers to a non-naturally occurring cell, e.g., a cell that does not exist in nature, a modified cell, an engineered cell, etc., that has been obtained from an in vivo tissue or organ and is substantially free of extracellular matrix.

As used herein, the term "population of cells" refers to a plurality of cells that may be made up of any number and/or combination of homogenous or heterogeneous cell types, as described elsewhere herein. For example, for transduction of immune effector cells, a population of cells may be isolated or obtained from peripheral blood. A population of cells may comprise about 10%, about 20%, about 30%, about 40%, about 50%, about 60%, about 70%, about 80%, about 90%, or about 100% of the target cell type. In certain embodiments, T cells may be isolated or purified from a population of heterogeneous cells using methods known in the art.

An "immune effector cell," is any cell of the immune system that has one or more effector functions (e.g., cytotoxic cell killing activity, secretion of cytokines, induction of ADCC and/or CDC). The illustrative immune effector cells contemplated herein include, but are not limited to T lymphocytes, in particular cytotoxic T cells (CTLs; CD8+ T cells), TILs, helper T cells (HTLs; CD4+ T cells), αβTCR T cells, and γδTCR T cells; natural killer (NK) cells; and natural killer T (NKT) cells. Immune effector cells can be autologous/autogeneic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are autologous.

Illustrative immune effector cells used in particular embodiments contemplated herein include T lymphocytes. The terms "T cell" or "T lymphocyte" are art-recognized and are intended to include in particular embodiments, without limitation, thymocytes, immature T lymphocytes, mature T lymphocytes, resting T lymphocytes, αβTCR$^+$ T lymphocytes, γδTCR$^+$ T lymphocytes, and activated T lymphocytes. In particular embodiments, T cell can be a T helper (Th) cell, for example a T helper 1 (Th1) or a T helper 2 (Th2) cell. The T cell can be a helper T cell (CD4$^+$ T cell), regulatory CD4$^+$ T cell, a cytotoxic T cell (CTL; CD8$^+$ T cell), CD4$^+$CD8$^+$ T cell, CD4$^-$CD8$^-$ T cell, or any other subset of T cells. Other illustrative populations of T cells suitable for use in particular embodiments include naïve T cells and central memory T cells.

As would be understood by the skilled person, other immune effector cells can be used in particular embodiments contemplated herein including but not limited to NK cells, NKT cells, neutrophils, and macrophages. Immune effector cells may also include progenitors of effector cells wherein such progenitor cells can be induced to differentiate into an immune effector cells in vivo or in vitro. Thus, in particular embodiments, immune effector cells include progenitors of immune effectors such as hematopoietic stem cells (HSCs) contained within the CD34$^+$ population of cells derived from cord blood, bone marrow or mobilized peripheral blood which upon administration in a subject differentiate into mature immune effector cells, or which can be induced in vitro to differentiate into mature immune effector cells.

Immune effector cells modified to express an engineered antigen receptor are provided in particular embodiments. In particular embodiments, immune effector cells are harvested from a subject, modified to express an engineered antigen receptor, cultured and reintroduced into the subject. In particular embodiments, immune effector cells are harvested from a subject that has been treated with an oncolytic virus to express one or more target antigens on one or more target cells, modified to express an engineered antigen receptor, cultured and reintroduced into the subject. In particular embodiments, a subject that has been treated with an oncolytic virus to express one or more target antigens on one or more target cells, immune effector cells comprising T cells specific to the target antigen, T cells specific to the target cells, non-specific T cells, αβTCR$^+$ T cells, γδTCR$^+$ T cells and/or NK cells are harvested from the subject, modified to express an engineered antigen receptor, cultured and reintroduced into the subject.

In particular embodiments, prior to in vitro manipulation or modification of the immune effector cells described herein, the source of cells is obtained or harvested from a subject treated with one or more administrations of an oncolytic virus. In particular embodiments, the modified immune effector cells comprise T cells and/or NK cells. immune effector cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors.

In certain embodiments, immune effector cells can be obtained from a unit of blood collected from a subject using any number of techniques known to the skilled person, such as sedimentation, e.g., FICOLL™ separation.

In other embodiments, an isolated or purified population of immune effector cells is used. In some embodiments, after isolation of PBMC, both cytotoxic and helper T lymphocytes can be sorted into naïve, memory, and effector T cell subpopulations either before or after activation, expansion, and/or genetic modification.

A specific subpopulation of T cells, expressing one or more of the following markers: CD3, CD4, CD8, CD28, CD45RA, CD45RO, CD62, CD127, and HLA-DR can be further isolated by positive or negative selection techniques. In one embodiment, a specific subpopulation of T cells, expressing one or more of the markers selected from the group consisting of CD62L, CCR7, CD28, CD27, CD122, CD127, CD197; or CD38 or CD62L, CD127, CD197, and CD38, is further isolated by positive or negative selection techniques. In various embodiments, the manufactured T cell compositions do not express or do not substantially express one or more of the following markers: CD57, CD244, CD160, PD-1, CTLA4, TIM3, and LAG3. In one embodiment, an isolated or purified population of T cells expresses one or more of the markers including, but not limited to a CD3$^+$, CD4$^+$, CD8$^+$, or a combination thereof.

In certain embodiments, the immune effector cells are isolated from an individual and first activated and stimulated to proliferate in vitro prior to being modified to express an engineered antigen receptor.

In order to achieve sufficient therapeutic doses of immune effector cell compositions, the cells are often subjected to one or more rounds of stimulation, activation and/or expansion. Immune effector cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety. In particular embodiments, T cells are activated and expanded for about 6 hours, about 12 hours, about 18 hours or about 24 hours prior to introduction of vectors or mRNAs encoding an engineered antigen receptor. In one embodiment, T cells are activated at the same time that they are modified.

In various embodiments, a method of generating an immune effector cell that expresses an engineered antigen receptor comprises activating a population by providing a primary stimulation signal through the T cell TCR/CD3 complex and by providing a secondary costimulation signal through an accessory molecule, e.g., CD28; and modifying the cells by introducing a vector or mRNA encoding an engineered antigen receptor. In particular embodiments, PBMCs or isolated T cells are contacted with a stimulatory agent and costimulatory agent, such as anti-CD3 and anti-CD28 antibodies, generally attached to a bead or other surface, in a culture medium with appropriate cytokines, such as IL-2, IL-7, and/or IL-15.

The TCR/CD3 complex may be stimulated by contacting the T cell with a suitable CD3 binding agent, e.g., a CD3 ligand or an anti-CD3 monoclonal antibody. Illustrative examples of CD3 antibodies include, but are not limited to, OKT3, G19-4, BC3, and 64.1. In addition to the primary stimulation signal provided through the TCR/CD3 complex, induction of T cell responses requires a second, costimulatory signal. In particular embodiments, a CD28 binding agent can be used to provide a costimulatory signal. Illustrative examples of CD28 binding agents include but are not limited to: natural CD 28 ligands, e.g., a natural ligand for CD28 (e.g., a member of the B7 family of proteins, such as B7-1(CD80) and B7-2 (CD86); and anti-CD28 monoclonal antibody or fragment thereof capable of crosslinking the CD28 molecule, e.g., monoclonal antibodies 9.3, B-T3, XR-CD28, KOLT-2, 15E8, 248.23.2, and EX5.3D10.

In one embodiment, expanding T cells activated and modified to express an engineered antigen receptor further comprises culturing a population of cells comprising T cells for several hours (about 3 hours) to about 7 days to about 28 days or any hourly integer value in between. In another embodiment, the T cell composition may be cultured for 14 days. In a particular embodiment, T cells are cultured for about 21 days. In another embodiment, the T cell compositions are cultured for about 2-3 days.

In particular embodiments, conditions appropriate for T cell culture include an appropriate media (e.g., Minimal Essential Media or RPMI Media 1640 or, X-vivo 15, (Lonza)) and one or more factors necessary for proliferation and viability including, but not limited to serum (e.g., fetal bovine or human serum), interleukin-2 (IL-2), insulin, IFN-γ, IL-4, IL-7, IL-21, GM-CSF, IL-10, IL-12, IL-15, TGFβ, and TNF-α or any other additives suitable for the growth of cells known to the skilled artisan.

Further illustrative examples of cell culture media include, but are not limited to RPMI 1640, Clicks, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells.

In a particular embodiment, polynucleotide encoding an engineered antigen receptor is introduced into the population of T cells. The polynucleotides may be introduced into the T cells by microinjection, transfection, lipofection, heat-shock, electroporation, transduction, gene gun, microinjection, DEAE-dextran-mediated transfer, and the like.

In a preferred embodiment, polynucleotides are introduced into a T cell by viral transduction.

Illustrative examples of viral vector systems suitable for introducing a polynucleotide into an immune effector cell or CD34+ cell include, but are not limited to adeno-associated virus (AAV), retrovirus, herpes simplex virus, adenovirus, vaccinia virus vectors for gene transfer.

In one embodiment, polynucleotides are introduced into a T cell by AAV transduction.

In one embodiment, polynucleotides are introduced into a T cell by retroviral transduction.

In one embodiment, polynucleotides are introduced into a T cell by lentiviral transduction.

In one embodiment, polynucleotides are introduced into a T cell by adenovirus transduction.

In addition to being modified to express an engineered antigen receptor, immune effector cells may comprise one or more gene edits to increase the anti-tumor properties of the cells. In particular embodiments, one or more immune effector cells may be edited by a homing endonuclease, megaTAL, TALEN, zinc finger nuclease, that disrupts alloreactivity and/or a checkpoint signaling pathway. Illustrative examples of genes that are suitable for editing in particular embodiments contemplated herein include, but are not limited to TCRα, TCRβ, PD-1, CBLB, TIM3, TIGIT, CTLA4, LAG3, TGFβRI, and TGFβRII.

Immune effector cells may also be modified to express one or more other polypeptides that enhance the anti-tumor potency of the cells including, but not limited to BiTEs; cytokines including but not limited to IL-2, insulin, IFN-γ, IL-7, IL-21, IL-10, IL-12, IL-15, and TNF-α; chemokines including but not limited to MIP-1α, MIP-10, MCP-1, MCP-3, and RANTES; cytoxins including but not limited to Perforin, Granzyme A, and Granzyme B; and cytokine receptors including but not limited to an IL-2 receptor, an IL-7 receptor, an IL-12 receptor, an IL-15 receptor, and an IL-21 receptor.

Immune effector cells may also be modified to express one or more flip receptors that enhance the anti-tumor potency of the cells. As used herein, the term "flip receptor" refers to a non-naturally occurring polypeptide that converts the immunosuppressive signals from the tumor microenvironment to an immunostimulatory signal in a T cell. In preferred embodiments, a flip receptor refers to a polypeptide that comprises an exodomain that binds an immunosuppressive factor, a transmembrane domain, and an endodomain that transduces an immunostimulatory signal to a T cell.

In one embodiment, the donor repair template encodes a flip receptor comprising an exodomain or extracellular binding domain that binds an immunosuppressive cytokine, a transmembrane domain, and an endodomain of an immunopotentiating cytokine receptor.

In particular embodiments, a flip receptor comprises an exodomain that binds an immunosuppressive cytokine is the extracellular cytokine binding domain of an IL-4 receptor, IL-6 receptor, IL-8 receptor, IL-10 receptor, IL-13 receptor, TGFβ receptor 1, or TGFβ receptor 2; a transmembrane isolated from CD4, CD8α, CD27, CD28, CD134, CD137, CD3, TGFβ receptor 1, TGFβ receptor 2, IL-2 receptor, IL-7 receptor, IL-12 receptor, IL-15 receptor, or IL-21 receptor; and an endodomain isolated from IL-2 receptor, IL-7 receptor, IL-12 receptor, IL-15 receptor, or IL-21 receptor.

In particular embodiments, a flip receptor comprises an exodomain that binds an immunosuppressive cytokine is an antibody or antigen binding fragment thereof that binds IL-4, IL-6, IL-8, IL-10, IL-13, TGFβ receptor 1, or TGFβ receptor 2; a transmembrane isolated from CD4, CD88a, CD27, CD28, CD134, CD137, a CD3, TGFβ receptor 1, or TGFβ receptor 2, IL-2 receptor, IL-7 receptor, IL-12 receptor, IL-15 receptor, or IL-21 receptor; and an endodomain isolated from an IL-2 receptor, IL-7 receptor, IL-12 receptor, IL-15 receptor, or IL-21 receptor.

In one embodiment, the donor repair template comprises a flip receptor comprising an exodomain that binds an immunosuppressive factor, a transmembrane domain, and one or more intracellular co-stimulatory signaling domains and/or primary signaling domains.

Illustrative examples of exodomains suitable for use in particular embodiments of flip receptors contemplated in particular embodiments include, but are not limited to: an extracellular ligand binding domain of a receptor that comprises an ITIM and/or an ITSM.

Further illustrative examples of exodomains suitable for use in particular embodiments of flip receptors contemplated in particular embodiments include, but are not limited to an extracellular ligand binding domain of: PD-1, LAG-3, TIM-3, CTLA-4, BTLA, CEACAM1, TIGIT, TGFβRI, TGFβRII, IL4R, IL6R, CXCR1, CXCR2, IL10R, IL13Rα2, TRAILR1, RCAS1R, and FAS.

In one embodiment, the exodomain comprises an extracellular ligand binding domain of a receptor selected from the group consisting of: PD-1, LAG-3, TIM-3, CTLA-4, IL10R, TIGIT, TGFβRI, and TGFβRII.

In one embodiment, the donor repair template comprises a flip receptor comprising an exodomain that binds an immunosuppressive cytokine, a transmembrane domain, and one or more intracellular co-stimulatory signaling domains and/or primary signaling domains.

Illustrative examples of transmembrane domains suitable for use in particular embodiments of flip receptors contemplated in particular embodiments include, but are not limited to transmembrane domains of the following proteins: PD-1, LAG-3, TIM-3, CTLA-4, IL10R, TIGIT, TGFβRI and TGFβRII alpha or beta chain of the T-cell receptor, CDδ, CD3ε, CDγ, CD3ζ, CD4, CD5, CD8α, CD9, CD 16, CD22, CD27, CD28, CD33, CD37, CD45, CD64, CD80, CD86, CD 134, CD137, or CD154.

In various embodiments, the flip receptor comprises an endodomain that elicits an immunostimulatory signal. As used herein, the term "endodomain" refers to an immunostimulatory motif or domain, including but not limited to an immunoreceptor tyrosine activation motif (ITAM), a costimulatory signaling domain, a primary signaling domain, or another intracellular domain that is associated with eliciting immunostimulatory signals in T cells.

Illustrative examples of endodomains suitable for use in particular embodiments of flip receptors contemplated in particular embodiments include, but are not limited to domains comprising an ITAM motif.

Additional illustrative examples of endodomains suitable for use in particular embodiments of flip receptors contemplated in particular embodiments include, but are not limited to co-stimulatory signaling domains is isolated from: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, or ZAP70.

Additional illustrative examples of endodomains suitable for use in particular embodiments of flip receptors contemplated in particular embodiments include, but are not limited to: an endodomain isolated from an IL-2 receptor, IL-7 receptor, IL-12 receptor, IL-15 receptor, or IL-21 receptor.

Further illustrative examples of endodomains suitable for use in particular embodiments of flip receptors contemplated in particular embodiments include, but are not limited to primary signaling domains is isolated from: FcRγ, FcRβ, CD3γ, CD3δ, CD3ε, CD3ζ, CD22, CD79a, CD79b, and CD66d.

In particular embodiments, the flip receptor comprises an exodomain that comprises an extracellular domain from PD-1, LAG-3, TIM-3, CTLA-4, IL10R, TIGIT, TGFβRI or TGFβRII: an endodomain isolated from an IL-2 receptor, IL-7 receptor, IL-12 receptor, IL-15 receptor, or IL-21 receptor.

In particular embodiments, the flip receptor comprises an exodomain that comprises an extracellular domain from PD-1, LAG-3, TIM-3, CTLA-4, IL10R, TIGIT, TGFβRI or TGFβRII; a transmembrane domain from a CD3 polypeptide, CD4, CD8α, CD28, CD134, CD137, PD-1, LAG-3, TIM-3, CTLA-4, IL10R, TGFβRI and TGFβRII; and an endodomain from CD28, CD134, CD137, CD278, and/or CD3ζ.

In particular embodiments, the flip receptor comprises an exodomain that comprises an extracellular domain from PD-1, LAG-3, TIM-3, CTLA-4, IL10R, TIGIT, or TGFβRII; a transmembrane domain from a CD3 polypeptide, CD4, CD8α, CD28, CD134, or CD137; and an endodomain from CD28, CD134, CD137, CD278, and/or CD3ζ.

In particular embodiments, methods of generating modified immune effector cells comprises contacting the cells with a stimulatory agent and costimulatory agent, such as soluble anti-CD3 and anti-CD28 antibodies, or antibodies attached to a bead or other surface, modifying the immune effector cells to express an engineered antigen receptor and/or flip receptor, and/or gene editing the cells and culturing the cells in a medium with appropriate cytokines, such as IL-2, IL-7, and/or IL-15 and/or one or more agents that modulate a PI3K cell signaling pathway.

As used herein, the term "PI3K inhibitor" refers to a nucleic acid, peptide, compound, or small organic molecule that binds to and inhibits at least one activity of PI3K. The PI3K proteins can be divided into three classes, class 1 PI3Ks, class 2 PI3Ks, and class 3 PI3Ks. Class 1 PI3Ks exist as heterodimers consisting of one of four p110 catalytic subunits (p111α, p110β, p110δ, and p110γ) and one of two families of regulatory subunits. In particular embodiments, a PI3K inhibitor targets the class 1 PI3K inhibitors. In one embodiment, a PI3K inhibitor will display selectivity for one or more isoforms of the class 1 PI3K inhibitors (i.e., selectivity for p110α, p110β, p110δ, and p110γ or one or more of p110α, p110β, p110δ, and p110γ). In another aspect, a PI3K inhibitor will not display isoform selectivity and be considered a "pan-PI3K inhibitor." In one embodiment, a PI3K inhibitor will compete for binding with ATP to the PI3K catalytic domain.

Illustrative examples of PI3K inhibitors suitable for use particular embodiments include, but are not limited to, BKM120 (class 1 PI3K inhibitor, Novartis), XL147 (class 1 PI3K inhibitor, Exelixis), (pan-PI3K inhibitor, GlaxoSmithKline), and PX-866 (class 1 PI3K inhibitor; p110α, p110β, and p110γ isoforms, Oncothyreon).

Other illustrative examples of selective PI3K inhibitors include, but are not limited to BYL719, GSK2636771, TGX-221, AS25242, CAL-101, ZSTK474, and IPI-145.

Further illustrative examples of pan-PI3K inhibitors include, but are not limited to BEZ235, LY294002, GSK1059615, TG100713, and GDC-0941.

In a preferred embodiment, the PI3K inhibitor is ZSTK474.

H. Polypeptides

Various polypeptides are contemplated herein, including, but not limited to, viral polypeptides, non-viral polypeptides, therapeutic polypeptides, fusion polypeptides, antibodies and antigen binding fragments thereof, engineered antigen receptors, BiTEs, checkpoint inhibitors, cytokines, chemokines, cytotoxins, flip receptors, growth factors, proteases, and the like. In preferred embodiments, a polypeptide comprises an amino acid sequence set forth in any one or more of SEQ ID NOs: 1-38. "Polypeptide," "polypeptide fragment," "peptide" and "protein" are used interchangeably, unless specified to the contrary, and according to conventional meaning, i.e., as a sequence of amino acids. In one embodiment, a "polypeptide" includes fusion polypeptides and other variants. Polypeptides can be prepared using any of a variety of well-known recombinant and/or synthetic techniques. Polypeptides are not limited to a specific length, e.g., they may comprise a full-length protein sequence, a fragment of a full-length protein, or a fusion protein, and may include post-translational modifications of the polypeptide, for example, glycosylations, acetylations, phosphorylations and the like, as well as other modifications known in the art, both naturally occurring and non-naturally occurring.

An "isolated protein," "isolated peptide," or "isolated polypeptide" and the like, as used herein, refer to in vitro synthesis, isolation, and/or purification of a peptide or polypeptide molecule from a cellular environment, and from association with other components of the cell, i.e., it is not significantly associated with in vivo substances.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in particular embodiments, it may be desirable to improve the binding affinity and/or other biological properties of a polypeptide by introducing one or more substitutions, deletions, additions and/or insertions the polypeptide. In particular embodiments, polypeptides include polypeptides having at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% amino acid identity to any of the reference sequences contemplated herein, typically where the variant maintains at least one biological activity of the reference sequence.

Polypeptides include "polypeptide fragments." Polypeptide fragments refer to a polypeptide, which can be monomeric or multimeric that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long. Particularly useful polypeptide fragments include functional domains, including antigen-binding domains or fragments of antibodies The polypeptide may also be fused in-frame or conjugated to a linker or other sequence for ease of synthesis, purification or identification of the polypeptide (e.g., poly-His), or to enhance binding of the polypeptide to a solid support.

As noted above, polypeptides may be altered in various ways including amino acid modifications, substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., (*Molecular Biology of the Gene,* Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure* (Natl. Biomed. Res. Found., Washington, D.C.).

In certain embodiments, a polypeptide variant comprises one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides contemplated in particular embodiments and still obtain a functional molecule that encodes a variant or derivative polypeptide with desirable characteristics. When it is desired to alter the amino acid sequence of a polypeptide to create an equivalent, or even an improved, variant polypeptide, one skilled in the art, for example, can change one or more of the codons of the encoding DNA sequence, e.g., according to Table 1.

TABLE 1

Amino Acid Codons

| Amino Acids | One letter code | Three letter code | Codons | | | | | |
|---|---|---|---|---|---|---|---|---|
| Alanine | A | Ala | GCA | GCC | GCG | | GCU | |
| Cysteine | C | Cys | UGC | | | UGU | | |
| Aspartic acid | D | Asp | GAC | | | GAU | | |
| Glutamic acid | E | Glu | GAA | | | GAG | | |
| Phenylalanine | F | Phe | UUC | | | UUU | | |
| Glycine | G | Gly | GGA | GGC | GGG | | GGU | |
| Histidine | H | His | CAC | CAU | | | | |
| Isoleucine | I | Iso | AUA | AUC | | AUU | | |
| Lysine | K | Lys | AAA | AAG | | | | |
| Leucine | L | Leu | UUA | UUG | CUA | CUC | CUG | CUU |
| Methionine | M | Met | | | AUG | | | |
| Asparagine | N | Asn | AAC | AAU | | | | |
| Proline | P | Pro | CCA | CCC | CCG | | CCU | |
| Glutamine | Q | Gln | CAA | CAG | | | | |
| Arginine | R | Arg | AGA | AGG | CGA | CGC | CGG | CGU |
| Serine | S | Ser | AGC | AGU | UCA | UCC | UCG | UCU |
| Threonine | T | Thr | ACA | ACC | ACG | | ACU | |
| Valine | V | Val | GUA | GUC | GUG | | GUU | |
| Tryptophan | W | Trp | | | UGG | | | |
| Tyrosine | Y | Tyr | UAC | | | UAU | | |

Guidance in determining which amino acid residues can be substituted, inserted, or deleted without abolishing biological activity can be found using computer programs well known in the art, such as DNASTAR, DNA Strider, Geneious, Mac Vector, or Vector NTI software. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224).

As outlined above, amino acid substitutions may be based on the relative similarity of the amino acid side-chain substituents, for example, their hydrophobicity, hydrophilicity, charge, size, and the like.

Polypeptide variants further include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

In one embodiment, where expression of two or more polypeptides is desired, the polynucleotide sequences encoding them can be separated by an IRES sequence as discussed elsewhere herein. In another embodiment, two or more polypeptides can be expressed as a fusion protein that comprises one or more self-cleaving polypeptide sequences.

Polypeptides contemplated in particular embodiments include fusion polypeptides. In preferred embodiments, fusion polypeptides and polynucleotides encoding fusion polypeptides are provided, e.g., engineered antigen receptors, flip receptors, etc. Fusion polypeptides and proteins refer to a polypeptide having at least two, three, four, five, six, seven, eight, nine, or ten or more polypeptide segments. Fusion polypeptides are typically linked C-terminus to N-terminus, although they can also be linked C-terminus to C-terminus, N-terminus to N-terminus, or N-terminus to C-terminus. The polypeptides of the fusion protein can be in any order or a specified order. Fusion polypeptides or fusion proteins can also include conservatively modified variants, polymorphic variants, alleles, mutants, subsequences, and interspecies homologs, so long as the desired transcriptional activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as discussed elsewhere herein.

In one embodiment, a fusion partner comprises a sequence that assists in expressing the protein (an expression enhancer) at higher yields than the native recombinant protein. Other fusion partners may be selected so as to increase the solubility of the protein or to enable the protein to be targeted to desired intracellular compartments or to facilitate transport of the fusion protein through the cell membrane.

Fusion polypeptides may optionally comprises a linker that can be used to link the one or more polypeptides or domains within a polypeptide. A peptide linker sequence may be employed to separate any two or more polypeptide components by a distance sufficient to ensure that each polypeptide folds into its appropriate secondary and tertiary structures so as to allow the polypeptide domains to exert their desired functions. Such a peptide linker sequence is incorporated into the fusion polypeptide using standard techniques in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. Nos. 4,935,233 and 4,751,180. Linker sequences are not required when a particular fusion polypeptide segment contains non-essential N-terminal amino acid regions that can be used to separate the functional domains and prevent steric interference. Preferred linkers are typically flexible amino acid subsequences which are synthesized as part of a recombinant fusion protein. Linker polypeptides can be between 1 and 200 amino acids in length, between 1 and 100 amino acids in length, or between 1 and 50 amino acids in length, including all integer values in between.

Exemplary linkers include, but are not limited to the following amino acid sequences: glycine polymers $(G)_n$; glycine-serine polymers $(G_{1-5}S_{1-5})_n$, where n is an integer of at least one, two, three, four, or five; glycine-alanine polymers; alanine-serine polymers; GGG (SEQ ID NO: 3); DGGGS (SEQ ID NO: 4); TGEKP (SEQ ID NO: 5) (see e.g., Liu et al., PNAS 5525-5530 (1997)); GGRR (SEQ ID NO: 6) (Pomerantz et al. 1995, supra); $(GGGGS)_n$ wherein n=1, 2, 3, 4 or 5 (SEQ ID NO: 7) (Kim et al., PNAS 93, 1156-1160 (1996).); EGKSSGSGSESKVD (SEQ ID NO: 8) (Chaudhary et al., 1990, Proc. Natl. Acad. Sci. U.S.A. 87:1066-1070); KESGSVSSEQLAQFRSLD (SEQ ID NO 9:) (Bird et al., 1988, Science 242:423-426), GGRRGGGS (SEQ ID NO: 10); LRQRDGERP (SEQ ID NO: 11); LRQKDGGGSERP (SEQ ID NO: 12); LRQKD(GGGS)$_2$ ERP (SEQ ID NO: 13). Alternatively, flexible linkers can be rationally designed using a computer program capable of modeling both DNA-binding sites and the peptides themselves (Desjarlais & Berg, PNAS 90:2256-2260 (1993), PNAS 91:11099-11103 (1994) or by phage display methods.

Fusion polypeptides may further comprise a polypeptide cleavage signal between each of the polypeptide domains described herein. In addition, a polypeptide cleavage site can be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. Traffic, 5(8); 616-26).

Suitable protease cleavages sites and self-cleaving peptides are known to the skilled person (see, e.g., in Ryan et al., 1997. J. Gener. Virol. 78, 699-722; Scymczak et al. (2004) Nature Biotech. 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ(G/S) (SEQ ID NO: 14), for example, ENLYFQG (SEQ ID NO: 15) and ENLYFQS (SEQ ID NO: 16) wherein X represents any amino acid (cleavage by TEV occurs between Q and G or Q and S).

In a particular embodiment, self-cleaving peptides include those polypeptide sequences obtained from potyvirus and cardiovirus 2A peptides, FMDV (foot-and-mouth disease virus), equine rhinitis A virus, Thosea asigna virus and porcine teschovirus.

In certain embodiments, the self-cleaving polypeptide site comprises a 2A or 2A-like site, sequence or domain (Donnelly et al., 2001. J. Gen. Virol. 82:1027-1041). Exemplary 2A sites are shown in Table 2.

TABLE 2

| SEQ ID NO: 17 | GSGATNFSLLKQAGDVEENPGP |
|---|---|
| SEQ ID NO: 18 | ATNFSLLKQAGDVEENPGP |
| SEQ ID NO: 19 | LLKQAGDVEENPGP |
| SEQ ID NO: 20 | GSGEGRGSLLTCGDVEENPGP |
| SEQ ID NO: 21 | EGRGSLLTCGDVEENPGP |
| SEQ ID NO: 22 | LLTCGDVEENPGP |
| SEQ ID NO: 23 | GSGQCTNYALLKLAGDVESNPGP |
| SEQ ID NO: 24 | QCTNYALLKLAGDVESNPGP |
| SEQ ID NO: 25 | LLKLAGDVESNPGP |
| SEQ ID NO: 26 | GSGVKQTLNFDLLKLAGDVESNPGP |
| SEQ ID NO: 27 | VKQTLNFDLLKLAGDVESNPGP |
| SEQ ID NO: 28 | LLKLAGDVESNPGP |
| SEQ ID NO: 29 | LLNFDLLKLAGDVESNPGP |
| SEQ ID NO: 30 | TLNFDLLKLAGDVESNPGP |
| SEQ ID NO: 31 | LLKLAGDVESNPGP |
| SEQ ID NO: 32 | NFDLLKLAGDVESNPGP |
| SEQ ID NO: 33 | QLLNFDLLKLAGDVESNPGP |
| SEQ ID NO: 34 | APVKQTLNFDLLKLAGDVESNPGP |
| SEQ ID NO: 35 | VTELLYRMKRAETYCPRPLLAIHPTEARHKQKIVAPVKQT |
| SEQ ID NO: 36 | LNFDLLKLAGDVESNPGP |
| SEQ ID NO: 37 | LLAIHPTEARHKQKIVAPVKQTLNFDLLKLAGDVESNPGP |
| SEQ ID NO: 38 | EARHKQKIVAPVKQTLNFDLLKLAGDVESNPGP |

I. Polynucleotides

In particular embodiments, polynucleotides encoding polypeptides. As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), RNA, short interfering RNA (siRNA), siRNA target sites, short hairpin RNA (shRNA), shRNA target sites, microRNA (miRNA or miR), microRNA target sites, ribozymes, ribozyme target sites, genomic RNA (gRNA), plus strand RNA (RNA(+)), minus strand RNA (RNA(−)), tracrRNA, crRNA, single guide RNA (sgRNA), synthetic RNA, synthetic mRNA, genomic DNA (gDNA), PCR amplified DNA, complementary DNA (cDNA), synthetic DNA, or recombinant DNA. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc. In particular embodiments, polynucleotides or variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence.

In particular embodiments, polynucleotides may be codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, and/or (xi) isolated removal of spurious translation initiation sites.

As used herein the term "nucleotide" refers to a heterocyclic nitrogenous base in N-glycosidic linkage with a phosphorylated sugar. Nucleotides are understood to include natural bases, and a wide variety of art-recognized modified bases. Such bases are generally located at the 1' position of a nucleotide sugar moiety. Nucleotides generally comprise a base, sugar and a phosphate group. In ribonucleic acid (RNA), the sugar is a ribose, and in deoxyribonucleic acid (DNA) the sugar is a deoxyribose, i.e., a sugar lacking a hydroxyl group that is present in ribose. Exemplary natural nitrogenous bases include the purines, adenosine (A) and guanidine (G), and the pyrimidines, cytidine (C) and thymidine (T) (or in the context of RNA, uracil (U)). The C-1 atom of deoxyribose is bonded to N-1 of a pyrimidine or N-9 of a purine. Nucleotides are usually mono, di- or triphosphates. The nucleotides can be unmodified or modified at the sugar, phosphate and/or base moiety, (also referred to interchangeably as nucleotide analogs, nucleotide derivatives, modified nucleotides, non-natural nucleotides, and non-standard nucleotides; see for example, WO 92/07065 and WO 93/15187). Examples of modified nucleic acid bases are summarized by Limbach et al., (1994, *Nucleic Acids Res.* 22, 2183-2196).

A nucleotide may also be regarded as a phosphate ester of a nucleoside, with esterification occurring on the hydroxyl group attached to C-5 of the sugar. As used herein, the term "nucleoside" refers to a heterocyclic nitrogenous base in N-glycosidic linkage with a sugar. Nucleosides are recognized in the art to include natural bases, and also to include well known modified bases. Such bases are generally located at the 1' position of a nucleoside sugar moiety. Nucleosides generally comprise a base and sugar group. The nucleosides can be unmodified or modified at the sugar, and/or base moiety, (also referred to interchangeably as nucleoside analogs, nucleoside derivatives, modified nucleosides, non-natural nucleosides, or non-standard nucleosides). As also noted above, examples of modified nucleic acid bases are summarized by Limbach et al., (1994, *Nucleic Acids Res.* 22, 2183-2196).

Illustrative examples of polynucleotides include, but are not limited to polynucleotides encoding SEQ ID NOs: 1-38.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, substitution, or modification of at least one nucleotide. Accordingly, the terms "polynucleotide variant" and "variant" include polynucleotides in which one or more nucleotides have been added or deleted, or modified, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide.

In one embodiment, a polynucleotide comprises a nucleotide sequence that hybridizes to a target nucleic acid sequence under stringent conditions. To hybridize under "stringent conditions" describes hybridization protocols in which nucleotide sequences at least 60% identical to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in for example, DNASTAR, GCG, DNA Strider, Geneious, Mac Vector, or Vector NTI software) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., *Current Protocols in Molecular Biology*, John Wiley & Sons Inc., 1994-1998, Chapter 15.

An "isolated polynucleotide," as used herein, refers to a polynucleotide that has been purified from the sequences which flank it in a naturally-occurring state, e.g., a DNA fragment that has been removed from the sequences that are normally adjacent to the fragment. In particular embodiments, an "isolated polynucleotide" refers to a complementary DNA (cDNA), a recombinant polynucleotide, a synthetic polynucleotide, or other polynucleotide that does not exist in nature and that has been made by the hand of man.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5' to 3' strand is designated the "sense," "plus," or "coding" strand because its sequence is identical to the sequence of the pre-messenger (pre-mRNA) [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3' sequence written in the 3' to 5' orientation or a 3' to 5' sequence written in the 5' to 3' orientation.

The terms "complementary" and "complementarity" refer to polynucleotides (i.e., a sequence of nucleotides) related by the base-pairing rules. For example, the complementary strand of the DNA sequence 5' A G T C A T G 3' is 3'T C A G T A C 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acid bases are matched according to the base pairing rules. Or, there can be "complete" or "total" complementarity between the nucleic acids.

The term "nucleic acid cassette" or "expression cassette" as used herein refers to genetic sequences within the vector which can express an RNA, and subsequently a polypeptide. In one embodiment, the nucleic acid cassette contains a gene(s)-of-interest, e.g., a polynucleotide(s)-of-interest. In another embodiment, the nucleic acid cassette contains one or more expression control sequences, e.g., a promoter, enhancer, poly(A) sequence, and a gene(s)-of-interest, e.g., a polynucleotide(s)-of-interest. Vectors may comprise 1, 2, 3, 4, 5, 6, 7, 8, 9 or 10 or more nucleic acid cassettes. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, in some embodiments, the cassette has its 3' and 5' ends adapted for ready insertion into a vector and/or genome, e.g., it has restriction endonuclease sites at each end. In a preferred embodiment, the nucleic acid cassette contains the sequence of a therapeutic gene used to treat, prevent, or ameliorate a genetic disorder. The cassette can be removed and inserted into a plasmid or viral vector as a single unit.

Polynucleotides include polynucleotide(s)-of-interest. As used herein, the term "polynucleotide-of-interest" refers to a polynucleotide encoding a polypeptide, a therapeutic polypeptide or fusion polypeptide, as contemplated herein.

Moreover, it will be appreciated by those of ordinary skill in the art that, as a result of the degeneracy of the genetic code, there are many nucleotide sequences that may encode a polypeptide, or fragment of variant thereof, as contemplated herein. Some of these polynucleotides bear minimal homology to the nucleotide sequence of any native gene. Nonetheless, polynucleotides that vary due to differences in codon usage are specifically contemplated in particular embodiments, for example polynucleotides that are optimized for human and/or primate codon selection. In one embodiment, polynucleotides comprising particular allelic sequences are provided. Alleles are endogenous polynucleotide sequences that are altered as a result of one or more mutations, such as deletions, additions and/or substitutions of nucleotides.

In a certain embodiment, a polynucleotide is an siRNA, an miRNA, an shRNA, a ribozyme or another inhibitory RNA or an siRNA target site, an miRNA target site, an shRNA target site, a ribozyme target site, or other inhibitory RNA target site.

In a preferred embodiment, a miR target sequence is introduced into a polynucleotide encoding one or more viral genes essential for viral replication.

The polynucleotides contemplated in particular embodiments, regardless of the length of the coding sequence itself, may be combined with other DNA sequences, such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, post-transcription response elements, and polynucleotides encoding self-cleaving polypeptides, epitope tags, as disclosed elsewhere herein or as known in the art, such that their overall length may vary considerably. It is therefore contemplated in particular embodiments that a polynucleotide fragment of almost any length may be employed, with the total length preferably being limited by the ease of preparation and use in the intended recombinant DNA protocol.

Polynucleotides can be prepared, manipulated, expressed and/or delivered using any of a variety of well-established techniques known and available in the art. In order to express a desired polypeptide, a nucleotide sequence encoding the polypeptide, can be inserted into appropriate vector. A desired polypeptide can also be expressed by delivering an mRNA encoding the polypeptide into the cell.

Illustrative examples of vectors include, but are not limited to plasmid, autonomously replicating sequences, and transposable elements, e.g., Sleeping Beauty, PiggyBac.

Additional illustrative examples of vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses.

Illustrative examples of viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

Illustrative examples of expression vectors include, but are not limited to pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, coding sequences of polypeptides disclosed herein can be ligated into such expression vectors for the expression of the polypeptides in mammalian cells.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally.

"Expression control sequences," "control elements," or "regulatory sequences" present in an expression vector are those non-translated regions of the vector—origin of replication, selection cassettes, promoters, enhancers, translation initiation signals (Shine Dalgarno sequence or Kozak sequence) introns, post-transcriptional regulatory elements, a polyadenylation sequence, 5' and 3' untranslated regions—which interact with host cellular proteins to carry out transcription and translation. Such elements may vary in their strength and specificity. Depending on the vector system and host utilized, any number of suitable transcription and translation elements, including ubiquitous promoters and inducible promoters may be used.

In particular embodiments, a polynucleotide comprises a vector, including but not limited to expression vectors and viral vectors. A vector may comprise one or more exogenous, endogenous, or heterologous control sequences such as promoters and/or enhancers. An "endogenous control sequence" is one which is naturally linked with a given gene in the genome. An "exogenous control sequence" is one which is placed in juxtaposition to a gene by means of genetic manipulation (i.e., molecular biological techniques) such that transcription of that gene is directed by the linked enhancer/promoter. A "heterologous control sequence" is an exogenous sequence that is from a different species than the cell being genetically manipulated. A "synthetic" control sequence may comprise elements of one more endogenous and/or exogenous sequences, and/or sequences determined in vitro or in silico that provide optimal promoter and/or enhancer activity for the particular therapy.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, a short elongation factor 1-alpha (EF1a-short) promoter, a long elongation factor 1-alpha (EF1a-long) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., Nature Biotechnology 25, 1477-1482 (2007)), a Ubiquitin C promoter (UBC), a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted (MND) promoter (Challita et al., *J Virol.* 69(2):748-55 (1995)).

In a particular embodiment, it may be desirable to use a cell, cell type, cell lineage or tissue specific expression control sequence to achieve cell type specific, lineage specific, or tissue specific expression of a desired polynucleotide sequence (e.g., to express a particular nucleic acid encoding a polypeptide in only a subset of cell types, cell lineages, or tissues or during specific stages of development).

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, Gene, 323:67), the cumate inducible gene switch (WO 2002/088346), tetracycline-dependent regulatory systems, etc.

Conditional expression can also be achieved by using a site specific DNA recombinase. According to certain embodiments, polynucleotides comprises at least one (typically two) site(s) for recombination mediated by a site specific recombinase. As used herein, the terms "recombinase" or "site specific recombinase" include excusive or integrative proteins, enzymes, co-factors or associated proteins that are involved in recombination reactions involving one or more recombination sites (e.g., two, three, four, five, six, seven, eight, nine, ten or more.), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Illustrative examples of recombinases suitable for use in particular embodiments include, but are not limited to: Cre, Int, IHF, Xis, Flp, Fis, Hin, Gin, ΦC31, Cin, Tn3 resolvase, TndX, XerC, XerD, TnpX, Hjc, Gin, SpCCE1, and ParA.

In particular embodiments, polynucleotides contemplated herein, include one or more polynucleotides-of-interest that encode one or more polypeptides. In particular embodiments, to achieve efficient translation of each of the plurality of polypeptides, the polynucleotide sequences can be separated by one or more IRES sequences or polynucleotide sequences encoding self-cleaving polypeptides.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. *RNA* 1(10):985-1000. Examples of IRES generally employed by those of skill in the art include those described in U.S. Pat. No. 6,692,736. Further examples of "IRES" known in the art include, but are not limited to IRES obtainable from picornavirus (Jackson et al., 1990) and IRES obtainable from viral or cellular mRNA sources, such as for example, immunoglobulin heavy-chain binding protein (BiP), the vascular endothelial growth factor (VEGF) (Huez et al. 1998. *Mol. Cell. Biol.* 18(11):6178-6190), the fibroblast growth factor 2 (FGF-2), and insulin-like growth factor (IGFII), the translational initiation factor eIF4G and yeast transcription factors TFIID and HAP4, the encephelomycarditis virus (EMCV) which is commercially available from Novagen (Duke et al., 1992. J. Virol 66(3): 1602-9) and the VEGF IRES (Huez et al., 1998. Mol Cell Biol 18(11):6178-90). IRES have also been reported in viral genomes of Picornaviridae, Dicistroviridae and Flaviviridae species and in HCV, Friend murine leukemia virus (FrMLV) and Moloney murine leukemia virus (MoMLV).

In one embodiment, the IRES used in polynucleotides contemplated herein is an EMCV IRES.

In particular embodiments, the polynucleotides comprise polynucleotides that have a consensus Kozak sequence and that encode a desired polypeptide. As used herein, the term "Kozak sequence" refers to a short nucleotide sequence that greatly facilitates the initial binding of mRNA to the small subunit of the ribosome and increases translation. The consensus Kozak sequence is (GCC)RCCATGG, where R is a purine (A or G) (Kozak, 1986. *Cell.* 44(2):283-92, and Kozak, 1987. *Nucleic Acids Res.* 15(20):8125-48).

Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is an ideal polyA sequence (e.g., AATAAA, ATTAAA, AGTAAA). In particular embodiments, the poly(A) sequence is an SV40 polyA sequence, a bovine growth hormone polyA sequence (BGHpA), a rabbit β-globin polyA sequence (rβgpA), variants thereof, or another suitable heterologous or endogenous polyA sequence known in the art.

In some embodiments, a polynucleotide or cell harboring the polynucleotide utilizes a suicide gene, including an inducible suicide gene to reduce the risk of direct toxicity and/or uncontrolled proliferation. In specific embodiments, the suicide gene is not immunogenic to the host harboring the polynucleotide or cell. A certain example of a suicide gene that may be used is caspase-9 or caspase-8 or cytosine deaminase. Caspase-9 can be activated using a specific chemical inducer of dimerization (CID).

In certain embodiments, polynucleotides comprise gene segments that cause the genetically modified cells contemplated herein to be susceptible to negative selection in vivo. "Negative selection" refers to an infused cell that can be eliminated as a result of a change in the in vivo condition of the individual. The negative selectable phenotype may result from the insertion of a gene that confers sensitivity to an administered agent, for example, a compound. Negative selection genes are known in the art, and include, but are not limited to: the Herpes simplex virus type I thymidine kinase (HSV-I TK) gene which confers ganciclovir sensitivity; the cellular hypoxanthine phosphribosyltransferase (HPRT) gene, the cellular adenine phosphoribosyltransferase (APRT) gene, and bacterial cytosine deaminase.

In some embodiments, genetically modified cells comprise a polynucleotide further comprising a positive marker that enables the selection of cells of the negative selectable phenotype in vitro. The positive selectable marker may be a gene, which upon being introduced into the host cell, expresses a dominant phenotype permitting positive selection of cells carrying the gene. Genes of this type are known in the art, and include, but are not limited to hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

In one embodiment, the positive selectable marker and the negative selectable element are linked such that loss of the negative selectable element necessarily also is accompanied by loss of the positive selectable marker. In a particular embodiment, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See also the publications of PCT US91/08442 and PCT/US94/05601, by S. D. Lupton, describing the use of bifunctional selectable fusion genes derived from fusing a dominant positive selectable markers with negative selectable markers.

Preferred positive selectable markers are derived from genes selected from the group consisting of hph, neo, and gpt, and preferred negative selectable markers are derived from genes selected from the group consisting of cytosine deaminase, HSV-I TK, VZV TK, HPRT, APRT and gpt. Exemplary bifunctional selectable fusion genes contemplated in particular embodiments include, but are not limited to genes wherein the positive selectable marker is derived from hph or neo, and the negative selectable marker is derived from cytosine deaminase or a TK gene or selectable marker.

In particular embodiments, polynucleotides may be introduced into cells by both non-viral and viral methods.

Illustrative examples of non-viral vectors include, but are not limited to plasmids (e.g., DNA plasmids or RNA plasmids), transposons, cosmids, and bacterial artificial chromosomes.

Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid:nucleic acid conjugates, naked DNA, artificial virions, DEAE-dextran-mediated transfer, gene gun, and heat-shock.

Illustrative examples of polynucleotide delivery systems suitable for use in particular embodiments contemplated in particular embodiments include, but are not limited to those provided by Amaxa Biosystems, Maxcyte, Inc., BTX Molecular Delivery Systems, and Copernicus Therapeutics Inc. Lipofection reagents are sold commercially (e.g., Transfectam™ and Lipofectin™). Cationic and neutral lipids that are suitable for efficient receptor-recognition lipofection of polynucleotides have been described in the literature. See e.g., Liu et al. (2003) *Gene Therapy.* 10:180-187; and Balazs et al. (2011) *Journal of Drug Delivery.* 2011:1-12. Antibody-targeted, bacterially derived, non-living nanocell-based delivery is also contemplated in particular embodiments.

Viral vectors comprising polynucleotides contemplated in particular embodiments can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., mobilized peripheral blood, lymphocytes, bone marrow aspirates, tissue biopsy, etc.) or universal donor hematopoietic stem cells, followed by reimplantation of the cells into a patient.

Illustrative examples of viral vector systems suitable for use in particular embodiments contemplated herein include, but are not limited to adeno-associated virus (AAV), retrovirus, lentivirus, herpes simplex virus, adenovirus, and vaccinia virus vectors.

J. Compositions and Formulations

The compositions contemplated herein may comprise one or more viruses, polypeptides, polynucleotides, vectors comprising same, modified immune effector cells, etc. Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

In particular embodiments, compositions comprise an amount of oncolytic virus. In other particular embodiments, compositions comprise an amount of modified immune effector cells As used herein, the term "amount" refers to "an amount effective" or "an effective amount" of oncolytic virus or therapeutic cells to achieve a beneficial or desired prophylactic or therapeutic result, including clinical results.

A "prophylactically effective amount" refers to an amount of oncolytic virus or therapeutic cells effective to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of oncolytic virus or therapeutic cells may vary according to factors such as the disease state, age, sex, and weight of the individual, and the ability of the composition to elicit a desired response in the individual. A therapeutically effective amount is also one in which any toxic or detrimental effects of oncolytic virus or therapeutic cells are outweighed by the therapeutically beneficial effects. The term "therapeutically effective amount" includes an amount that is effective to "treat" a subject (e.g., a patient). When a therapeutic amount is indicated, the precise amount of the compositions to be administered can be determined by a physician with consideration of individual differences in age, weight, tumor size, extent of infection or metastasis, and condition of the patient (subject).

Generally, oncolytic viral vectors contemplated herein, e.g., oncolytic HSV-1, are most useful when enough of the virus can be delivered to a target cell population to ensure that the target cells are confronted with a suitable number of viruses. In particular embodiments, a viral stock is provided, preferably a homogeneous stock, comprising oncolytic viral vectors contemplated herein. The preparation and analysis of oncolytic virus stocks is understood in the art. For example, an oncolytic virus stock can be manufactured in roller bottles containing cells transduced with the vector. The oncolytic virus stock can then be purified on a continuous nycodenze gradient, and aliquoted and stored until needed. Viral stocks vary considerably in titer, depending largely on viral genotype and the protocol and cell lines used to prepare them. In particular embodiments, a oncolytic virus stock preferably has a viral titer of at least about $10^5$ plaque-forming units (pfu), at least about $10^6$ pfu or even more preferably at least about $10^7$ pfu. In still more preferred embodiments, the titer can be at least about $10^8$ pfu, or at least about $10^9$ pfu, and high titer stocks of at least about $10^{10}$ pfu or at least about $10^{11}$ pfu are most preferred. Such titers can be established using cells that express a receptor to which the vector is targeted, for example.

It can generally be stated that a pharmaceutical composition comprising the immune effector described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some embodiments, particularly since all the infused cells will be redirected to a particular target antigen, lower numbers of cells, in the range of $10^6$/kilogram ($10^6$-$10^{11}$ per patient) may be administered. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-γ, IL-2, IL-12, TNF-alpha, IL-18, and TNF-beta, GM-CSF, IL-4, IL-13, Flt3-L, RANTES, MIP1α, etc.) as described herein to enhance induction of the immune response.

In particular embodiments, pharmaceutical compositions comprise an amount of oncolytic virus, in combination with one or more pharmaceutically or physiologically acceptable carriers, diluents or excipients.

In particular embodiments, pharmaceutical compositions comprise an amount of modified immune effector cells, in combination with one or more pharmaceutically or physiologically acceptable carriers, diluents or excipients.

Pharmaceutical compositions comprising an oncolytic virus or an immune effector cell population, such as modified T cells or NK cells may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In particular embodiments, compositions are preferably formulated for intratumorial or parenteral administration, e.g., intravascular (intravenous or intraarterial) administration.

The liquid pharmaceutical compositions, whether they be solutions, suspensions or other like form, may include one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In one embodiment, an oncoytic virus composition or an immune effector cell composition contemplated herein are formulated in a pharmaceutically acceptable cell culture medium. Such compositions are suitable for administration to human subjects. In particular embodiments, the pharmaceutically acceptable cell culture medium is a serum free medium.

In a particular embodiment, compositions comprise an effective amount of oncolytic virus or immune effector cells, alone or in combination with one or more therapeutic agents. Thus, the compositions may be administered alone or in combination with other known cancer treatments, such as radiation therapy, chemotherapy, transplantation, immunotherapy, hormone therapy, photodynamic therapy, etc. The compositions may also be administered in combination with antibiotics. Such therapeutic agents may be accepted in the art as a standard treatment for a particular disease state as described herein, such as a particular cancer. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

Illustrative examples of therapeutic antibodies suitable for combination treatment with the compositions contemplated herein, include but are not limited to, atezolizumab, avelumab, bavituximab, bevacizumab (avastin), bivatuzumab, blinatumomab, conatumumab, daratumumab, duligotumab, dacetuzumab, dalotuzumab, durvalumab, elotuzumab (Hu-Luc63), gemtuzumab, ibritumomab, indatuximab, inotuzumab, ipilimumab, lorvotuzumab, lucatumumab, milatuzumab, moxetumomab, nivolumab, ocaratuzumab, ofatumumab, pembrolizumab, rituximab, siltuximab, teprotumumab, and ublituximab.

K. Therapeutic Methods

The combination treatment of a subject in need thereof with the oncolytic viruses and modified immune effector cells contemplated herein provide improved methods of adoptive immunotherapy for use in the prevention, treatment, and amelioration cancers, or for preventing, treating, or ameliorating at least one symptom associated with a cancer.

In various embodiments, a subject in need thereof is administered an oncolytic virus contemplated herein, to ectopically express one or more target antigens on a target cell. Without wishing to be bound by any particular theory, it is contemplated that some of the target cells infected with the oncolytic virus will undergo lysis and the one or more target antigens will bind to nearby cells and thereby target them for destruction by immune effector cells that recognize the one or more target antigens. It is further contemplated that some of the target cells infected with the oncolytic may not undergo lysis prior to expressing the one or more target antigens, and thus, these target cells expressing the one or more target antigens will themselves be targeted for destruction by immune effector cells that recognize the one or more target antigens, and a bystander effect may lead to the death of nearby target cells. It is further contemplated that some of the target cells infected with the oncolytic virus may not undergo lysis, but nevertheless, may ectopically express the one or more target antigens and will themselves be targeted for destruction by immune effector cells that recognize the one or more target antigens, and a bystander effect may lead to the death of nearby target cells. Oncolytic viruses that also encode one or more therapeutic proteins, pseudotyped capsids, and that further comprise one or more tumor suppressor miR target sequences in genes essential to viral replication will enhance the efficacy and safety of the treatment methods contemplated herein.

In particular embodiments, a subject in need thereof, is administered an effective amount of an oncolytic virus that encodes one or more target antigens not expressed, or expressed at subtherapeutic levels, on a target cell and one or more tumor suppressor miR target sequences. After about one week, after about two weeks, after about three weeks, or after about four weeks, peripheral blood mononuclear cells (PBMCs) are harvested from the subject and immune effector cells are isolated from the PBMCs using leukapheresis. Without wishing to be bound by any particular theory, it is contemplated that the immune effector cells isolated from the subject comprise one or more of oncolytic virus specific T cells, target antigen specific T cells, non-specific T cells, NK cells, and γδ T cells. After the immune effector cells are isolated, vectors or mRNAs encoding one ore more engineered antigen receptors that recognize and bind the one or more target antigens are introduced into the immune effector cells. After the engineered immune effector cells are introduced into the immune effector cells, the cells are cultured for a duration sufficient to expand the cells. Once the modified immune effector cells are sufficiently expanded, a therapeutic dose of the cells is administered to the subject.

After the initial round of treatment, the cycle of virus administration or immune effector cell administration or both may be repeated one, two, three, four, five, or more times, until the tumor is eradicated or until the desired therapeutic effect is observed. In particular embodiments, the same viruses and immune effector cells may be readministered to the subject. In particular embodiments, an oncolytic virus encoding target antigens that are different from the target antigens in the first oncolytic virus is administered in a second or subsequent round of treatment. In this case, immune effector cells recognizing the new target antigen would be generated and administered to the subject in the second or subsequent rounds of treatment where the oncolytic virus used encodes the new antigen.

This cycle may be repeated as many times as necessary to eradicate the target cells, e.g., cancer cells, in the subject.

In a particular embodiment, an effective amount of an oncolytic virus contemplated herein encoding a target antigen that is not normally expressed on a cancer cell and one or more tumor suppressor miR target sequences in one or more genes essential for viral replication is administered to a subject that has cancer.

The cancer may be a solid cancer or a liquid cancer.

In one embodiment, the cancer is a solid cancer.

In particular embodiments, the type of solid cancer or tumor suitable for treatment using the methods contemplated in particular embodiments includes, but is not limited to: adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain/CNS cancer, breast cancer, bronchial tumors, cardiac tumors, cervical cancer, cholangiocarcinoma, chondrosarcoma, chordoma, colon cancer, colorectal cancer, craniopharyngioma, ductal carcinoma in situ (DCIS) endometrial cancer, ependymoma, esophageal cancer, esthesioneuroblastoma, Ewing's sarcoma, extracranial germ cell tumor, extragonadal germ cell tumor, eye cancer, fallopian tube cancer, fibrous histiosarcoma, fibrosarcoma, gallbladder cancer, gastric cancer, gastrointestinal carcinoid tumors, gastrointestinal stromal tumor (GIST), germ cell tumors, glioma, glioblastoma, head and neck cancer, hemangioblastoma, hepatocellular cancer, hypopharyngeal cancer, intraocular melanoma, kaposi sarcoma, kidney cancer, laryngeal cancer, leiomyosarcoma, lip cancer, liposarcoma, liver cancer, lung cancer, non-small cell lung cancer, lung carcinoid tumor, malignant mesothelioma, medullary carcinoma, medulloblastoma, menangioma, melanoma, Merkel cell carcinoma, midline tract carcinoma, mouth cancer, myxosarcoma, myelodysplastic syndrome, myeloproliferative neoplasms, nasal cavity and paranasal sinus cancer, nasopharyngeal cancer, neuroblastoma, oligodendroglioma, oral cancer, oral cavity cancer, oropharyngeal cancer, osteosarcoma, ovarian cancer, pancreatic cancer, pancreatic islet cell tumors, papillary carcinoma, paraganglioma, parathyroid cancer, penile cancer, pharyngeal cancer, pheochromocytoma, pinealoma, pituitary tumor, pleuropulmonary blastoma, primary peritoneal cancer, prostate cancer, rectal cancer, retinoblastoma, renal cell carcinoma, renal pelvis and ureter cancer, rhabdomyosarcoma, salivary gland cancer, sebaceous gland carcinoma, skin cancer, soft tissue sarcoma, squamous cell carcinoma, small cell lung cancer, small intestine cancer, stomach cancer, sweat gland carcinoma, synovioma, testicular cancer, throat cancer, thymus cancer, thyroid cancer, urethral cancer, uterine cancer, uterine sarcoma, vaginal cancer, vascular cancer, vulvar cancer, and Wilms Tumor.

In particular embodiments, the solid cancer is selected from the group consisting of: liver cancer, pancreatic cancer, lung cancer, breast cancer, bladder cancer, brain cancer, bone cancer, thyroid cancer, kidney cancer, and skin cancer.

In particular embodiments, the solid cancer is selected from the group consisting of: bladder cancer, breast cancer, colon cancer, glioblastoma, head and neck cancer, lung cancer, pancreatic cell, or a schwannoma.

In one embodiment, the cancer is a liquid cancer or hematological cancer.

In particular embodiments, the liquid or hematological cancer is selected from the group consisting of: leukemias, lymphomas, and multiple myeloma.

In particular embodiments, the type of liquid or hematological cancer suitable for treatment using the methods contemplated in particular embodiments leukemias, lymphomas, and multiple myelomas: acute lymphocytic leukemia (ALL), acute myeloid leukemia (AML), myeloblastic, promyelocytic, myelomonocytic, monocytic, erythroleukemia, hairy cell leukemia (HCL), chronic lymphocytic leukemia (CLL), and chronic myeloid leukemia (CML), chronic myelomonocytic leukemia (CMML) and polycythemia vera, Hodgkin lymphoma, nodular lymphocyte-predominant Hodgkin lymphoma, Burkitt lymphoma, small lymphocytic lymphoma (SLL), diffuse large B-cell lymphoma, follicular lymphoma, immunoblastic large cell lymphoma, precursor B-lymphoblastic lymphoma, mantle cell lymphoma, marginal zone lymphoma, mycosis fungoides, anaplastic large cell lymphoma, Sézary syndrome, precursor T-lymphoblastic lymphoma, multiple myeloma, overt multiple myeloma, smoldering multiple myeloma, plasma cell leukemia, non-secretory myeloma, IgD myeloma, osteosclerotic myeloma, solitary plasmacytoma of bone, and extramedullary plasmacytoma.

In a preferred embodiment, the oncolytic virus is an oncolytic HSV-1, and the modified immune effector cells are CAR T cells.

The quantity and frequency of administration of oncolytic virus and of immune effector cells will be determined by such factors as the condition of the patient, and the type and severity of the patient's disease, although appropriate dosages may be determined by clinical trials.

In one embodiment, the amount of immune effector cells, e.g., T cells, in the composition administered to a subject is at least $0.1 \times 10^5$ cells, at least $0.5 \times 10^5$ cells, at least $1 \times 10^5$ cells, at least $5 \times 10^5$ cells, at least $1 \times 10^6$ cells, at least $0.5 \times 10^7$ cells, at least $1 \times 10^7$ cells, at least $0.5 \times 10^8$ cells, at least $1 \times 10^8$ cells, at least $0.5 \times 10^9$ cells, at least $1 \times 10^9$ cells, at least $2 \times 10^9$ cells, at least $3 \times 10^9$ cells, at least $4 \times 10^9$ cells, at least $5 \times 10^9$ cells, or at least $1 \times 10^{10}$ cells.

In particular embodiments, about $1 \times 10^7$ T cells to about $1 \times 10^9$ T cells, about $2 \times 10^7$ T cells to about $0.9 \times 10^9$ T cells, about $3 \times 10^7$ T cells to about $0.8 \times 10^9$ T cells, about $4 \times 10^7$ T cells to about $0.7 \times 10^9$ T cells, about $5 \times 10^7$ T cells to about $0.6 \times 10^9$ T cells, or about $5 \times 10^7$ T cells to about $0.5 \times 10^9$ T cells are administered to a subject.

In one embodiment, the amount of immune effector cells, e.g., T cells, in the composition administered to a subject is at least $0.1 \times 10^4$ cells/kg of bodyweight, at least $0.5 \times 10^4$ cells/kg of bodyweight, at least $1 \times 10^4$ cells/kg of bodyweight, at least $5 \times 10^4$ cells/kg of bodyweight, at least $1 \times 10^5$ cells/kg of bodyweight, at least $0.5 \times 10^6$ cells/kg of bodyweight, at least $1 \times 10^6$ cells/kg of bodyweight, at least $0.5 \times 10^7$ cells/kg of bodyweight, at least $1 \times 10^7$ cells/kg of bodyweight, at least $0.5 \times 10^8$ cells/kg of bodyweight, at least $1 \times 10^8$ cells/kg of bodyweight, at least $2 \times 10^8$ cells/kg of bodyweight, at least $3 \times 10^8$ cells/kg of bodyweight, at least $4 \times 10^8$ cells/kg of bodyweight, at least $5 \times 10^8$ cells/kg of bodyweight, or at least $1 \times 10^9$ cells/kg of bodyweight.

In particular embodiments, about $1 \times 10^6$ T cells/kg of bodyweight to about $1 \times 10^8$ T cells/kg of bodyweight, about $2 \times 10^6$ T cells/kg of bodyweight to about $0.9 \times 10^8$ T cells/kg of bodyweight, about $3 \times 10^6$ T cells/kg of bodyweight to about $0.8 \times 10^8$ T cells/kg of bodyweight, about $4 \times 10^6$ T cells/kg of bodyweight to about $0.7 \times 10^8$ T cells/kg of bodyweight, about $5 \times 10^6$ T cells/kg of bodyweight to about $0.6 \times 10^8$ T cells/kg of bodyweight, or about $5 \times 10^6$ T cells/kg of bodyweight to about $0.5 \times 10^8$ T cells/kg of bodyweight are administered to a subject.

One of ordinary skill in the art would recognize that multiple administrations of the compositions contemplated in particular embodiments or multiple cycles of treatment may be required to effect the desired therapy. For example a composition may be administered, or a treatment cycle may be repeated, 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

The administration of the compositions contemplated in particular embodiments may be carried out in any convenient manner, including by aerosol inhalation, injection, ingestion, transfusion, implantation or transplantation. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection. In a preferred embodiment, oncolytic virus compositions are administered intratumorially or intravenously, and immune effector cells are administered intravenously.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Treatment

A patient having a solid cancer will receive an intratumoral injection of an effective amount of an oncolytic HSV-1 that comprises one of more polynucleotides encoding CD19 or BCMA, and MMP-9, and that further comprises one or more miR target sequences recognized and/or bound by a miR selected from the group consisting of hsa-miR-1-3p, hsa-miR-124-3p, hsa-miR-143-3p, hsa-miR-145-5p, hsa-miR-451a, and hsa-miR-559 inserted into ICP4 and ICP27.

After a duration of about 1 to 4 weeks, immune effector cells will be harvested from the subject and isolated by leukapheresis. The isolated immune effector cells will be transduced with a retrovirus or lentivirus encoding an anti-CD19 CAR or anti-BCMA CAR. The transduced cells will be cultured and administered to the subject.

The subject will be monitored for treatment safety and efficacy.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

SEQUENCE LISTING

| SEQ ID NO | NAME | SEQUENCE |
| --- | --- | --- |
| 1 | Anti-BCMA CAR | MALPVTALLLPLALLLHAARPDIVLTQSPPSLAMSLGKRATISCRASESVTILGSHLIHWYQQKPG QPPTLLIQLASNVQTGVPARFSGSGSRTDFTLTIDPVEEDDVAVYYCLQSRTIPRTFGGGTKLEIK GSTSGSGKPGSGEGSTKGQIQLVQSGPELKKPGETVKISCKASGYTFTDYSINWVKRAPGKGLK WMGWINTETREPAYAYDFRGRFAFSLETSASTAYLQINNLKYEDTATYFCALDYSYAMDYWG QGTSVTVSSAAATTTPAPRPPTPAPTIASQPLSLRPEACRPAAGGAVHTRGLDFACDIYIWAPLA GTCGVLLLSLVITLYCKRGRKKLLYIFKQPFMRPVQTTQEEDGCSCRFPEEEEGGCELRVKFSRSA DAPAYQQGQNQLYNELNLGRREEYDVLDKRRGRDPEMGGKPRRKNPQEGLYNELQKDKMA EAYSEIGMKGERRRGKGHDGLYQGLSTATKDTYDALHMQALPPR |
| 2 | Anti-CD19 CAR | MALPVTALLLPLALLLHAARPDIQMTQTTSSLSASLGDRVTISCRASQDISKYLNWYQQKPDGT VKLLIYHTSRLHSGVPSRFSGSGSGTDYSLTISNLEQEDIATYFCQQGNTLPYTFGGGTKLEITGG GGSGGGGSGGGGSEVKLQESGPGLVAPSQSLSVTCTVSGVSLPDYGVSWIRQPPRKGLEWLG VIWGSETTYYNSALKSRLTIIKDNSKSQVFLKMNSLQTDDTAIYYCAKHYYYGGSYAMDYWGQ GTSVTVSSTTTPAPRPPTPAPTIASQPLSLRPEACRPAAGGAVHTRGLDFACDIYIWAPLAGTCG VLLLSLVITLYCKRGRKKLLYIFKQPFMRPVQTTQEEDGCSCRFPEEEEGGCELRVKFSRSADAPA YQQGQNQLYNELNLGRREEYDVLDKRRGRDPEMGGKPRRKNPQEGLYNELQKDKMAEAYSE IGMKGERRRGKGHDGLYQGLSTATKDTYDALHMQALPPR |

The invention claimed is:

1. A recombinant oncolytic herpes simplex virus (HSV) comprising: (i) a polynucleotide encoding a target antigen; (ii) one or more tumor suppressor miR target sequences inserted into one or more essential viral genes required for viral replication, and (iii) a polynucleotide encoding a non-HSV polypeptide inserted into the gD gene or the gC gene.

2. The recombinant oncolytic herpes simplex virus of claim 1, wherein the target antigen is selected from the group consisting of: tumor associated antigens (TAA), tumor specific antigens (TSA), NKG2D ligands, γδ T cell receptor (TCR) ligands, and αβ TCR ligands, or wherein the target antigen is selected from the group consisting of: alpha folate receptor (FRα), αvβ6 integrin, B cell maturation antigen (BCMA), B7-H3 (CD276), B7-H6, carbonic anhydrase IX (CAIX), CD16, CD19, CD20, CD22, CD30, CD33, CD37, CD38, CD44, CD44v6, CD44v7/8, CD70, CD79a, CD79b, CD123, CD133, CD138, CD171, carcinoembryonic antigen (CEA), C-type lectin-like molecule-1 (CLL-1), CD2 subset 1 (CS-1), chondroitin sulfate proteoglycan 4 (CSPG4), cutaneous T cell lymphoma-associated antigen 1 (CTAGE1), epidermal growth factor receptor (EGFR), epidermal growth factor receptor variant III (EGFRvIII), epithelial glycoprotein 2 (EGP2), epithelial glycoprotein 40 (EGP40), epithelial cell adhesion molecule (EPCAM), ephrin type-A receptor 2 (EPHA2), fibroblast activation protein (FAP), Fc Receptor Like 5 (FCRL5), fetal acetylcholinesterase receptor (AchR), ganglioside G2 (GD2), ganglioside G3 (GD3), Glypican-3 (GPC3), EGFR family including ErbB2 (HER2), IL-11R☐, IL-13R☐2, Kappa, cancer/testis antigen 2 (LAGE-1A), Lambda, Lewis-Y (LeY), L1 cell adhesion molecule (L1-CAM), melanoma antigen gene (MAGE)-A1, MAGE-A3, MAGE-A4, MAGE-A6, MAGEA10, melanoma antigen recognized by T cells 1 (MelanA or MART1), Mesothelin (MSLN), MUC1, MUC16, MHC class I chain related proteins A (MICA), MHC class I chain related proteins B (MICB), neural cell adhesion molecule (NCAM), cancer/testis antigen 1 (NY-ESO-1), polysialic acid; placenta-specific 1 (PLAC1), preferentially expressed antigen in melanoma (PRAME), prostate stem cell antigen (PSCA), prostate-specific membrane antigen (PSMA), receptor tyrosine kinase-like orphan receptor 1 (ROR1), synovial sarcoma, X breakpoint 2 (SSX2), Survivin, tumor associated glycoprotein 72 (TAG72), tumor endothelial marker 1 (TEM1/CD248), tumor endothelial marker 7-related (TEM7R), trophoblast glycoprotein (TPBG), UL16-binding protein (ULBP) 1, ULBP2, ULBP3, ULBP4, ULBP5, ULBP6, vascular endothelial growth factor receptor 2 (VEGFR2), and Wilms tumor 1 (WT-1).

3. The recombinant oncolytic herpes simplex virus of claim 1, wherein the target antigen is BCMA or CD19.

4. The recombinant oncolytic herpes simplex virus of claim 1, further comprising one or more polynucleotides encoding one or more therapeutic polypeptides selected from the group consisting of: a bispecific T cell engager (BiTE), a checkpoint inhibitor, a cytokine, a protease, and an extracellular matrix remodeling enzyme.

5. The recombinant oncolytic herpes simplex virus of claim 1, further comprising a modification of one or more non-essential viral genes.

6. The recombinant oncolytic HSV of claim 1, wherein the one or more viral genes are selected from the group consisting of: the joint region, one or both copies of ICP-34.5, UL39 (ICP6), and US12 (ICP47, α47).

7. The recombinant oncolytic HSV of claim 1, wherein the non-HSV polypeptide is a ligand selected from the group consisting of: an antibody or antigen binding fragment thereof, a hormone, or a growth factor, or a ligand that specifically or selectively binds a protein on the surface of the target cell.

8. The recombinant oncolytic HSV of claim 1, wherein the non-HSV polypeptide binds:
   a) a growth factor receptor expressed on a target cell;
   b) an epidermal growth factor receptor (EGFR) or splice variant thereof, expressed on a target cell;
   c) a checkpoint protein expressed on a target cell; and/or
   d) a checkpoint protein selected from the group consisting of: PD-L1, PD-L2, and PD-1.

9. The recombinant oncolytic virus of claim 4, wherein the extracellular remodeling enzyme is MMP-9.

10. A method of treating a subject in need thereof comprising:
    a) administering to the subject an oncolytic herpes simplex virus according to claim 1;
    b) isolating immune effector cells from the subject;
    c) transducing the immune effector cells with vector encoding an engineered antigen receptor; and
    d) administering the transduced immune effector cells to the subject;
    wherein the transduced immune effectors cells bind the target antigen expressed on the target cell and induce cytolysis of the target cell.

11. A method of treating a subject that has cancer comprising:
    a) intra-tumorally administering to a solid cancer in the subject, an effective amount of a pseudotyped oncolytic HSV-1 comprising: a polynucleotide encoding a target antigen selected from the group consisting of CD19 and BCMA; a polynucleotide encoding human MMP-9 inserted into a non-essential viral gene and/or deleted joint region; and one or more tumor suppressor miR target sequences recognized and/or bound by a miR selected from the group consisting of hsa-miR-1-3p, hsa-miR-124-3p, hsa-miR-143-3p, hsa-miR-145-5p, hsa-miR-451a, and hsa-miR-559 inserted into one or more essential viral genes required for viral replication selected from the group consisting of ICP4 and ICP27;
    b) isolating immune effector cells from the subject about 1 week to about 4 weeks after administering the oncolytic HSV-1;
    c) transducing the immune effector cells with retroviral or lentiviral vector encoding an anti-CD19 CAR or anti-BCMA CAR; and
    d) administering the transduced immune effector cells to the subject; and optionally repeating steps a) through d).

* * * * *

SEQUENCE LISTING

```
Sequence total quantity: 38
SEQ ID NO: 1           moltype = AA  length = 493
FEATURE                Location/Qualifiers
REGION                 1..493
                       note = Anti-BCMA CAR
source                 1..493
                       mol_type = protein
                       organism = synthetic construct
SEQUENCE: 1
MALPVTALLL PLALLLHAAR PDIVLTQSPP SLAMSLGKRA TISCRASESV TILGSHLIHW    60
YQQKPGQPPT LLIQLASNVQ TGVPARFSGS GSRTDFTLTI DPVEEDDVAV YYCLQSRTIP   120
RTFGGGTKLE IKGSTSGSGK PGSGEGSTKG QIQLVQSGPE LKKPGETVKI SCKASGYTFT   180
DYSINWVKRA PGKGLKWMGW INTETREPAY AYDFRGRFAF SLETSASTAY LQINNLKYED   240
```

```
TATYFCALDY SYAMDYWGQG TSVTVSSAAA TTTPAPRPPT PAPTIASQPL SLRPEACRPA      300
AGGAVHTRGL DFACDIYIWA PLAGTCGVLL LSLVITLYCK RGRKKLLYIF KQPFMRPVQT      360
TQEEDGCSCR FPEEEEGGCE LRVKFSRSAD APAYQQGQNQ LYNELNLGRR EEYDVLDKRR      420
GRDPEMGGKP RRKNPQEGLY NELQKDKMAE AYSEIGMKGE RRRGKGHDGL YQGLSTATKD      480
TYDALHMQAL PPR                                                        493

SEQ ID NO: 2            moltype = AA  length = 486
FEATURE                 Location/Qualifiers
REGION                  1..486
                        note = Anti-CD19 CAR
source                  1..486
                        mol_type = protein
                        organism = synthetic construct
SEQUENCE: 2
MALPVTALLL PLALLLHAAR PDIQMTQTTS SLSASLGDRV TISCRASQDI SKYLNWYQQK      60
PDGTVKLLIY HTSRLHSGVP SRFSGSGSGT DYSLTISNLE QEDIATYFCQ QGNTLPYTFG     120
GGTKLEITGG GGSGGGGSGG GGSEVKLQES GPGLVAPSQS LSVTCTVSGV SLPDYGVSWI     180
RQPPRKGLEW LGVIWGSETT YYNSALKSRL TIIKDNSKSQ VFLKMNSLQT DDTAIYYCAK     240
HYYYGGSYAM DYWGQGTSVT VSSTTTPAPR PPTPAPTIAS QPLSLRPEAC RPAAGGAVHT     300
RGLDFACDIY IWAPLAGTCG VLLLSLVITL YCKRGRKKLL YIFKQPFMRP VQTTQEEDGC     360
SCRFPEEEEG GCELRVKFSR SADAPAYQQG QNQLYNELNL GRREEYDVLD KRRGRDPEMG     420
GKPRRKNPQE GLYNELQKDK MAEAYSEIGM KGERRRGKGH DGLYQGLSTA TKDTYDALHM     480
QALPPR                                                                486

SEQ ID NO: 3            moltype =     length =
SEQUENCE: 3
000

SEQ ID NO: 4            moltype = AA  length = 5
FEATURE                 Location/Qualifiers
REGION                  1..5
                        note = Linker
source                  1..5
                        mol_type = protein
                        organism = synthetic construct
SEQUENCE: 4
DGGGS                                                                   5

SEQ ID NO: 5            moltype = AA  length = 5
FEATURE                 Location/Qualifiers
REGION                  1..5
                        note = Linker
source                  1..5
                        mol_type = protein
                        organism = synthetic construct
SEQUENCE: 5
TGEKP                                                                   5

SEQ ID NO: 6            moltype = AA  length = 4
FEATURE                 Location/Qualifiers
REGION                  1..4
                        note = Linker
source                  1..4
                        mol_type = protein
                        organism = synthetic construct
SEQUENCE: 6
GGRR                                                                    4

SEQ ID NO: 7            moltype =     length =
SEQUENCE: 7
000

SEQ ID NO: 8            moltype = AA  length = 14
FEATURE                 Location/Qualifiers
REGION                  1..14
                        note = Linker
source                  1..14
                        mol_type = protein
                        organism = synthetic construct
SEQUENCE: 8
EGKSSGSGSE SKVD                                                        14

SEQ ID NO: 9            moltype = AA  length = 18
FEATURE                 Location/Qualifiers
REGION                  1..18
                        note = Linker
source                  1..18
                        mol_type = protein
                        organism = synthetic construct
```

| | | |
|---|---|---|
| SEQUENCE: 9 | | |
| KESGSVSSEQ LAQFRSLD | | 18 |
| | | |
| SEQ ID NO: 10 | moltype = AA  length = 8 | |
| FEATURE | Location/Qualifiers | |
| REGION | 1..8 | |
| | note = Linker | |
| source | 1..8 | |
| | mol_type = protein | |
| | organism = synthetic construct | |
| SEQUENCE: 10 | | |
| GGRRGGGS | | 8 |
| | | |
| SEQ ID NO: 11 | moltype = AA  length = 9 | |
| FEATURE | Location/Qualifiers | |
| REGION | 1..9 | |
| | note = Linker | |
| source | 1..9 | |
| | mol_type = protein | |
| | organism = synthetic construct | |
| SEQUENCE: 11 | | |
| LRQRDGERP | | 9 |
| | | |
| SEQ ID NO: 12 | moltype = AA  length = 12 | |
| FEATURE | Location/Qualifiers | |
| REGION | 1..12 | |
| | note = Linker | |
| source | 1..12 | |
| | mol_type = protein | |
| | organism = synthetic construct | |
| SEQUENCE: 12 | | |
| LRQKDGGGSE RP | | 12 |
| | | |
| SEQ ID NO: 13 | moltype = AA  length = 16 | |
| FEATURE | Location/Qualifiers | |
| REGION | 1..16 | |
| | note = Linker | |
| source | 1..16 | |
| | mol_type = protein | |
| | organism = synthetic construct | |
| SEQUENCE: 13 | | |
| LRQKDGGGSG GGSERP | | 16 |
| | | |
| SEQ ID NO: 14 | moltype =    length = | |
| SEQUENCE: 14 | | |
| 000 | | |
| | | |
| SEQ ID NO: 15 | moltype = AA  length = 7 | |
| FEATURE | Location/Qualifiers | |
| REGION | 1..7 | |
| | note = Protease Cleavage Site | |
| source | 1..7 | |
| | mol_type = protein | |
| | organism = synthetic construct | |
| SEQUENCE: 15 | | |
| ENLYFQG | | 7 |
| | | |
| SEQ ID NO: 16 | moltype = AA  length = 7 | |
| FEATURE | Location/Qualifiers | |
| REGION | 1..7 | |
| | note = Protease Cleavage Site | |
| source | 1..7 | |
| | mol_type = protein | |
| | organism = synthetic construct | |
| SEQUENCE: 16 | | |
| ENLYFQS | | 7 |
| | | |
| SEQ ID NO: 17 | moltype = AA  length = 22 | |
| FEATURE | Location/Qualifiers | |
| REGION | 1..22 | |
| | note = Self-Cleaving Polypeptide Cleavage Site | |
| source | 1..22 | |
| | mol_type = protein | |
| | organism = synthetic construct | |
| SEQUENCE: 17 | | |
| GSGATNFSLL KQAGDVEENP GP | | 22 |
| | | |
| SEQ ID NO: 18 | moltype = AA  length = 19 | |
| FEATURE | Location/Qualifiers | |

```
REGION                      1..19
                            note = Self-Cleaving Polypeptide Cleavage Site
source                      1..19
                            mol_type = protein
                            organism = synthetic construct
SEQUENCE: 18
ATNFSLLKQA GDVEENPGP                                                        19

SEQ ID NO: 19               moltype = AA  length = 14
FEATURE                     Location/Qualifiers
REGION                      1..14
                            note = Self-Cleaving Polypeptide Cleavage Site
source                      1..14
                            mol_type = protein
                            organism = synthetic construct
SEQUENCE: 19
LLKQAGDVEE NPGP                                                             14

SEQ ID NO: 20               moltype = AA  length = 21
FEATURE                     Location/Qualifiers
REGION                      1..21
                            note = Self-Cleaving Polypeptide Cleavage Site
source                      1..21
                            mol_type = protein
                            organism = synthetic construct
SEQUENCE: 20
GSGEGRGSLL TCGDVEENPG P                                                     21

SEQ ID NO: 21               moltype = AA  length = 18
FEATURE                     Location/Qualifiers
REGION                      1..18
                            note = Self-Cleaving Polypeptide Cleavage Site
source                      1..18
                            mol_type = protein
                            organism = synthetic construct
SEQUENCE: 21
EGRGSLLTCG DVEENPGP                                                         18

SEQ ID NO: 22               moltype = AA  length = 13
FEATURE                     Location/Qualifiers
REGION                      1..13
                            note = Self-Cleaving Polypeptide Cleavage Site
source                      1..13
                            mol_type = protein
                            organism = synthetic construct
SEQUENCE: 22
LLTCGDVEEN PGP                                                              13

SEQ ID NO: 23               moltype = AA  length = 23
FEATURE                     Location/Qualifiers
REGION                      1..23
                            note = Self-Cleaving Polypeptide Cleavage Site
source                      1..23
                            mol_type = protein
                            organism = synthetic construct
SEQUENCE: 23
GSGQCTNYAL LKLAGDVESN PGP                                                   23

SEQ ID NO: 24               moltype = AA  length = 20
FEATURE                     Location/Qualifiers
REGION                      1..20
                            note = Self-Cleaving Polypeptide Cleavage Site
source                      1..20
                            mol_type = protein
                            organism = synthetic construct
SEQUENCE: 24
QCTNYALLKL AGDVESNPGP                                                       20

SEQ ID NO: 25               moltype = AA  length = 14
FEATURE                     Location/Qualifiers
REGION                      1..14
                            note = Self-Cleaving Polypeptide Cleavage Site
source                      1..14
                            mol_type = protein
                            organism = synthetic construct
SEQUENCE: 25
LLKLAGDVES NPGP                                                             14

SEQ ID NO: 26               moltype = AA  length = 25
```

```
FEATURE                 Location/Qualifiers
REGION                  1..25
                        note = 27
source                  1..25
                        mol_type = protein
                        organism = synthetic construct
SEQUENCE: 26
GSGVKQTLNF DLLKLAGDVE SNPGP                                          25

SEQ ID NO: 27           moltype = AA  length = 22
FEATURE                 Location/Qualifiers
REGION                  1..22
                        note = Self-Cleaving Polypeptide Cleavage Site
source                  1..22
                        mol_type = protein
                        organism = synthetic construct
SEQUENCE: 27
VKQTLNFDLL KLAGDVESNP GP                                             22

SEQ ID NO: 28           moltype = AA  length = 14
FEATURE                 Location/Qualifiers
REGION                  1..14
                        note = Self-Cleaving Polypeptide Cleavage Site
source                  1..14
                        mol_type = protein
                        organism = synthetic construct
SEQUENCE: 28
LLKLAGDVES NPGP                                                      14

SEQ ID NO: 29           moltype = AA  length = 19
FEATURE                 Location/Qualifiers
REGION                  1..19
                        note = Self-Cleaving Polypeptide Cleavage Site
source                  1..19
                        mol_type = protein
                        organism = synthetic construct
SEQUENCE: 29
LLNFDLLKLA GDVESNPGP                                                 19

SEQ ID NO: 30           moltype = AA  length = 19
FEATURE                 Location/Qualifiers
REGION                  1..19
                        note = Self-Cleaving Polypeptide Cleavage Site
source                  1..19
                        mol_type = protein
                        organism = synthetic construct
SEQUENCE: 30
TLNFDLLKLA GDVESNPGP                                                 19

SEQ ID NO: 31           moltype = AA  length = 14
FEATURE                 Location/Qualifiers
REGION                  1..14
                        note = Self-Cleaving Polypeptide Cleavage Site
source                  1..14
                        mol_type = protein
                        organism = synthetic construct
SEQUENCE: 31
LLKLAGDVES NPGP                                                      14

SEQ ID NO: 32           moltype = AA  length = 17
FEATURE                 Location/Qualifiers
REGION                  1..17
                        note = Self-Cleaving Polypeptide Cleavage Site
source                  1..17
                        mol_type = protein
                        organism = synthetic construct
SEQUENCE: 32
NFDLLKLAGD VESNPGP                                                   17

SEQ ID NO: 33           moltype = AA  length = 20
FEATURE                 Location/Qualifiers
REGION                  1..20
                        note = Self-Cleaving Polypeptide Cleavage Site
source                  1..20
                        mol_type = protein
                        organism = synthetic construct
SEQUENCE: 33
QLLNFDLLKL AGDVESNPGP                                                20
```

```
SEQ ID NO: 34          moltype = AA   length = 24
FEATURE                Location/Qualifiers
REGION                 1..24
                       note = Self-Cleaving Polypeptide Cleavage Site
source                 1..24
                       mol_type = protein
                       organism = synthetic construct
SEQUENCE: 34
APVKQTLNFD LLKLAGDVES NPGP                                              24

SEQ ID NO: 35          moltype = AA   length = 40
FEATURE                Location/Qualifiers
REGION                 1..40
                       note = Self-Cleaving Polypeptide Cleavage Site
source                 1..40
                       mol_type = protein
                       organism = synthetic construct
SEQUENCE: 35
VTELLYRMKR AETYCPRPLL AIHPTEARHK QKIVAPVKQT                              40

SEQ ID NO: 36          moltype = AA   length = 18
FEATURE                Location/Qualifiers
REGION                 1..18
                       note = Self-Cleaving Polypeptide Cleavage Site
source                 1..18
                       mol_type = protein
                       organism = synthetic construct
SEQUENCE: 36
LNFDLLKLAG DVESNPGP                                                     18

SEQ ID NO: 37          moltype = AA   length = 40
FEATURE                Location/Qualifiers
REGION                 1..40
                       note = Self-Cleaving Polypeptide Cleavage Site
source                 1..40
                       mol_type = protein
                       organism = synthetic construct
SEQUENCE: 37
LLAIHPTEAR HKQKIVAPVK QTLNFDLLKL AGDVESNPGP                              40

SEQ ID NO: 38          moltype = AA   length = 33
FEATURE                Location/Qualifiers
REGION                 1..33
                       note = Self-Cleaving Polypeptide Cleavage Site
source                 1..33
                       mol_type = protein
                       organism = synthetic construct
SEQUENCE: 38
EARHKQKIVA PVKQTLNFDL LKLAGDVESN PGP                                    33
```